United States Patent
Ryder

(10) Patent No.: US 8,377,639 B2
(45) Date of Patent: Feb. 19, 2013

(54) COMPOUNDS FOR MODULATING RNA BINDING PROTEINS AND USES THEREFOR

(75) Inventor: Sean Ryder, West Boylston, MA (US)

(73) Assignee: University of Massachusetts, Boston, MA (US)

( * ) Notice: Subject to any disclaimer, the term of this patent is extended or adjusted under 35 U.S.C. 154(b) by 29 days.

(21) Appl. No.: 12/823,902

(22) Filed: Jun. 25, 2010

(65) Prior Publication Data

US 2011/0065704 A1    Mar. 17, 2011

Related U.S. Application Data

(60) Provisional application No. 61/220,985, filed on Jun. 26, 2009.

(51) Int. Cl.
| | |
|---|---|
| *C12Q 1/68* | (2006.01) |
| *A01N 41/06* | (2006.01) |
| *A01N 43/653* | (2006.01) |
| *A61K 31/18* | (2006.01) |
| *A61K 31/4196* | (2006.01) |

(52) U.S. Cl. ...... 435/6.1; 514/383; 514/604; 548/263.6; 548/264.8; 564/89; 564/92; 564/152; 564/191

(58) Field of Classification Search .................. None
See application file for complete search history.

(56) References Cited

U.S. PATENT DOCUMENTS 3,953,492 A * 4/1976 Mrozik ............................ 558/6

FOREIGN PATENT DOCUMENTS

| WO | WO86/03941 A1 | 7/1986 |
| WO | WO02/083629 A1 | 10/2002 |
| WO | WO2004/046095 A1 | 6/2004 |
| WO | WO2006/110762 A2 | 10/2006 |

OTHER PUBLICATIONS

Massacret et al., Palladium(0)-Catalyzed Asymmetric Synthesis of 1,2,3,4-Tetrahydro-2-vinylquinoxalines, Eur. J. Org. Chem. 1999, 129-134.*
Seftel et al., Comparison of Piperazine and Tetramisole in Treatment of Ascariasis, Brit. med. J., 1968, 4, 93-95.*
International Search Report and Written Opinion issued in PCT/US2010/040035 on Jun. 29, 2011.
Mueller, Joachim et al., "Thioureides of 2-(phenoxymethyl)benzoic acid 4-R substituted: A novel class of anti-parasitic compounds", Parasitology International, 2009, 58(2), pp. 128-135. (Available online Dec. 25, 2008).

* cited by examiner

*Primary Examiner* — Jim Ketter
*Assistant Examiner* — Reza Ghafoorian
(74) *Attorney, Agent, or Firm* — McCarter & English, LLP; Elizabeth A. Hanley, Esq.; Jill Mello

(57) ABSTRACT

The invention relates to compositions and methods for inhibiting RNA binding proteins (e.g., MEX-3, MEX-5 and POS-1), as well as methods for treating and preventing disorders associated with parasitic infections and inflammatory disorders.

28 Claims, No Drawings

US 8,377,639 B2

COMPOUNDS FOR MODULATING RNA BINDING PROTEINS AND USES THEREFOR

RELATED APPLICATIONS

This application claims priority to U.S. Provisional Patent Application No. 61/220,985, filed Jun. 26, 2009. The entire contents of the foregoing application are hereby incorporated in their entirety.

GOVERNMENT INTERESTS

This invention was made with government support under grant nos. 1R21NS059380 and 3R21NS059380-01S1 awarded by the National Institutes of Health. The government has certain rights in the invention.

SUBMISSION ON COMPACT DISC

This application incorporates by reference the ASCII text file identified by the name SequenceListing.txt, containing 1.49 KB of data, created on Nov. 12, 2010 and filed in computer-readable format (CRF).

BACKGROUND OF THE INVENTION

According to the World Health Organization (WHO), more than one-third of the world's population, approximately 2 billion people, is infested with helminths. In 1999, the WHO estimated that schistosomiasis and soil-based helminths represented more than 40% of the disease burden due to all tropical disease, excluding malaria. While most parasitic infestations are preventable and treatable, the effects of an infestation can be chronic and long-term and may eventually cause death. For example, a person who has endured persistent and heavy infestations is likely to suffer from anemia, malnutrition and chronic irreversible diseases, such as liver fibrosis, cancer of the bladder and kidney failure. These parasites also affect livestock, which can facilitate infestation in humans by causing contamination via soil or food supplies.

In addition to the health risk posed to humans by parasites, plants are highly susceptible to parasitic infestations. Effects of nematode damage to plants include stunting, chlorosis, nutrient deficiencies, wilting, root abnormalities and reduced yield.

While there are a number of antihelminthic treatments currently available, some scientists are concerned that the parasites will develop resistance to these treatments, especially in developing countries where people are repeatedly infected with helminths and receive multiple doses of antihelminthic drugs. In fact, resistance to antihelminthic drugs has been observed in livestock due to frequent and repeated treatments. Moreover, rates of re-infection by helminths are very high due to the number and the durability of infective eggs on surfaces and in soil. While infection is active, some parasitic nematode species (e.g., *Ascaris lumbricoides*) release an estimated 100,000 new embryos per adult female per day. Currently available anti-helminthics work by paralyzing the infectious nematode through blocking ion channels and receptors and do not inactivate the embryos that cause re-infection. Therefore, it is advantageous to develop new therapies for the treatment and prevention of parasitic infestations and, in particular, therapies that limit the possibility of parasitic re-infection, in both plants and animals,

SUMMARY OF THE INVENTION

The present invention is based, at least in part, on the development and use of screening assays to identify compounds that inhibit the RNA-binding activity of MEX-3, MEX-5 and/or POS-1, RNA binding proteins which are required for early embryogenesis in parasitic worms. The identified compounds represent a novel class of anti-parasitic agents that specifically target parasitic worm embryos.

Accordingly, in one aspect, the invention pertains, at least in part, to method for treating or preventing a parasitic associated state in a subject comprising administering to the subject an effective amount of an RNA binding modulatory compound (e.g., a compound of formula I, Ia, Ib, II, IIa, IIb, IIc, III, IV, V, VI, VIa, VIb, VII, VIIa, VIIb, VIIc, VIId, VIIe, VIIf or a compound of Table 1 or 2), such that the parasitic associated state is treated or prevented. In one embodiment, the parasitic associated state is a parasitic infestation or re-infestation. In another embodiment, the parasitic associated state is a disease caused by a parasitic infestation.

In one embodiment, the invention pertains, at least in part, to a method for treating or preventing a parasitic infestation in a subject infested with or at risk for infestation with parasites by administering to the subject a therapeutically or pesticidally effective amount of an RNA binding modulatory compound, e.g., a compound of formula I, Ia, Ib, II, IIa, IIb, IIc, III, IV, V, VI, VIa, VIb, VII, VIIa, VIIb, VIIc, VIId, VIIe, VIIf or a compound of Table 1 or 2, such that the parasitic infestation is treated or prevented.

In another embodiment, the invention pertains, at least in part, to a method for protection of plants from a parasitic infestation by administering to the plants a pesticidally effective amount of an RNA binding modulatory compound, e.g., a compound of formula I, Ia, Ib, II, IIa, IIb, IIc, III, IV, V, VI, VIa, VIb, VII, VIIa, VIIb, VIIc, VIId, VIIe, VIIf or a compound of Table 1 or 2, such that the plants are protected.

In yet another embodiment, the invention pertains, at least in part, to a method for inhibiting parasitic embryogenesis in a parasite or in a subject suffering from a parasitic infection by administering to the parasite or subject suffering from the parasitic infection a therapeutically or pesticidally effective amount of an RNA binding modulatory compound, e.g., a compound of formula I, Ia, Ib, II, IIa, IIb, IIc, III, IV, V, VI, VIa, VIb, VII, VIIa, VIIb, VIIc, VIId, VIIe, VIIf or a compound of Table 1 or 2, such that embryogenesis is inhibited.

In a further embodiment, the invention pertains, at least in part, to a method for reducing parasitic burden in soil, in plants or in an animal suffering from a parasitic infection by administering to the soil, plants or animal a therapeutically or pesticidally effective amount of an RNA binding modulatory compound, e.g., a compound of formula I, Ia, Ib, II, IIa, IIb, IIc, III, IV, V, VI, VIa, VIb, VII, VIIa, VIIb, VIIc, VIId, VIIe, VIIf or a compound of Table 1 or 2, such that the parasitic burden is reduced.

In another embodiment, the invention pertains, at least in part, to a method for treating or preventing a disease caused by a parasitic infestation in a subject by administering to the subject a therapeutically effective amount of an RNA binding modulatory compound, e.g., a compound of formula I, Ia, Ib, II, IIa, IIb, IIc, III, IV, V, VI, VIa, VIb, VII, VIIa, VIIb, VIIc, VIId, VIIe, VIIf or a compound of Table 1 or 2, such that the disease is treated or prevented.

In one embodiment, the invention pertains, at least in part, to a method for treating or preventing an inflammatory disorder in a subject by administering to the subject a therapeutically effective amount of an RNA binding modulatory compound, e.g., a compound of formula I, Ia, Ib, II, IIa, IIb, IIc, III, IV, V, VI, VIa, VIb, VII, VIIa, VIIb, VIIc, VIId, VIIe, VIIf or a compound of Table 1 or 2, such that the inflammatory disorder is treated.

In one embodiment, the subject is a plant. In one embodiment, the subject is an animal. In one embodiment, the subject is a human.

In one embodiment, the parasite is present in a subject. In one embodiment, the parasite is a helminth, e.g., a cestode, a trematode and a nematode. In one embodiment, the helminth is a nematode.

In one embodiment, the RNA binding modulatory protein modulates the RNA binding activity of an RNA binding protein. In one embodiment, the RNA binding protein is required for embryogenesis. In one embodiment, the RNA binding protein comprises a CCCH zinc finger motif. In one embodiment, the RNA binding protein comprises a KH domain. In one embodiment, the RNA binding protein is selected from the group consisting of MEX-5, POS-1 and MEX-3, or a homolog thereof. In one embodiment, the RNA binding protein is MEX-5 or a homolog thereof. In one embodiment, the RNA binding protein is MEX-3 or a homolog thereof. In one embodiment, the RNA binding protein is POS-1 or a homolog thereof.

In another aspect, the invention pertains, at least in part, to a pharmaceutical composition comprising a therapeutically effective amount of an RNA binding modulatory compound, e.g., a compound of formula I, Ia, Ib, II, IIa, IIb, IIc, III, IV, V, VI, VIa, VIb, VII, VIIa, VIIb, VIIc, VIId, VIIe, VIIf or a compound of Table 1 or 2, and a pharmaceutically acceptable carrier.

In another aspect, the invention pertains, at least in a part, to a composition comprising a pesticidally effective amount of an RNA binding modulatory compound, e.g., a compound of formula I, Ia, Ib, II, IIa, IIb, IIc, III, IV, V, VI, VIa, VIb, VII, VIIa, VIIb, VIIc, VIId, VIIe, VIIf or a compound of Table 1 or 2, and an agronomically acceptable carrier.

In yet another aspect, the present invention provides methods of identifying a compound useful in modulating a biological activity of an RNA-binding protein. The methods include providing an indicator composition comprising an RNA-binding protein and an RNA molecule comprising an RNA-binding protein recognition element; contacting the indicator composition with each member of a library of test compounds; determining the effect of the compound on a biological activity of the RNA-binding protein; and selecting a compound that modulates the biological activity of the RNA-binding protein as compared to an appropriate control, thereby identifying a compound useful in modulating a biological activity of an RNA-binding protein.

In another aspect, the invention provides methods of identifying a compound useful in modulating a biological activity of an RNA-binding protein. The methods include providing an indicator composition comprising an RNA-binding protein and an RNA molecule comprising an RNA-binding protein recognition element; contacting the indicator composition with each member of a library of test compounds under conditions which allow binding of the RNA-binding protein to the RNA molecule comprising an RNA-binding protein recognition element to form a complex; and detecting the formation of a complex of the RNA-binding protein and the RNA molecule comprising an RNA-binding protein recognition element, wherein the ability of the compound to modulate interaction of the RNA-binding protein and the RNA molecule comprising an RNA-binding protein recognition element is indicated by a modulation of complex formation in the presence of the compound as compared to the formation of complex in the absence of the compound, thereby identifying a compound useful in modulating a biological activity of an RNA-binding protein.

In one aspect, the present invention provides methods of identifying a compound useful in modulating embryogenesis. The methods include providing an indicator composition comprising an RNA-binding protein and an RNA molecule comprising an RNA-binding protein recognition element; contacting the indicator composition with each member of a library of test compounds under conditions which allow binding of the RNA-binding protein to the RNA molecule comprising an RNA-binding protein recognition element to form a complex; and detecting the formation of a complex of the RNA-binding protein and the RNA molecule comprising an RNA-binding protein recognition element, wherein the ability of the compound to modulate interaction of the RNA-binding protein and the RNA molecule comprising an RNA-binding protein recognition element is indicated by a modulation of complex formation in the presence of the compound as compared to the amount of complex formed in the absence of the compound, thereby identifying a compound useful in modulating embryogenesis.

In another aspect, the present invention provides methods of identifying a compound useful for treating a subject with a parasitic-associated state. The methods include providing an indicator composition comprising an RNA-binding protein and an RNA molecule comprising an RNA-binding protein recognition element; contacting the indicator composition with each member of a library of test compounds under conditions which allow binding of the RNA-binding protein to the RNA molecule comprising an RNA-binding protein recognition element to form a complex; and detecting the formation of a complex of the RNA-binding protein and the RNA molecule comprising an RNA-binding protein recognition element, wherein the ability of the compound to modulate interaction of the RNA-binding protein and the RNA molecule comprising an RNA-binding protein recognition element is indicated by modulation of complex formation in the presence of the compound as compared to the amount of complex formed in the absence of the compound, thereby identifying a compound useful for treating a subject with a parasitic-associated state.

The biological activity of the RNA-binding protein may be determined by measuring the interaction of the RNA-binding protein and an RNA-binding protein recognition element. Alternatively, the biological activity of the RNA-binding protein may be determined by determining the ability of the compound to modulate a biological activity selected from the group consisting of anterior patterning, germ cell totipotency, development of the intestine, development of germline blastomeres, development of pharyngeal tissue, expression and/or activity of PAL-1, NOS-2, APX-1 protein, and GLP-1.

The indicator composition may be a cell that expresses the RNA-binding protein or a cell-free composition.

In one embodiment, the RNA-binding protein comprises a CCCH-type tandem zinc finger. In one embodiment, the RNA-binding protein comprising the CCCH-type tandem zinc finger is POS-1.

In another embodiment, the RNA-binding protein comprises a KH domain. In one embodiment, the RNA-binding protein comprising the KH domain is MEX-3.

In one embodiment, the RNA-binding protein recognition element comprises the consensus sequence $UA(U_{2-3})RD(N_{1-3})G$. In another embodiment, the RNA-binding protein recognition element comprises the consensus sequence $DKAG(N_{0-3})UHUA$.

Detecting the formation of a complex of the RNA-binding protein and the RNA molecule may be determined by a gel-shift assay or a fluorescence polarization assay. In one embodiment, the RNA-binding protein recognition element is fluorescently labeled.

The methods of the invention may further comprise determining the effect of the test compound on a parasitic-associated state in a non-human animal, comprising administering the test compound to the animal and determining the effect of test compound on the parasitic-associated state in the presence and absence of the test compound. Determining the effect of the test compound on a parasitic-associated state may be determined by measuring an immune response in the non-human animal.

In one embodiment, the test compound increases the formation or stability of the complex. In another embodiment, the test compound decreases the formation or stability of the complex.

In another aspect, the invention provides compounds identified according to the method of the invention which may be in the form of a composition.

One aspect of the invention provides to methods of inhibiting embryogenesis in a parasite comprising contacting the parasite with a compound identified according to the methods of the invention.

In another aspect, the invention provides methods of treating a parasite-associated state in a subject, comprising administering a composition comprising a compound identified in the methods of the invention to the subject, thereby treating a parasite-associated state in the subject.

DETAILED DESCRIPTION OF THE INVENTION

The invention pertains generally to a method for treating or preventing a parasitic associated state in a subject comprising administering to the subject an effective amount of an RNA binding modulatory compound (e.g., a compound of formula I, Ia, Ib, II, IIa, IIb, IIc, III, IV, V, VI, VIa, VIb, VII, VIIa, VIIb, VIIc, VIId, VIIe, VIIf or a compound of Table 1 or 2), such that the parasitic associated state is treated or prevented.

The term "parasitic associated state" includes those diseases and disorders associated with parasites. In one embodiment, the parasitic associated state is a parasitic infestation. In one embodiment, the parasitic associated state is a disease caused by a parasitic infestation. In one embodiment, the parasitic associated state is a parasitic re-infestation.

As used herein, the term "RNA binding modulatory compound" includes those compounds that are capable of modulating the activity of an RNA-binding protein (e.g., an RNA-binding protein required for embryogenesis in a parasitic worm), e.g., the binding of an RNA-binding protein to a target RNA (e.g., an RNA molecule comprising an RNA-binding recognition element of the RNA-binding protein). In one embodiment, the RNA binding modulatory compound is a compound of formula I, Ia, Ib, II, IIa, IIb, IIc, III, IV, V, VI, VIa, VIb, VII, VIIa, VIIb, VIIc, VIId, VIIe, VIIf or a compound of Table 1 or 2. In one embodiment, the RNA binding modulatory compound includes compounds that are capable of decreasing, inhibiting or preventing the activity of an RNA-binding protein, e.g., the binding of an RNA-binding protein to a target RNA (e.g., an RNA molecule comprising an RNA-binding recognition element of the RNA-binding protein). In another embodiment, the RNA binding modulatory compound includes compounds that are capable of increasing, augmenting or enhancing the activity of an RNA-binding protein, e.g., the binding of an RNA-binding protein to a target RNA (e.g., an RNA molecule comprising an RNA-binding recognition element of the RNA-binding protein).

In various embodiments, the method includes treating a parasitic infestation in a subject infested with parasites, protecting plants from a parasitic infestation, inhibiting embryogenesis in a parasite or in a subject suffering from a parasitic infestation, reducing parasitic burden in soil, in plants or in a mammal suffering from a parasitic infection, treating or preventing an inflammatory disorder and treating a disease in a mammal caused by the growth and replication of a parasite.

In one embodiment, the invention pertains to a method of treating a parasitic infestation in a subject infested with parasites by administering to the subject a therapeutically or pesticidally effective amount of an RNA binding modulatory compound, e.g., a compound of formula I, Ia, Ib, II, IIa, IIb, IIc, III, IV, V, VI, VIa, VIb, VII, VIIa, VIIb, VIIc, VIId, VIIe, VIIf or a compound of Table 1 or 2, such that the subject is treated.

The term "subject" includes animals (e.g., vertebrates, amphibians, fish, mammals, non-human animals), including humans, that are capable of suffering from a parasitic infestation, an inflammatory disorder (e.g., rheumatoid arthritis, psoriasis and multiple sclerosis) or a disease in a mammal caused by a parasitic infection (e.g., helminthiasis). Subjects also include primates, such as chimpanzees, monkeys and the like. In one embodiment of the invention, the subject is suffering from a parasitic infestation or infection, e.g., a helminth infestation. In one embodiment, the subject is at risk for a parasitic infection, e.g., has been exposed to a parasite e.g., a helminth.

The term "subject" also includes agriculturally productive livestock, for example, cattle, sheep, goats, horses, pigs, donkeys, camels, buffalo, rabbits, chickens, turkeys, ducks, geese and bees; and domestic pets, for example, dogs, cats, caged birds and aquarium fish, and also so-called test animals, for example, hamsters, guinea pigs, rats and mice.

The term "subject" also includes plants. The term "plant" includes all plants and plant parts, for example, all plants and plant populations, including wild plants or crop plants (including naturally occurring crop plants). Crop plants may be plants that can be obtained by conventional plant breeding and optimization methods or by biotechnological and recombinant methods or by combinations of these methods, including transgenic plants. Examples of plants include, but are not limited to the following plant cultivars: cereals (wheat, barley, rye, oats, rice, maize, sorghum and related species); beet (sugar beet and fodder beet); pome, stone and berry fruit (apples, pears, plums, peaches, almonds, cherries, strawberries, raspberries and blackberries); legumes (beans, lentils, peas, soya); oil crops (rape, mustard, poppy, olives, sunflowers, coconut, castor oil, cocoa, peanut); cucumber plants (squashes, cucumber, melons); citrus fruits (oranges, lemons, grapefruits, mandarines); vegetables (spinach, lettuce, asparagus, cabbage varieties, carrots, onions, tomatoes, potatoes, paprika); laurels (avocado, cinnamonium, camphor) and plants such as tobacco, cotton, nuts, corn, coffee, aubergines, sugar cane, tea, pepper, vines, hops, grapes, bananas and natural rubber plants, as well as ornamental plants. In one embodiment, the plant is suffering from a parasitic infestation. In another embodiment, the plant is at risk of suffering from a parasitic infestation.

Plant parts also include all parts and organs of plants above and below the ground, such as shoot, leaf, flower and root, examples of which include, for example, leaves, needles, stalks, stems, flowers, fruit bodies, fruits, seeds, roots, tubers and rhizomes. The plant parts also include harvested material, and vegetative and generative propagation material, for example cuttings, tubers, rhizomes, offsets and seeds.

The language "subject" also includes soil. The term "soil" includes the soil used in planting any plants or plant parts as described above. The term "soil" also includes that soil that has not yet been planted with any plants or plant parts. In one embodiment, the soil suffers from a parasitic infestation.

As used herein, the term "treating" may result in prevention of the disease or condition, cure of the disease or condition, a decrease in the type or number of symptoms associated with the condition, either in the long term or short term (i.e., amelioration of the condition) or simply a transient beneficial effect to the subject.

The terms "treating" and "treatment" used in the context of an animal include the administration of a therapeutically effective amount of a RNA binding modulatory compound, e.g., compound of formula I, Ia, Ib, II, IIa, IIb, IIc, III, IV, V, VI, VIa, VIb, VII, VIIa, VIIb, VIIc, VIId, VIIe, VIIf or a compound of Table 1 or 2, to treat the animal for a parasitic associated state, e.g., parasitic infestation, parasitic embryogenesis, an inflammatory disease (e.g., rheumatoid arthritis, psoriasis and multiple sclerosis) or a disease in an animal caused by a parasitic infection (e.g., helminthiasis).

The terms "preventing" and "prevention" used in the context of an animal include the administration of a therapeutically or prophylactically effective amount of a RNA binding modulatory compound, e.g., compound of formula I, Ia, Ib, II, IIa, IIb, IIc, III, IV, V, VI, VIa, VIb, VII, VIIa, VIIb, VIIc, VIId, VIIe, VIIf or a compound of Table 1 or 2, to prevent a parasitic associated state, e.g., parasitic infestation, parasitic embryogenesis, an inflammatory disease (e.g., rheumatoid arthritis, psoriasis and multiple sclerosis) or a disease in an animal caused by a parasitic infection (e.g., helminthiasis), from occurring.

The terms "treating" and "treatment" used in the context of plants include the administration to a plant or to soil a pesticidally effective amount of a RNA binding modulatory compound, e.g., compound of formula I, Ia, Ib, II, IIa, IIb, IIc, III, IV, V, VI, VIa, VIb, VII, VIIa, VIIb, VIIc, VIId, VIIe, VIIf or a compound of Table 1 or 2, to treat the plant or soil for a parasitic associated state, e.g., parasitic infestation, parasitic embryogenesis or reduction of the parasitic burden of the plant or soil.

The terms "preventing" and "prevention" used in the context of plants include the administration of a pesticidally effective amount of a RNA binding modulatory compound, e.g., compound of formula I, Ia, Ib, II, IIa, IIc, IIb, III, IV, V, VI, VIa, VIb, VII, VIIa, VIIb, VIIc, VIId, VIIe, VIIf or a compound of Table 1 or 2, to a plant or to soil to prevent a parasitic associated state, e.g., parasitic infestation or parasitic embryogenesis.

The phrases "parasitic infestation" and "parasitic infection", used interchangeable herein, are intended to include the presence of parasitic organisms or embryos within the subject (e.g., mammal, plant or soil). The term "parasite" includes an animal or plant that lives in or on a host subject (e.g., a mammal, plant or soil). In one embodiment, the parasite is a helminth. The term "helminth" includes eukaryotic, worm-like parasites that live inside their hosts. Examples of helminths include, but are not limited to, flatworms (e.g., plathyhelminths) for example, trematodes (e.g., flukes) and cestodes (e.g., tapeworms); thorny-headed worms (e.g., acanthocephalans); and roundworms (e.g., nematodes). In one embodiment, the parasitic infestation is a helminth infestation. In one embodiment, the parasitic infestation is a nematode infestation. In one embodiment, the helminth or parasitic worm is an intestinal parasite, e.g., a parasitic worm that lives inside the digestive tract. As used herein, the phrase "parasitic re-infestation" or "parasitic re-infection" is intended to include the re-occurrence of a parasitic infestation in a subject.

Examples of trematodes include, for example, *Schistosoma* spp. (e.g., *Schistosoma bovis, Schistosoma curassoni, Schistosoma edwardiense, Schistosoma guineensis, Schistosoma haematobium, Schistosoma hippotami, Schistosoma incognitum, Schistosoma indicum, Schistosoma intercalatum, Schistosoma japonicum, Schistosoma lieperi, Schistosoma malayenesis, Schistosoma mansoni, Schistosoma margrebowiei, Schistosoma mattheei, Schistosoma mekongi, Schistosoma ovuncatum, Schistosoma nasale, Schistosoma rodhaini, Schistosoma sinesium, Schistosoma spindale, Schistosoma sinensium*), *Trichobilharzia regenti, Clonorchis sinensis, Dicrocoelium dendriticum, Dicrocoelium hospes, Fasciola hepatica, Fascioloides magna, Fasciola giganta, Fasciola jacksoni, Metorchis conjunctus, Metorchis albidus, Protofasciola robusta, Parafasciolopsis fasciomorphae, Opisthorchis viverrini, Opisthorchis felineus, Opisthorchis guayaquilensis, Paragonimus westermani*, and *Fasciolopsis buski*).

Examples of cestodes include, for example, cyclophillidea (e.g., *Dipylidium caninum, Taenia crassiceps, Taenia hydatigena, Taenia multiceps, Taenia pisiformis, Taenia serialis, Taenia taeniaeformis, Echinococcus granulosus, Echinococcus multilocularis, Echinococcus shiquicus, Echinococcus oligarthrus, Echinococcus vogeli, Echinococcus ortleppi, Echinococcus equinus, Taenia saginata, Taenia solium, Hymenolepis nana, Hymenolepis diminuta*) and pseudophyllidea (e.g., *Diphyllobothrium latum, Diphyllobothrium pacificum, Diphyllobothrium cordatum, Diphyllobothrium ursi, Diphyllobothrium dendriticum, Diphyllobothrium lanceolatum, Diphyllobothrium dalliae, Diphyllobothrium yonagoensis, Diphyllobothrium mansonoides, Spirometra erinaceieuropaei, Spirometra mansonoides*).

Examples of nematodes include, for example, *Dracunculus medinensis, Onchocerca volvulus, Loa loa, Mansonella perstans, Mansonella ozzardi, Mansonella streptocera, Dirofilaria immitis, Dirofilaria repens, Acanthocheilonema viteae, Brugia malayi, Brugia pahangi, Brugia timori, Cercopithifilaria johnstoni, Dipetalonema reconditum, Dipetalonema repens, Dirofilaria immitis, Dirofilaria repens, Dirofilaria tenuis, Dirofilaria ursi, Elaeophora abramovi, Elaeophora bohmi, Elaeophora elaphi, Elaeophora poeli, Elaeophora sagitta, Elaeophora schneideri, Foleyella furcata, Litomosa westi, Litomosoides brasiliensis, Litomosoides sigmodontis, Litomosoides wilsoni, Ochoterenella digiticauda, Onchocerca gibsoni, Onchocerca gutturosa, Onchocerca volvulus, Piratuba digiticauda, Sarconema eurycerca, Waltonella flexicauda, Wuchereria bancrofti, Wuchereria kalimantani, Gnathostoma binucleatum, Gnathostoma doloresi, Gnathostoma hispidum, Gnathostoma lamothei, Gnathostoma malaysiae, Gnathostoma nipponicum, Gnathostoma spinigerum, Gnathostoma turgidum, Ancylostoma brazilienese, Ancylostoma caninum, Ancylostoma ceylanicum, Ancylostoma duodenale, Ancylostoma pluridenatum, Ancylostoma tubaeforme, Necator americanus, Angiostrongylus cantonensis, Mermis nigrescens, Trichuris trichiura, Trichinella spiralis, Caenorhabditis elegans, Strongyloides stercoralis, Micronema (Halicephalobus) delatrix, Haemonchus contortus, Ostertagia sp., Nematodirus sp., Nippostrongylus brasiliensis, Heligmosomoides polygyrus, Dictyocaulus viviparous, Toxocara canis, Anisakis sp., Enterobius sp., Thelazia sp., Ascaris lumbricoides, Ascaris suum, Anisakis pegreffi, Anisakis physeteris, Anisakis schupakovi, Anisakis simplex, Anisakis typical, Anisakis ziphidarum, Toxocara cati, Baylisacaris procyonis,*

*Baylisacaris melis, Baylisacaris transfuga, Baylisacaris columnaris, Baylisacaris devosi, Baylisacaris laevis, Strongyloides stercoralis, Enterobius vermicularis, Enterobius anthropopitheci, Enterobius gregorii, Trichinella spiralis, Trichuris trichiura, Trichocephalus trichiuris, Capillaria philippinensis, Belonolaimus anama, Belonolaimus euthychilus, Belonolaimus gracilis, Belonolaimus jara, Belonolaimus lineatus, Belonolaimus lolii, Belonolaimus longicaudatus, Belonolaimus maritimus, Belonolaimus nortoni, Criconemoides sp., Helicotylenchus digonicus, Helicotylenchus labiodiscinus, Helicotylenchus leiocephalus, Helicotylenchus platyurus, Helicotylenchus pseudorobustus, Heterodera zeae, Hoplolaimus tylenchiformis, Hoplolaimus galeatus, Hoplolaimus columbus, Xiphinema americanumv, Longidorus elongatus, Longidorus breviannulatus, Meloidogyne chitwoodi, Meloidogyne graminis, Meloidogyne hapla, Meloidogyne mayaguenesis, Meloidogyne partityla, Pratylenchus agilis, Pratylenchus alleni, Pratylenchus coffeae, Pratylenchus convallariae, Pratylenchus crenatus, Pratylenchus flakkensis, Pratylenchus hexincisus, Pratylenchus loosi, Pratylenchus penetrans, Pratylenchus pseudopratensis, Pratylenchus scribneri, Pratylenchus thornei, Trichodorus obtusus, Trichodorus proximus, Tylenchorhynchus cylindricus, Tylenchorhynchus hordei, Tylenchorhynchus nudus, Tylenchorhynchus robustus, Globodera pallida, Globodera rostochiensis, Globodera achilleae, Globodera artemisiae, Globodera chaubattia, Globodera hypolysi, Globodera leptonepia, Globodera millefolii, Globodera mirabilis, Globodera pseudorostochiensis, Globodera tabacum solanacearum, Globodera tabacum tabacum, Globodera tabacum virginae, Globodera zelandica, Ditylenchus destructor, Heterodera glycines, Heterodera schachtii, Nacobbus aberrrans, Criconemella inusitatus, Bursaphelenchus xylophilis, Radopholus simila, Rotylenchulus reniformis, Tylenchulus semipenetrans, Belonolaimus longicaudatus, Macroposthonia curvata, Macroposthonia discus, Macroposthonia annulata, Macroposthonia rustica, Macroposthonia sphaerocephalus, Macroposthonia xenoplax, Aphelenchoides besseyi, Aphelenchoides bicaudatus, Aphelenchoides centralis, Aphelenchoides clarus, Aphelenchoides confusus, Aphelenchoides dactylocercus, Aphelenchoides obtusus, Aphelenchoides parietinus, Aphelenchoides pusillus, Aphelenchoides sacchari, Aphelenchoides vigor* and *Ditylenchus dipsaci*. In one embodiment, the nematode is *C. elegans*.

The language "therapeutically effective amount" of the compound includes that amount necessary or sufficient to treat, prevent or ameliorate a disease or disorder (e.g., a parasitic associated state, e.g., parasitic infestation) in a subject (e.g., a subject suffering from or at risk for a parasitic infestation, e.g., infestation by a helminth). A therapeutically effective amount of the compound includes that amount necessary or sufficient to treat, prevent or ameliorate in a subject a parasitic associated state, an inflammatory disorder (e.g., rheumatoid arthritis, psoriasis or multiple sclerosis) or a disease in a subject caused by a parasitic infestation (e.g., helminthiasis). The language "therapeutically effective amount" of the compound also includes that amount necessary to reduce the parasitic burden in a subject and the amount necessary to inhibit parasitic embryogenesis in a parasite or in a subject suffering from a parasitic infestation. The therapeutically effective amount can vary depending on such factors as the size and weight of the subject, the type of illness, etc. One of ordinary skill in the art would be able to study the aforementioned factors and make the determination regarding the effective amount of the compounds without undue experimentation.

The language "pesticidally effective amount" of the compound includes that amount necessary or sufficient to treat, prevent or ameliorate a disease or disorder (e.g., parasitic associated state, e.g., parasitic infestation) in a plant or soil (e.g., plant or soil suffering from or at risk for a parasitic associated state, e.g., parasitic infestation). The language "pestically effective amount" of the compound also includes that amount necessary to reduce the parasitic burden in the soil or plant and the amount necessary to inhibit parasitic embryogenesis in a parasite or in a plant or in the soil comprising a parasitic infestation. The pesticidally effective amount can vary depending on such factors as the type of plant, the type of parasitic infestation, the extent of the parasitic infestation, etc. One of ordinary skill in the art would be able to study the aforementioned factors and make the determination regarding the pesticidally effective amount of the compounds without undue experimentation.

In another embodiment, the invention pertains, at least in part, to a method for protection of plants from a parasitic infestation by administering to the plants a pesticidally effective amount of a an RNA binding modulatory compound, e.g., compound of formula I, Ia, Ib, II, IIa, IIb, IIc, III, IV, V, VI, VIa, VIb, VII, VIIa, VIIb, VIIc, VIId, VIIe, VIIf, or a compound of Table 1 or 2, such that the plants are protected.

The language "protect" and "protection" includes shielding, guarding or preventing plants from damage by a parasitic infestation in or on the plant or in the soil surrounding the plant. The protection can occur by application of a an RNA binding modulatory compound, e.g., compound of formula I, Ia, Ib, II, IIa, IIb, IIc, III, IV, V, VI, VIa, VIb, VII, VIIa, VIIb, VIIc, VIId, VIIe, VIIf or a compound of Table 1 or 2, to the plant itself or to the soil surrounding the plant.

In yet another embodiment, the invention pertains, at least in part, to a method for modulating, e.g., inhibiting, embryogenesis, e.g., in a parasite or in a subject suffering from a parasitic infection, by contacting the parasite or administering to the subject suffering from a parasitic infection a therapeutically effective amount of an RNA binding modulatory compound, e.g., a compound of formula I, Ia, Ib, II, IIa, IIb, IIc, III, IV, V, VI, VIa, VIb, VII, VIIa, VIIb, VIIc, VIId, VIIe, VIIf or a compound of Table 1 or 2, such that embryogenesis is inhibited. The parasite may be located externally from a plant (e.g., on a plant or in the soil) or may be located within the plant or mammal itself.

As used herein, the various forms of the term "modulate" include stimulation (e.g., increasing or upregulating a particular response or activity) and inhibition (e.g., decreasing or downregulating a particular response or activity).

The terms "inhibit" and "inhibiting" refer to decreasing or downregulating a particular response or activity. The terms "inhibit" and "inhibiting" include, for example, the suppression or amelioration of embryogenesis, e.g., parasitic embryogenesis. The terms "inhibit" and "inhibiting" also include, for example, the downmodulating or blocking of the interaction between an RNA binding protein and a target RNA.

The language "embryogenesis" includes the process by which an embryo, e.g., a parasitic embryo, is formed and develops, e.g., in a parasite. Without being bound by theory, in one embodiment, the compounds of formula I, Ia, Ib, II, IIa, IIb, IIc, III, IV, V, VI, VIa, VIb, VII, VIIa, VIIb, VIIc, VIId, VIIe, VIIf or a compound of Table 1 or 2 modulate, e.g., inhibit, the binding of RNA binding proteins required in the early stages of embryogenesis to a target RNA of the RNA binding protein. In one embodiment, the RNA binding protein is MEX-5, POS-1 or MEX-3.

The term "RNA binding protein," as used herein, refers to a protein that selectively or specifically binds to RNA. In one embodiment, the RNA binding protein binds selectively to single-stranded RNA. In one embodiment, the RNA binding protein binds selectively to double-stranded RNA. An RNA binding protein of the present invention selectively or specifically binds to a target RNA, e.g., RNA that comprises an RNA binding recognition element for the RNA binding protein.

In one embodiment, the RNA binding protein is required for embryogenesis, e.g., parasitic embryogenesis (e.g., helminth embryogenesis). In one embodiment, the RNA binding protein is a helminth RNA binding protein, e.g., a nematode RNA binding protein, a trematode RNA binding protein or a cestode RNA binding protein. In one embodiment, the RNA binding protein is a mammalian RNA binding protein. In one embodiment, the RNA binding protein is a mammalian RNA binding protein and is not required for embryogenesis. In one embodiment of the invention, the RNA binding protein comprises a CCCH Zinc finger motif. Examples of RNA binding proteins that comprise a CCCH Zinc finger motif include, but are not limited to, MEX-5, POS-1 and MEX-6 or a homolog thereof. In another embodiment, the RNA binding protein comprises a KH domain. Examples of RNA binding proteins that comprise a KH domain include, but are not limited to, MEX-3 and GLD-1, or a homolog thereof.

The term "MEX-5" includes a cytoplasmic RNA binding protein that contains two CCCH zinc finger motifs that functions along with the similar CCCH zinc finger protein MEX-6, and is necessary for transducing polarity cues and establishing soma/germline asymmetry in the early embryo. In regulating the soma/germline asymmetry, MEX-5 activates the SOCS-box protein ZIF-1, which functions as part of an E3 ubiquitin ligase complex that degrades germ plasm proteins in somatic blastomers, resulting in reduced expression of germline proteins in germline blastomers. MEX-5 is expressed at uniform levels in both oocytes and newly fertilized eggs (see Schubert C. M. et al., *Molecular Cell* (2000) 5:671-682; Hunter, C. et al. *Development* (2002) 129:747-759; Cuenca, A. A. et al. (2003) *Development* 130:1255-1265; Lin *Developmental Biology* (2003) 258:226-239; DeRenzo C. et al., (2003) *Nature* 424:685-689; Nishi et al. (2008) *Development* 135:687-697).

The term "POS-1" includes a CCCH-type zinc finger protein that is necessary for the proper fate specification of germ cells, intestine, pharynx and hypodermis. POS-1 is also required in posterior blastomers for positive regulation of apx-1 mRNA translation and negative regulation of glp-1 mRNA translation by direct binding to the spatial control region in the glp-1 mRNA 3' UTR. POS-1 is first found in low levels in one-cell embryos and in high levels in germline blastomeres, where it disappears after the P4 division. POS-1 colocalizes with cytoplasmic and perinuclear P granules in the germline blastomeres P1, P2, P3 and P4 (see Kohara, Y. et al. (1999) *Development* 126:1-11; Oguro, K. et al. (2003) *Development* 130:2495-2503).

The term "MEX-3" includes a KH domain-containing RNA binding protein that is necessary for specifying the identities of the anterior AB blastomer and its descendent, as well as for the identity of the P3 blastomer and proper segregation of the germline P granules. MEX-3 is found uniformly in the cytoplasm of oocytes and one-cell stage embryos and becomes more abundant in AB and its daughters at the two and four cell stages (see Bowerman et al. (1996) *Cell* 87:205-216).

In one embodiment, the RNA binding modulatory compounds of the invention, e.g., the compounds of formula I, Ia, Ib, II, IIa, IIb, IIc, III, IV, V, VI, VIa, VIb, VII, VIIa, VIIb, VIIc, VIId, VIIe, VIIf or a compound of Table 1 or 2, modulate (e.g., inhibit) the RNA binding activity of MEX-5, but do not substantially inhibit the RNA binding activity of MEX-3 or POS-1. In another embodiment, the RNA binding modulatory compounds of the invention, e.g., the compounds of formula I, Ia, Ib, II, IIa, IIb, IIc, III, IV, V, VI, VIa, VIb, VII, VIIa, VIIb, VIIc, VIId, VIIe, VIIf or a compound of Table 1 or 2, modulate (e.g., inhibit) the RNA binding activity of MEX-3, but do not substantially inhibit the RNA binding activity of MEX-5 or POS-1. In yet another embodiment, the RNA binding modulatory compounds of the invention, e.g., the compounds of formula I, Ia, Ib, II, IIa, IIb, IIc, III, IV, V, VI, VIa, VIb, VII, VIIa, VIIb, VIIc, VIId, VIIe, VIIf or a compound of Table 1 or 2, modulate (e.g., inhibit) the RNA binding activity of POS-1, but do not substantially inhibit the RNA binding activity of MEX-3 or MEX-5. In a further embodiment, the RNA binding modulatory compounds of the invention, e.g., the compounds of formula I, Ia, Ib, II, IIa, IIb, IIc, III, IV, V, VI, VIa, VIb, VII, VIIa, VIIb, VIIc, VIId, VIIe, VIIf or a compound of Table 1 or 2 modulate (e.g., inhibit) the RNA binding activity of two of MEX-3, MEX-5 and POS-1, without substantially modulating (e.g., inhibiting) the RNA binding activity of the third protein. In one embodiment, the RNA binding modulatory compounds of the invention, e.g., the compounds of formula I, Ia, Ib, II, IIa, IIb, IIc, III, IV, V, VI, VIa, VIb, VII, VIIa, VIIb, VIIc, VIId, VIIe, VIIf or a compound of Table 1 or 2, modulate (e.g., inhibit) the RNA binding activity of MEX-3, MEX-5 and POS-1. In one embodiment, the RNA binding modulatory compounds of the invention, e.g., the compounds of formula I, Ia, Ib, II, IIa, IIb, IIc, III, IV, V, VI, VIa, VIb, VII, VIIa, VIIb, VIIc, VIId, VIIe, VIIf or a compound of Table 1 or 2, modulate (e.g., inhibit) the RNA binding activity of parasitic MEX-3, MEX-5 and/or POS-1 without modulating (e.g., inhibiting) the RNA binding of the mammalian (e.g., human) homologs of MEX-3, MEX-5 and/or POS-1.

In one embodiment, an RNA binding modulatory compound of the invention, e.g., a compound of formula I, Ia, Ib, II, IIa, IIb, IIc, III, IV, V, VI, VIa, VIb, VII, VIIa, VIIb, VIIc, VIId, VIIe, VIIf or a compound of Table 1 or 2, modulates, e.g., inhibits, the RNA binding activity of an RNA binding protein (e.g., MEX-3, MEX-5 and/or POS-1) by at least about 75%, by about 76%, by about 77%, by about 78%, by about 79%, by about 80%, by about 81%, by about 82%, by about 83%, by about 84%, by about 85%, by about 86%, by about 87%, by about 88%, by about 89%, by about 90%, by about 91%, by about 92%, by about 93%, by about 94%, by about 95%, by about 96%, by about 97%, by about 98%, by about 99% or by about 100%. In one embodiment, an RNA binding modulatory compound of the invention, e.g., a compound of formula I, Ia, Ib, II, IIa, IIb, IIc, III, IV, V, VI, VIa, VIb, VII, VIIa, VIIb, VIIc, VIId, VIIe, VIIf or a compound of Table 1 or 2, modulates, e.g., inhibits, the RNA binding activity of an RNA binding protein (e.g., MEX-3, MEX-5 and/or POS-1) by about 25%, by about 30%, by about 35%, by about 45%, by about 50%, by about 55%, by about 60%, by about 65%, by about 70%, by about 71%, by about 72%, by about 73%, or by about 74%. In a preferred embodiment, an RNA binding modulatory compound of the invention, e.g., a compound of formula I, Ia, Ib, II, IIa, IIb, IIc, III, IV, V, VI, VIa, VIb, VII, VIIa, VIIb, VIIc, VIId, VIIe, VIIf or a compound of Table 1 or 2, modulates, e.g., inhibits, the RNA binding activity of an RNA binding protein (e.g., MEX-3, MEX-5 and/or POS-1) by at least about 75%.

In a further embodiment, the invention pertains, at least in part to a method for reducing parasitic burden in soil, in plants or in a subject suffering from a parasitic infection by administering a therapeutically or pesticidally effective amount of an RNA binding modulatory compound, e.g., a compound of formula I, Ia, Ib, II, IIa, IIb, IIc, III, IV, V, VI, VIa, VIb, VII, VIIa, VIIb, VIIc, VIId, VIIe, VIIf or a compound of Table 1 or 2, such that the parasitic burden is reduced.

The term "parasitic burden" includes the amount (number) of parasites and/or parasite eggs present in a given sample. Appropriate samples include, but are not limited to, soil samples, plant samples (e.g., from roots, leaves, stems and the like) and biological samples (e.g., urine, blood, tissue, fecal matter and the like). In one embodiment, upon administration of an RNA binding modulatory compound, e.g., a compound of formula I, Ia, Ib, II, IIa, IIb, IIc, III, IV, V, VI, VIa, VIb, VII, VIIa, VIIb, VIIc, VIId, VIIe, VIIf or a compound of Table 1 or 2, to the subject, the parasitic burden in that subject is reduced by about 10%, by about 11%, by about 12%, by about 13%, by about 14%, by about 15%, by about 16%, by about 17%, by about 18%, by about 19%, by about 20%, by about 21%, by about 22%, by about 23%, by about 24%, by about 25%, by about 26%, by about 27%, by about 28%, by about 29%, by about 30%, by about 31%, by about 32%, by about 33%, by about 34%, by about 35%, by about 36%, by about 37%, by about 38%, by about 39%, by about 40%, by about 41%, by about 32%, by about 43%, by about 44%, by about 45%, by about 46%, by about 47%, by about 48%, by about 49%, 50%, by about 51%, by about 52%, by about 53%, by about 54%, by about 55%, by about 56%, by about 57%, by about 58%, by about 59%, by about 60%, by about 61%, by about 62%, by about 63%, by about 64%, by about 65%, by about 66%, by about 67%, by about 68%, by about 69%, by about 70%, by about 71%, by about 72%, by about 73%, by about 74%, by about 75%, by about 76%, by about 77%, by about 78%, by about 79%, by about 80%, by about 81%, by about 82%, by about 83%, by about 84%, by about 85%, by about 86%, by about 87%, by about 88%, by about 89%, by about 90%, by about 91%, by about 92%, by about 93%, by about 94%, by about 95%, by about 96%, by about 97%, by about 98%, by about 99% or by about 100%.

In one embodiment, the invention pertains, at least in part, to a method for treating or preventing an autoimmune disorder or inflammatory disorder in a subject by administering to the subject a therapeutically effective amount of an RNA binding modulatory compound, e.g., a compound of formula I, Ia, Ib, II, IIa, IIb, IIc, III, IV, V, VI, VIa, VIb, VII, VIIa, VIIb, VIIc, VIId, VIIe, VIIf or a compound of Table 1 or 2, such that the inflammatory disorder is treated.

The term "inflammatory disorder" includes those disorders that are associated with acute or chronic inflammation. Examples of inflammatory disorders include, but are not limited to, allergic reactions, autoimmune disorders (e.g., multiple sclerosis, diabetes, e.g., insulin dependent diabetes mellitus, chronic obstructive pulmonary disease, lupus, endometriosis, myasthenia gravis, psoriasis, psoriatic arthritis), cancer, atherosclerosis, ischemic heart disease, asthma, autoimmune diseases, chronic inflammation, chronic prostatitis, glomerulonephritis, inflammatory bowel disease, pelvic inflammatory disease, e.g., Crohn's disease, reperfusion injury, rheumatoid arthritis, ankylosing spondylitis, transplant rejection and vasculitis.

In another embodiment, the invention pertains, at least in part, to a method for treating a disease caused by a parasitic infestation in a mammal by administering to the mammal a therapeutically effective amount of an RNA binding modulatory compound, e.g., a compound of formula I, Ia, Ib, II, IIa, IIb, IIc, III, IV, V, VI, VIa, VIb, VII, VIIa, VIIb, VIIc, VIId, VIIe, VIIf or a compound of Table 1 or 2, such that the disease is treated.

In one embodiment, the disease caused by a parasitic infestation is helminthiasis. The term "helminthiasis" includes diseases caused by the infestation of a mammal by the a helminth (e.g., a plathyhelminth, for example, trematodes and cestodes; thorny-headed worms, for example, acanthocephalans; and roundworms, for example, nematodes). Examples of heminthiasis include, but are not limited to, schistosomiasis, swimmer's itch, clonorchiasis, fasciolosis, paragonimiasis, fasciolopsiasis, echinococcosis, taeniasis, cysticercosis, hymenolepiasis, diphyllobothriasis, sparganosis, dracunculiasis, onchocerciasis, loa loa filariasis, mansonelliasis, dirofilariasis, gnathostomiasis, ancylostomiasis, cutaneous larva migrans, necatoriasis, angiostrongyliasis, ascariasis, anisakiasis, viceral larva migrans, toxocariasis, strongyloidiasis, enterobiasis, pinworm, trichinosis, trichuriasis, whipworm and capillariasis.

The articles "a" and "an" are used herein to refer to one or to more than one (i.e. to at least one) of the grammatical object of the article. By way of example, "an element" means one element or more than one element.

As used herein, the term "compound" or "test compound" includes any agent, e.g., nucleic acid molecules, antisense nucleic acid molecule, peptide, peptidomimetic, small molecule, or other drug, which binds to an RNA-binding protein, modulates, e.g., inhibits, interaction of an RNA-binding protein and an RNA molecule comprising an RNA-binding protein recognition element, and/or has a stimulatory or inhibitory effect on, for example, RNA-binding protein expression or activity, binding affinity or stability.

For screening assays of the invention, preferably, the "test compound or agent" screened includes molecules that are not known in the art to modulate activity of an RNA-binding protein and/or expression as described herein. Preferably, a plurality of agents are tested using the instant methods.

The term "library of test compounds" is intended to refer to a panel comprising a multiplicity of test compounds.

In one embodiment, the agent or test compound is a compound that directly interacts with the RNA-binding protein or directly interacts with a molecule with which the RNA-binding protein interacts (e.g., a compound that inhibits or stimulates the interaction between the RNA-binding protein and the RNA-binding protein target molecule, e.g., an RNA molecule comprising an RNA-binding protein recognition element). In another embodiment, the compound is one that indirectly modulates expression and/or activity of an RNA-binding protein, e.g., by modulating the activity of a molecule that is upstream or downstream of the RNA-binding protein in a signal transduction pathway involving the RNA-binding protein. Such compounds can be identified using screening assays that select for such compounds, as described in detail below.

The term "interact" as used herein is meant to include detectable interactions between molecules, such as can be detected using, for example, a gel shift assay, a fluorescence polarization assay, a yeast two hybrid assay, and coimmunoprecipitation. The term interact is also meant to include "binding" interactions between molecules. Interactions may be protein-protein or protein-nucleic acid in nature.

As used herein, the term "contacting" (e.g., contacting a cell with a compound) is intended to include incubating the compound and the cell together in vitro (e.g., adding the compound to cells in culture) or administering the compound to a subject such that the compound and cells of the subject are contacted in vivo.

As used herein, the term "indicator composition" refers to a composition that includes a protein of interest (e.g., an RNA-binding protein), for example, a cell that naturally expresses the protein, a cell that has been engineered to express the protein by introducing an expression vector encoding the protein into the cell, or a cell free composition that contains the protein (e.g., purified naturally-occurring protein or recombinantly-engineered protein).

As used herein, the term "cell free composition" refers to an isolated composition which does not contain intact cells. Examples of cell free compositions include cell extracts and compositions containing isolated proteins.

In one embodiment, small molecules can be used as test compounds. The term "small molecule" is a term of the art and includes molecules that are less than about 7500, less than about 5000, less than about 1000 molecular weight or less than about 500 molecular weight. In one embodiment, small molecules do not exclusively comprise peptide bonds. In another embodiment, small molecules are not oligomeric. Exemplary small molecule compounds which can be screened for activity include, but are not limited to, peptides, peptidomimetics, nucleic acids, carbohydrates, small organic molecules (e.g., Cane et al. 1998. Science 282:63), and natural product extract libraries. In another embodiment, the compounds are small, organic non-peptidic compounds. In a further embodiment, a small molecule is not biosynthetic. For example, a small molecule is preferably not itself the product of transcription or translation.

I. RNA Binding Modulatory Compounds

In one embodiment, the RNA binding modulatory compound is a compound of formula I:

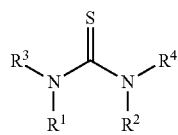

(I)

wherein

R¹, R², R³ and R⁴ are each independently hydrogen, hydroxyl, alkyl, alkenyl, alkynyl, aryl, amino, sulfonyl, carbonyl, carboxylate, alkoxy, aryloxy, carbonyloxy, acyl or a heterocyclic moiety; or R¹ and R³ and/or R² and R⁴ together with the nitrogen atom to which they are attached are linked to form a 3-9-membered carbocyclic or heterocyclic ring or 5-9-membered aryl ring; and pharmaceutically acceptable salts thereof.

In one embodiment, R¹ and R² are each hydrogen and R³ is aryl, for example, phenyl or a thiophenyl moiety. In another embodiment, the phenyl is a mono- or di-substituted phenyl, substituted with, for example, carboxylate, halogen (e.g., chlorine), alkyl (e.g., methyl) or amino (e.g., carbonylamino, for example, alkylcarbonylamino, such as CH₃(CH₂)₃CONH—). In yet another embodiment, the phenyl is selected from the group consisting of:

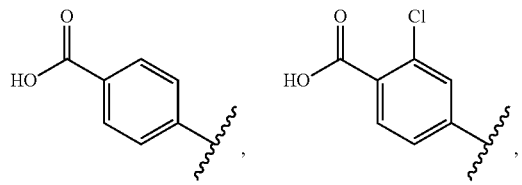

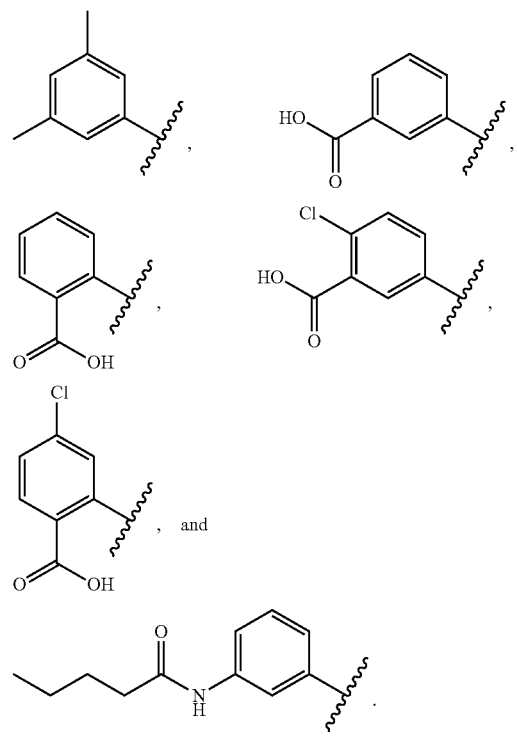

, and

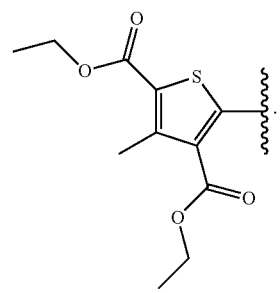 [SMILES: *c1sc(C(=O)OCC)c(C)c1C(=O)OCC]

In a further embodiment, the thiophenyl moiety is carbonyl substituted with, for example, alkoxy (e.g., ethoxy) and alkyl (e.g., methyl). In one embodiment, the thiophenyl moiety is

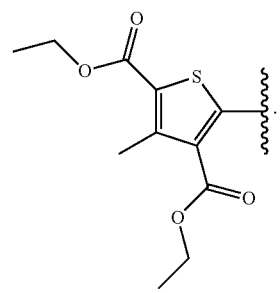 [SMILES: *c1sc(C(=O)OCC)c(C)c1C(=O)OCC]

In one embodiment, R⁴ is carbonyl substituted with an aryl moiety, such as phenyl (e.g., mono-, di- or tri-substituted), for example, phenyl substituted with halogen (e.g., chlorine, bromine or iodine), alkoxy (e.g., methoxy or ethoxy), nitro, aryl (e.g., phenyl) or alkyl (e.g., methyl). In another embodiment, the phenyl is selected from the group consisting of:

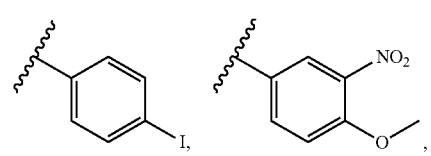

-continued

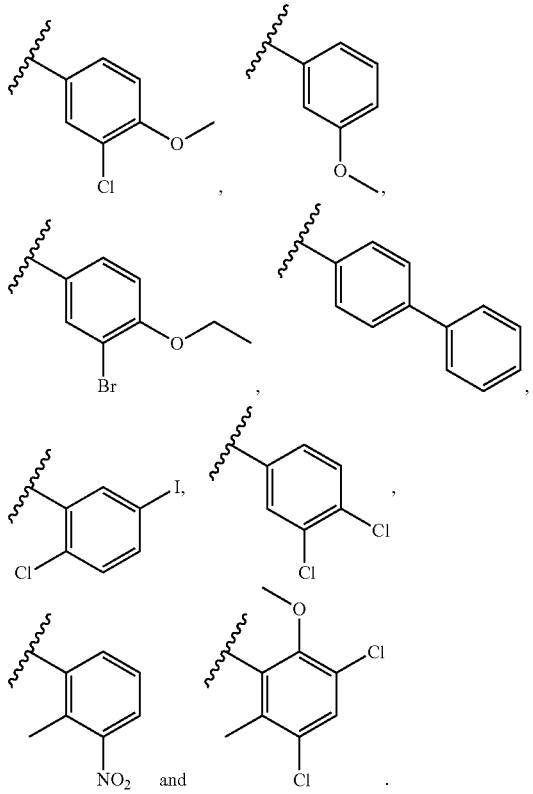

In yet another embodiment, R⁴ is carbonyl substituted with an aryl moiety, such as naphthyl, for example, an alkoxy (e.g., methoxy) substituted naphthyl. In one embodiment, the napthyl moiety is

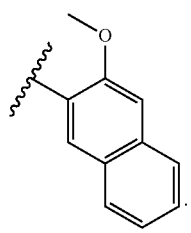

In one embodiment, R⁴ is carbonyl substituted, for example, with an aryl moiety, such as a heteroaryl moiety, such as, a furanyl or benzothiophenyl moiety. In another embodiment, the furanyl moiety is substituted with aryl, for example, phenyl, such as phenyl substituted with halogen (e.g., chlorine). In yet another embodiment, the furanyl moiety is

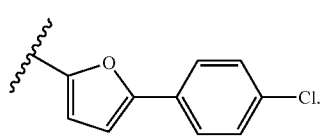 [SMILES: *c1ccc(-c2ccc(Cl)cc2)o1]

In a further embodiment, the benzothiophenyl moiety is substituted with halogen (e.g., chlorine). In yet another embodiment, the benzothiophenyl moiety is

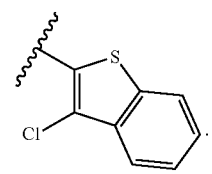 [SMILES: *c1sc2ccccc2c1Cl]

In yet another embodiment, R⁴ is carbonyl, for example, carbonyl substituted with alkyl (e.g., isopropyl).

In one embodiment, R¹ and R³ are each alkyl, for example, aryl substituted alkyl, such as benzyl.

In a further embodiment, R² is hydrogen and R⁴ is carbonyl, for example, carbonyl substituted with aryl, such as phenyl (e.g., —NO₂ substituted phenyl, for example,

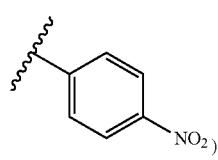

or a furanyl moiety, such as a furanyl moiety substituted with halogen (e.g., bromine), for example,

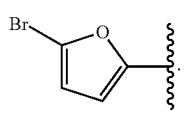

In yet another embodiment, R⁴ is a benzo[d]imidazole moiety, for example, 1-alkyl-1H-benzo[d]imidazole, such as 1-propyl-1H-benzo[d]imidazole, 1-butyl-1H-benzo[d]imidazole or 1-benzyl-1H-benzo[d]imidazole.

In another embodiment, R¹ is hydrogen and R³ is aryl (e.g., a diphenylquinoxalinyl moiety, for example,

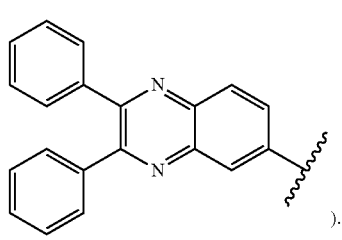 [SMILES: *c1ccc2nc(-c3ccccc3)c(-c3ccccc3)nc2c1]

In one embodiment, R² and R⁴ together with the nitrogen atom to which they are attached are linked to form a 3-9 membered heterocyclic ring, such as a piperazinyl ring, for example, a piperazinyl ring substituted with a carbonyl moiety (e.g., carbonyl substituted with alkoxy, such as carbonyl substituted with ethoxy). In another embodiment, the piperazinyl ring is

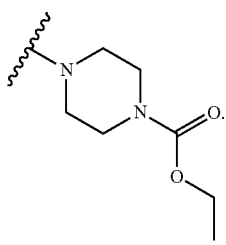 [SMILES: *N1CCN(C(=O)OCC)CC1]

In a further embodiment, R³ is sulfonyl (e.g., tosylate).

In yet another embodiment, R⁴ is alkyl, for example, aryl substituted alkyl, such as an oxydibenzene moiety, including, but not limited to,

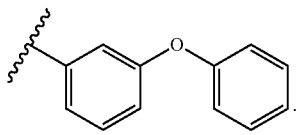 [SMILES: *c1cccc(Oc2ccccc2)c1]

In another embodiment, the RNA binding modulatory compound of formula I is a compound of formula Ia:

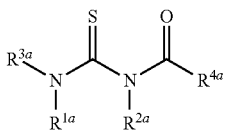

(Ia)

wherein $R^{1a}$ and $R^{2a}$ are each independently hydrogen or alkyl; and $R^{3a}$ and $R^{4a}$ are each independently alkyl or aryl, and pharmaceutically acceptable salts thereof.

In one embodiment, $R^{1a}$ and $R^{2a}$ are each hydrogen and $R^{3a}$ is aryl, such as phenyl or a thiophenyl moiety. In another embodiment, the phenyl is a mono- or di-substituted phenyl, substituted with, for example, carboxylate, halogen (e.g., chlorine), alkyl (e.g., methyl) or amino (e.g., amino substituted with carbonyl, which may be further substituted with alkyl, for example, CH₃(CH₂)₃CONH—). In a further embodiment, the thiophenyl moiety may be substituted with carbonyl (e.g., carbonyl substituted with alkoxy, such as carbonyl substituted with ethoxy) and alkyl (e.g., methyl).

In another embodiment, $R^{1a}$ and $R^{3a}$ are each alkyl, for example, alkyl substituted with aryl (e.g., phenyl), such as benzyl.

In yet another embodiment, $R^{3a}$ is selected from the group consisting of:

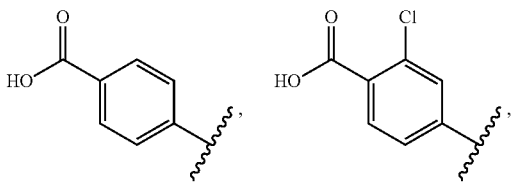

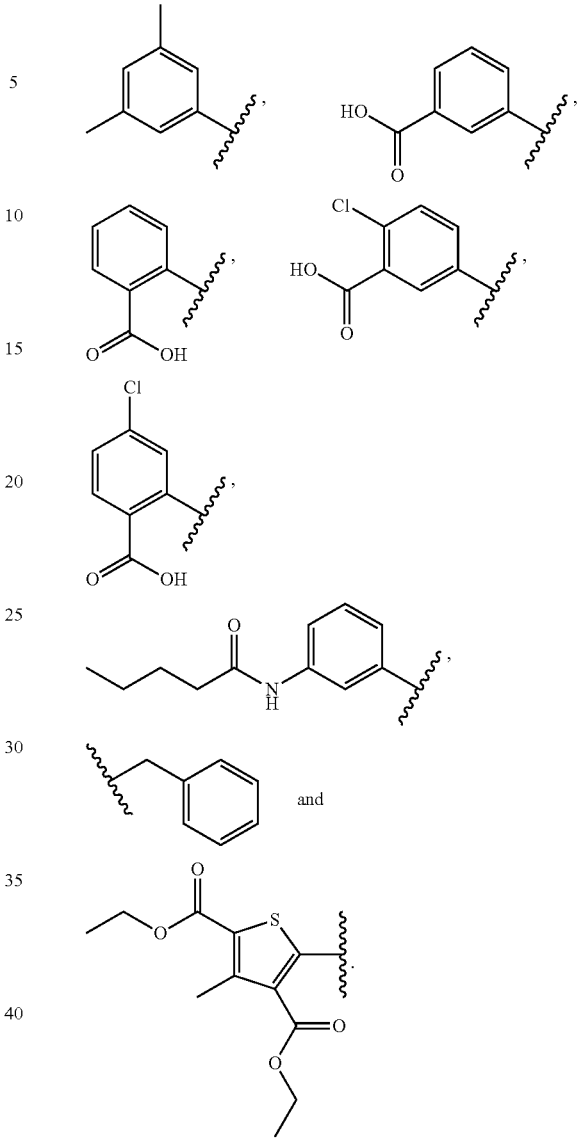

In one embodiment, $R^{4a}$ is an aryl moiety, for example, phenyl (e.g., a mono-, di- or tri-substituted), such as phenyl substituted with halogen (e.g., chlorine, bromine or iodine), alkoxy (e.g., methoxy or ethoxy), nitro, aryl (e.g., phenyl) or alkyl (e.g., methyl).

In another embodiment, $R^{4a}$ is aryl, for example, naphthyl, such as a naphthyl substituted with alkoxy (e.g., methoxy).

In yet another embodiment, $R^{4a}$ is an aryl moiety, such as a heteroaryl moiety, for example, a furanyl or benzothiophenyl moiety. In another embodiment, the furanyl moiety is substituted with aryl, for example, phenyl, such as phenyl substituted with halogen (e.g., chlorine). In a further embodiment, the benzothiophenyl moiety is substituted with halogen (e.g., chlorine).

In yet another embodiment, $R^{4a}$ is alkyl (e.g., isopropyl).

In one embodiment, $R^{4a}$ is selected from the group consisting of:

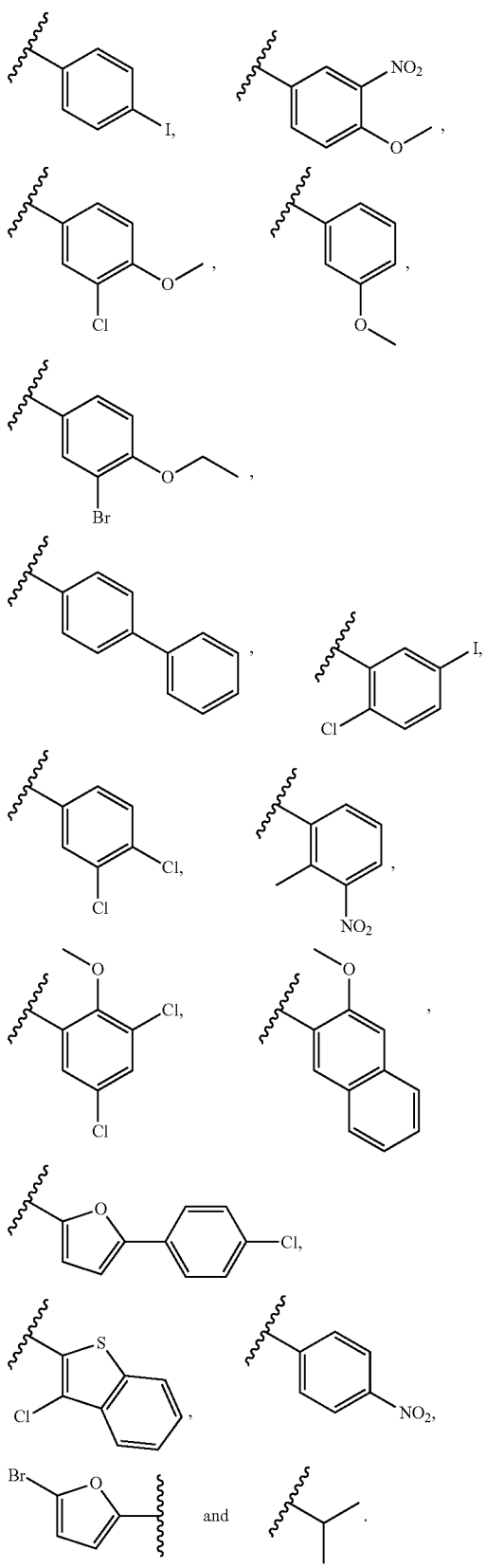

In one embodiment, the RNA binding modulatory compound of formula I is a compound of formula Ib:

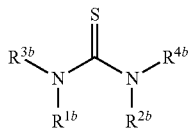

wherein
$R^{1b}$ and $R^{2b}$ are each hydrogen;
$R^{3b}$ is aryl or sulfonyl; and
$R^{4b}$ is alkyl or aryl; or $R^{2b}$ and $R^{4b}$ together with the nitrogen to which they are attached are linked to form a 3-9-membered heterocyclic or 5-9-membered aryl ring; and pharmaceutically acceptable salts thereof.

In one embodiment, $R^{1b}$ and $R^{2b}$ are each hydrogen, $R^{3b}$ is a sulfonyl (e.g., aryl substituted sulfonyl, for example, tosylate), and $R^{4b}$ is aryl (e.g., an oxydibenzene moiety, for example,

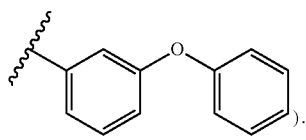 [SMILES: *c1cccc(Oc2ccccc2)c1]).

In another embodiment, $R^{1b}$ and $R^{2b}$ are each hydrogen, $R^{3b}$ is aryl (e.g., phenyl) and $R^{4b}$ is aryl, for example, heteroaryl, such as a benzo[d]imidazole moiety (e.g., 1-alkyl-1H-benzo[d]imidazole, for example, 1-propyl-1H-benzo[d]imidazole, 1-butyl-1H-benzo[d]imidazole or 1-benzyl-1H-benzo[d]imidazole).

In a further embodiment, $R^{1a}$ is hydrogen, $R^{3b}$ is aryl, for example, a diphenylquinoxalinyl moiety ( e.g., 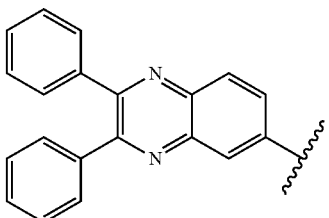 )

and $R^{2b}$ and $R^{4b}$ together with the nitrogen to which they are attached are linked to form a 3-9 membered heterocyclic ring, for example, a piperazinyl ring, such as a piperazinyl ring substituted with carbonyl (e.g., carbonyl substituted with alkoxy, for example, carbonyl substituted with ethoxy).

In yet another embodiment, the compound of formula I is a compound selected from the group consisting of:

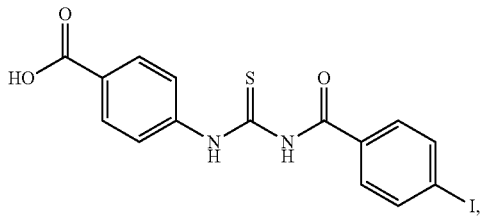

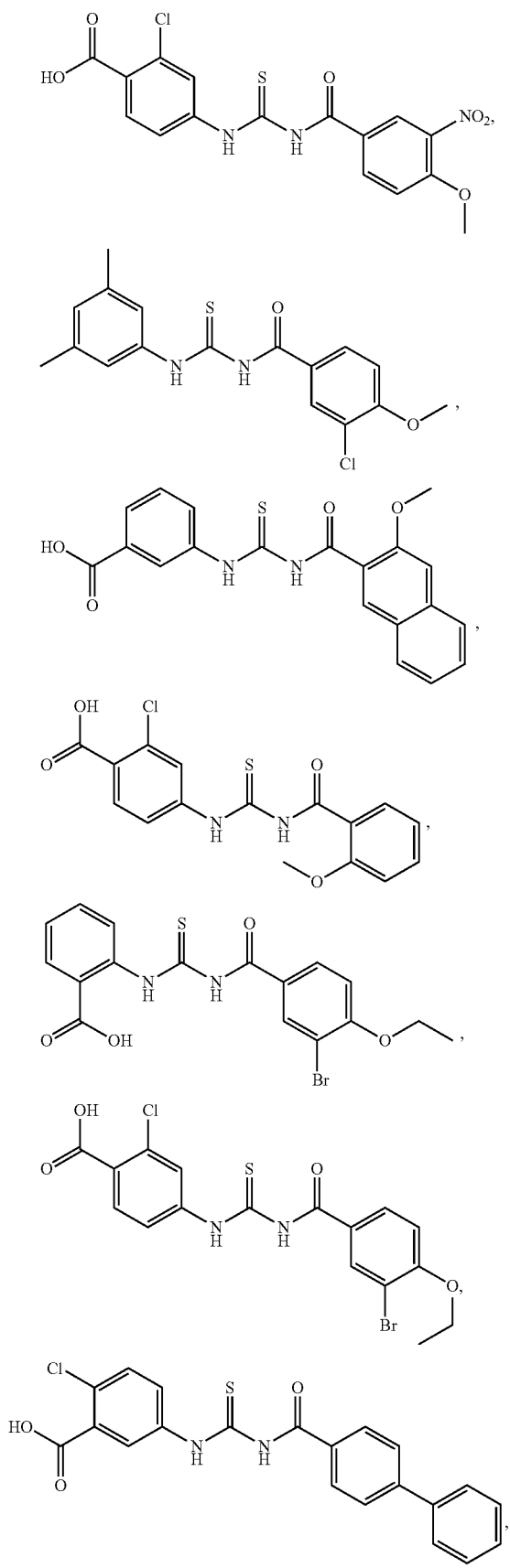
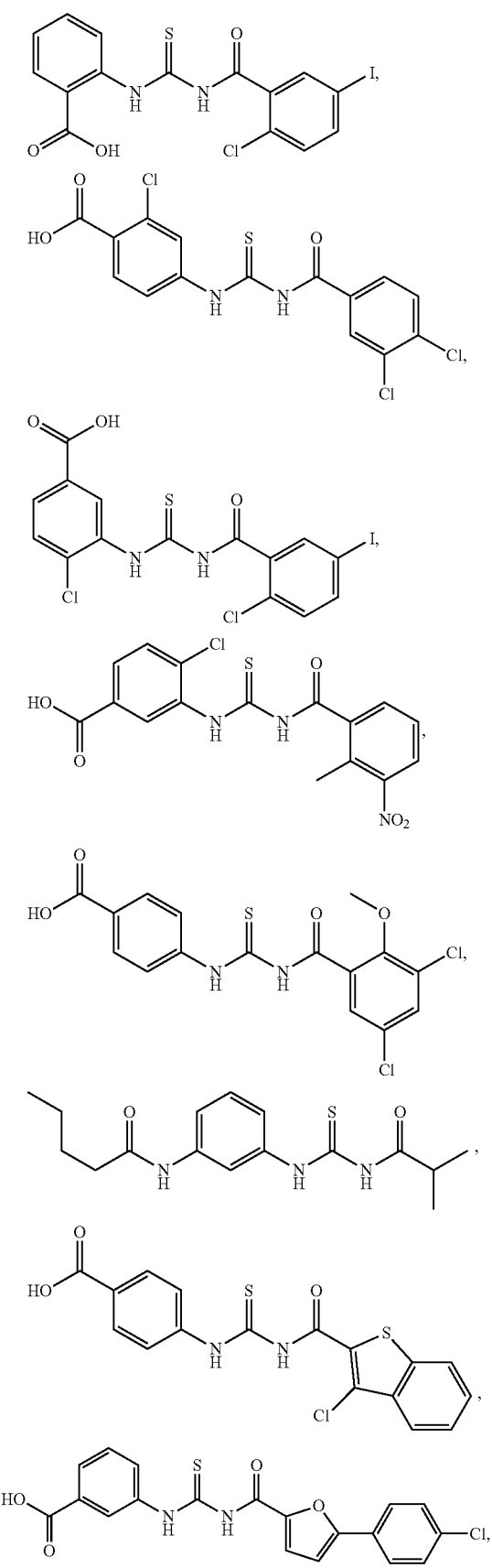

-continued

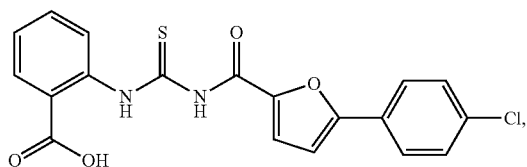
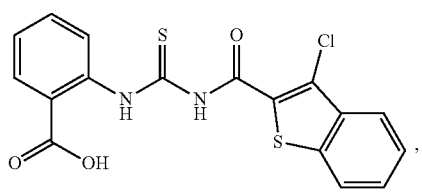
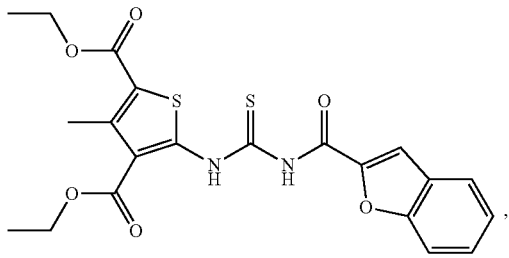
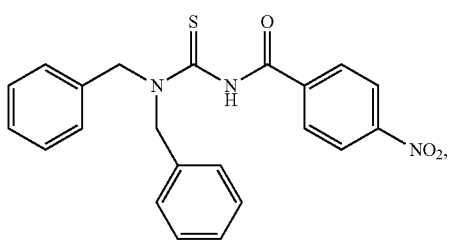
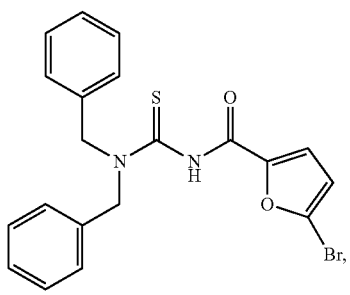
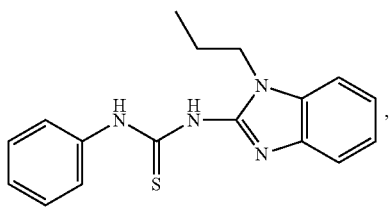
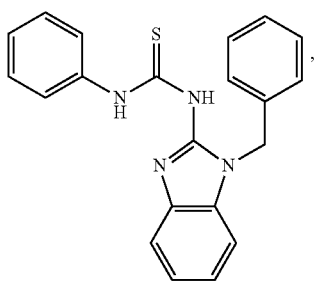

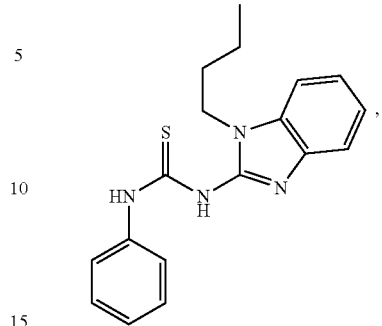
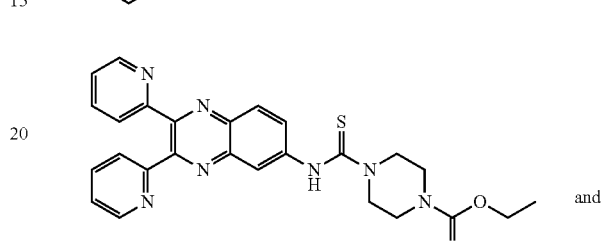

and

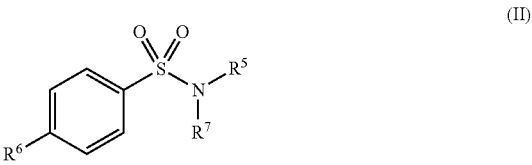

and pharmaceutically acceptable salts thereof.

In another embodiment, the RNA binding modulatory compound is a compound of formula II:

$$(II)$$

wherein $R^5$ and $R^7$ are each hydrogen, hydroxyl, alkyl, alkenyl, alkynyl, aryl, amino, sulfonyl, carbonyl, carboxylate, alkoxy, aryloxy, carbonyloxy, acyl or a heterocyclic moiety;

$R^6$ is hydrogen, hydroxyl, alkyl, alkenyl, alkynyl, aryl, amino, sulfone, carbonyl, carboxylate, alkoxy, aryloxy, carbonyloxy, halogen, acyl, oximyl, hydrazinyl, —NO$_2$, —CN, a heterocyclic moiety or thioether; and pharmaceutically acceptable salts thereof.

In one embodiment, $R^7$ is aryl, for example, phenyl, such as phenyl substituted with halogen (e.g., bromine); $R^6$ is hydrogen and $R^5$ is alkyl, such as aminocarbonylalkyl, which may be substituted, for example, aryl (e.g., phenyl, including, but not limited to, phenyl substituted with aminocarbonyl. In one embodiment, $R^5$ is

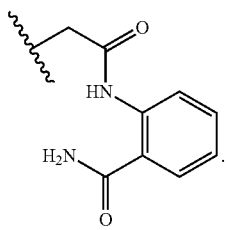 [SMILES: *CC(=O)Nc1ccccc1C(N)=O]

In another embodiment, $R^7$ is hydrogen; $R^5$ is aryl, for example, phenyl (e.g., disubstituted phenyl), for example, phenyl substituted with hydroxyl, halogen (e.g., chlorine), alkyl (e.g., methyl) or amino (e.g., aryl substituted sulfonylamino, for example, phenyl substituted sulfonylamino). In one embodiment, $R^5$ is selected from the group consisting of:

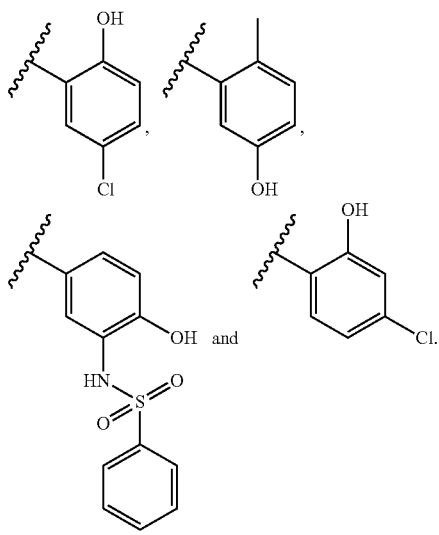

In a further embodiment, $R^6$ is —$NO_2$ or hydrogen.

In yet another embodiment, $R^7$ is hydrogen; $R^5$ is aryl, for example, heteroaryl, such as an oxazolyl moiety

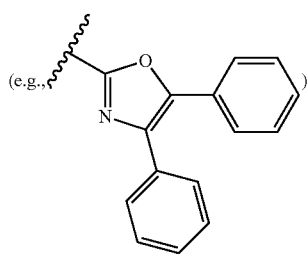 [SMILES: *c1nc(-c2ccccc2)c(-c2ccccc2)o1]

and $R^6$ is halogen (e.g., chlorine).

In a further embodiment, $R^7$ is hydrogen; $R^5$ is alkyl, for example, heteroaryl substituted alkyl in which the heteroaryl may be a benzo[d]imidazole moiety, (e.g., a 1[H]-benzo[d] imidazole) and $R^6$ is alkyl (e.g., methyl) or halogen (e.g., chlorine).

In yet another embodiment, $R^7$ is hydrogen; $R^5$ is heteroaryl, for example, isoxazolyl, thiazolyl, thiadiazolyl or pyrimidinyl such as

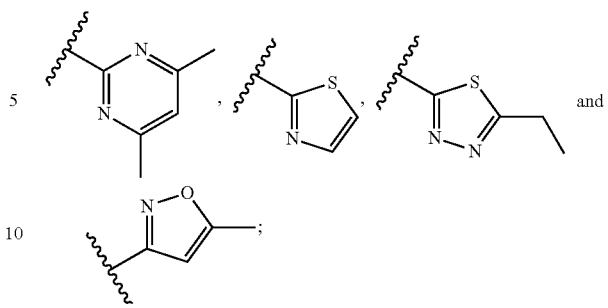

$R^6$ is amino, for example, amino substituted with sulfonyl, for example, sulfonyl substituted with aryl in which the aryl may be substituted with halogen (e.g., bromine); aryl, for example, phenyl, such as trisubstituted phenyl substituted with halogen (e.g., chlorine) and hydroxyl; heteroaryl, for example, thiazolyl, which may be substituted with aryl, such as phenyl, for example, phenyl substituted with hydroxyl, alkyl (e.g., methyl) or halogen (e.g., fluorine). In another embodiment, $R^6$ is selected from the group consisting of:

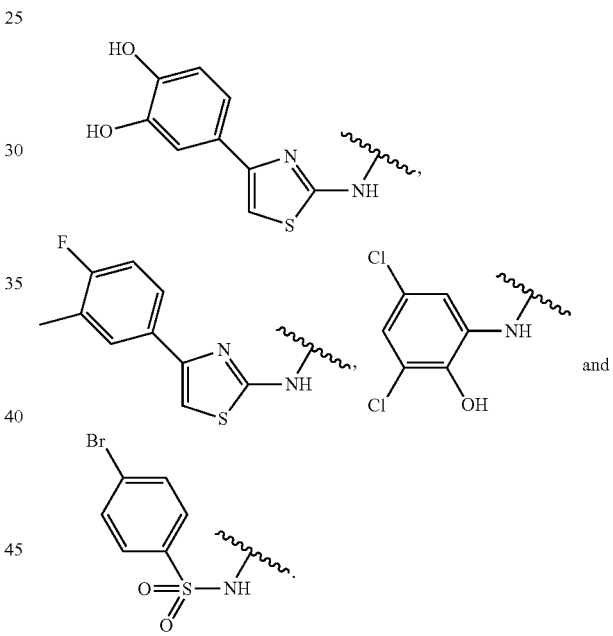

In yet another embodiment, $R^7$ is hydrogen; $R^5$ is aryl, for example, heteroaryl (e.g., isoxazolyl, thiazolyl or thiadiazolyl, such as

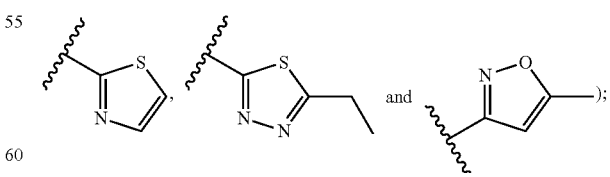

and $R^6$ is amino, for example, carbonylamino, such as carbonylamino substituted with alkyl. In one embodiment, the alkyl is $C_1$-$C_6$ alkyl that may be substituted with thiol, for example heteroaryl (e.g., benzothiazolyl or triazinyl) substituted thiol; aryloxy, for example, phenoxy, such as di- or trisubstituted phenoxy substituted with alkyl (e.g., methyl) or halogen (e.g., bromine); a heterocyclic moiety (e.g., quinazolinonyl) or aryl, for example, phenyl, such as phenyl substituted with alkyl (e.g., methyl).

In yet another embodiment, $R^7$ is hydrogen; $R^5$ is aryl, for example heteroaryl (e.g., isoxazolyl, thiazolyl or thiadiazolyl, such as

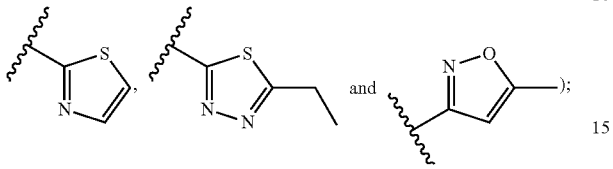

and $R^6$ is amino, for example carbonylamino, such as carbonylamino substituted with aryl, for example, phenyl (e.g., mono- or di-substituted phenyl), such as phenyl substituted with alkyl (e.g., t-butyl), alkoxy (e.g., methoxy or n-butoxy) or halogen (e.g., chlorine or bromine).

In another embodiment, $R^7$ is hydrogen; $R^5$ is aryl, for example heteroaryl (e.g., isoxazolyl, thiazolyl or thiadiazolyl, such as

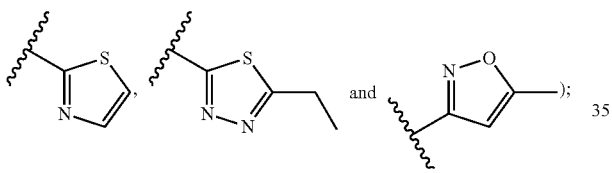

and $R^6$ is amino, for example, carbonylamino, such as carbonylamino substituted with a heterocyclic moiety (e.g., chromene or pyrrolidinone).

In a further embodiment, $R^6$ is selected from the group consisting of:

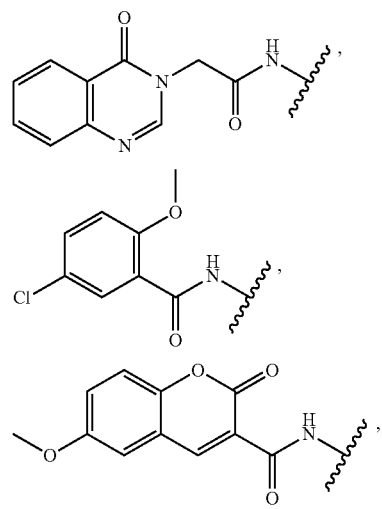

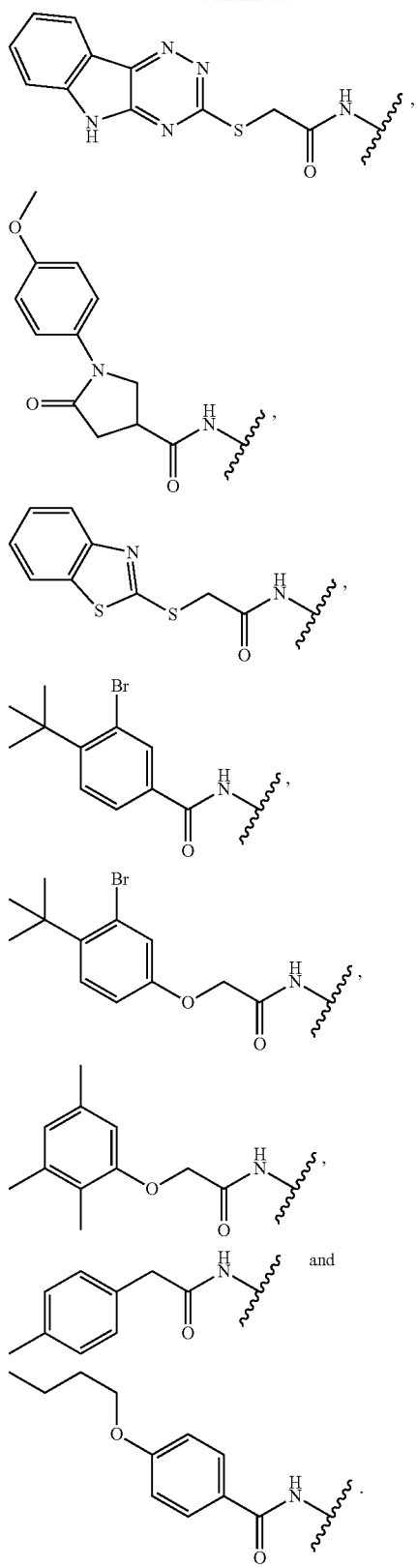

In one embodiment, the RNA binding modulatory compound of formula II is a compound of formula IIa:

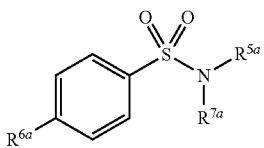
(IIa)

wherein $R^{5a}$ is alkyl or aryl;

$R^{6a}$ is —$NO_2$, alkyl, halogen or hydrogen; and $R^{7a}$ is hydrogen or aryl, and pharmaceutically acceptable salts thereof.

In one embodiment, $R^{7a}$ is aryl, for example, phenyl, such as phenyl substituted with halogen (e.g., bromine); $R^{6a}$ is hydrogen and $R^{5a}$ is alkyl, such as, aminocarbonylalkyl, which may be substituted, for example, with aryl (e.g., phenyl, including, but not limited to, phenyl substituted with aminocarbonyl). In one embodiment, $R^5$ is

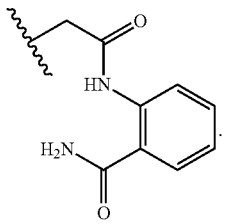 [SMILES: *CC(=O)Nc1ccccc1C(N)=O]

In another embodiment, $R^{7a}$ is hydrogen; $R^{5a}$ is aryl, for example, phenyl (e.g., disubstituted phenyl), for example, phenyl substituted with hydroxyl, halogen (e.g., chlorine), alkyl (e.g., methyl) or amino (e.g., aryl substituted sulfonylamino, for example, phenyl substituted sulfonylamino). In one embodiment, $R^{5a}$ is selected from the group consisting of:

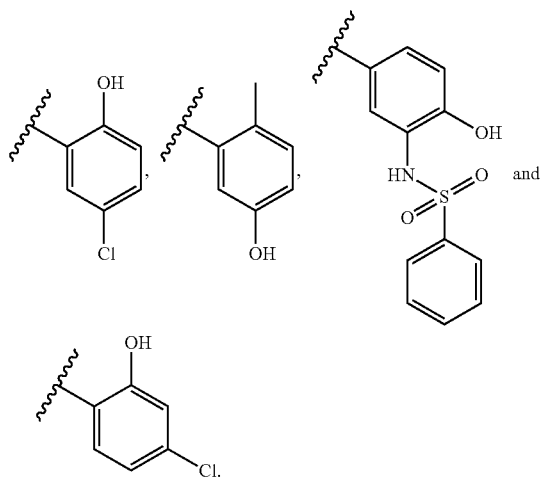

In a further embodiment, $R^{6a}$ is —$NO_2$ or hydrogen.

In yet another embodiment, $R^{7a}$ is hydrogen; $R^{5a}$ is aryl, for example, heteroaryl, such as an oxazolyl moiety

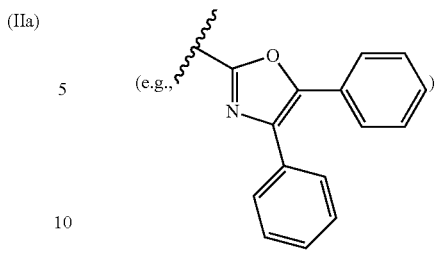

and $R^{6a}$ is halogen (e.g., chlorine).

In a further embodiment, $R^{7a}$ is hydrogen; $R^{5a}$ is alkyl, for example, heteroaryl substituted alkyl in which the heteroaryl may be a benzo[d]imidazole moiety, (e.g., a 1[H]-benzo[d]imidazole) and $R^{6a}$ is alkyl (e.g., methyl) or halogen (e.g., chlorine).

In another embodiment, the RNA binding modulatory compound of formula II is a compound of formula IIb:

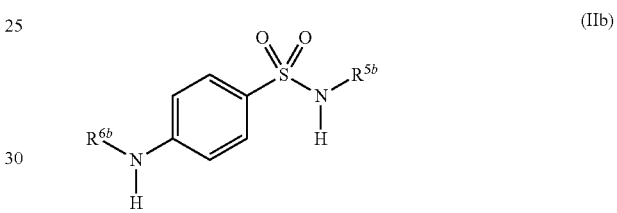
(IIb)

wherein $R^{5b}$ is aryl; and $R^{6b}$ is sulfonyl or aryl, and pharmaceutically acceptable salts thereof.

In yet another embodiment, $R^{5b}$ is aryl, such as heteroaryl, for example, isoxazolyl, thiazolyl, thiadiazolyl or pyrimidinyl, such as

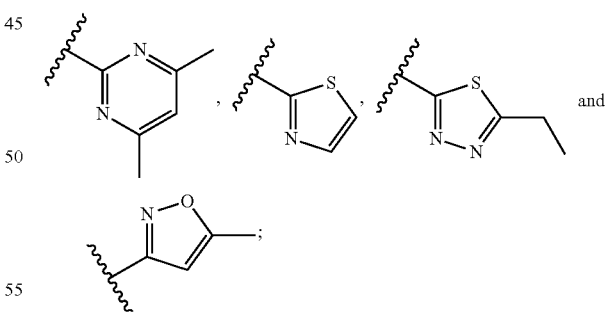

$R^{6b}$ is sulfonyl, for example, sulfonyl substituted with aryl in which the aryl may be substituted with halogen (e.g., bromine); or aryl, for example, phenyl, such as trisubstituted phenyl substituted with halogen (e.g., chlorine) and hydroxyl; heteroaryl, for example, thiazolyl, which may be substituted with aryl such as phenyl, for example, substituted with hydroxyl, alkyl (e.g., methyl) or halogen (e.g., fluorine). In another embodiment, $R^{6b}$ is selected from the group consisting of:

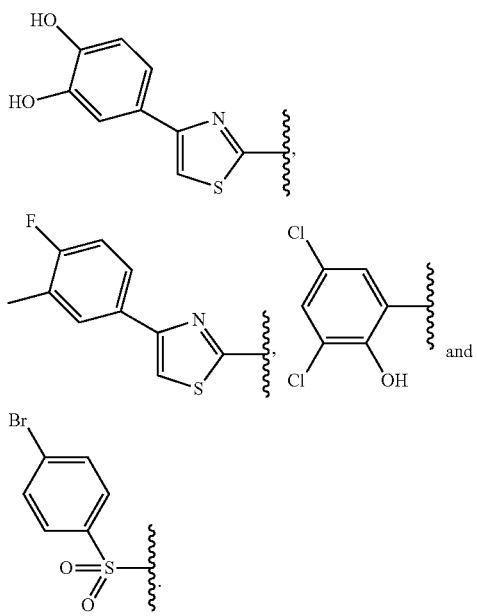

In one embodiment, the RNA binding modulatory compound of formula II is a compound of formula IIc:

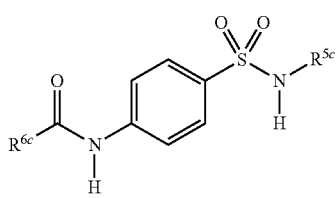

(IIc)

wherein $R^{5c}$ is aryl; and $R^{6c}$ is alkyl, aryl or a heterocyclic moiety, and pharmaceutically acceptable salts thereof.

In yet another embodiment, $R^{5c}$ is aryl, for example heteroaryl (e.g., isoxazolyl, thiazolyl or thiadiazolyl, such as

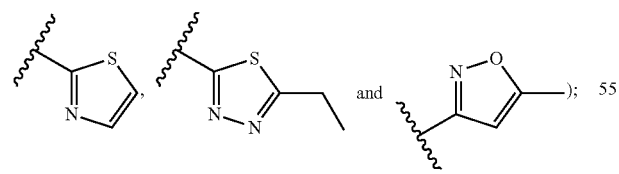

and $R^{6c}$ is alkyl, for example, $C_1$-$C_6$ alkyl that may be substituted with thiol, such as heteroaryl (e.g., benzothiazolyl or triazinyl) substituted thiol; aryloxy, for example, phenoxy, such as di- or trisubstituted phenoxy substituted with alkyl (e.g., methyl) or halogen (e.g., bromine); a heterocyclic moiety (e.g., quinazolinonyl) or aryl, for example, phenyl, such as phenyl substituted with alkyl (e.g., methyl).

In yet another embodiment, $R^{5c}$ is aryl, for example heteroaryl (e.g., isoxazolyl, thiazolyl or thiadiazolyl, such as

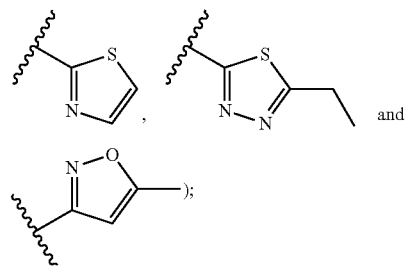

and $R^{6c}$ is aryl for example, phenyl (e.g., mono- or di-substituted phenyl), such as phenyl substituted with alkyl (e.g., t-butyl), alkoxy (e.g., methoxy or n-butoxy) or halogen (e.g., chlorine or bromine).

In another embodiment, $R^{5c}$ is aryl, for example heteroaryl (e.g., isoxazolyl, thiazolyl or thiadiazolyl, such as

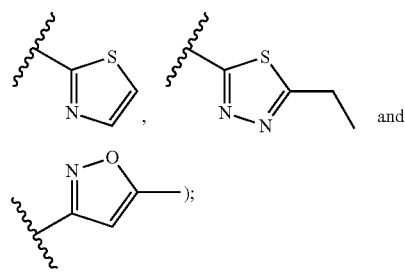

and $R^{6c}$ is a heterocyclic moiety (e.g., chromenyl or pyrrolidinonyl).

In a further embodiment, $R^{6c}$ is selected from the group consisting of:

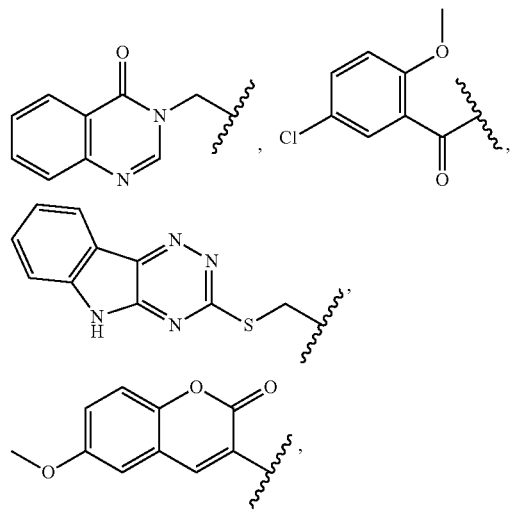

-continued
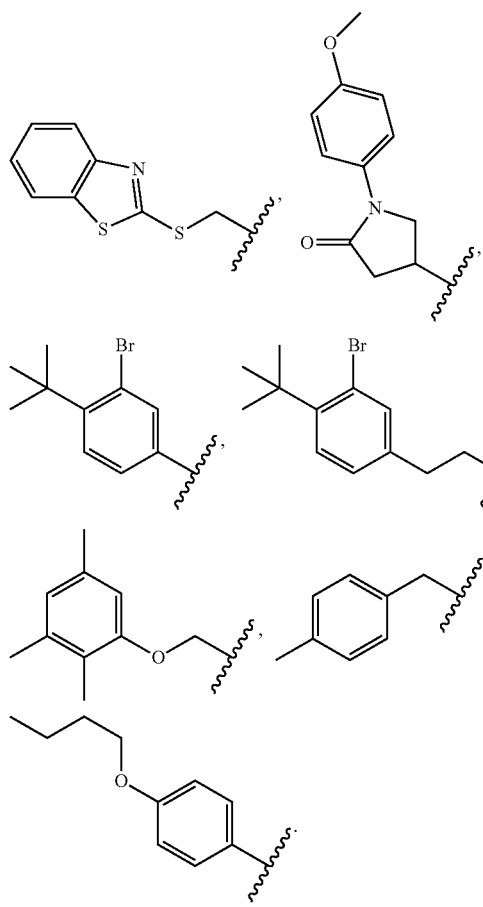
In one embodiment, the compound of formula II is selected from the group consisting of:
-continued
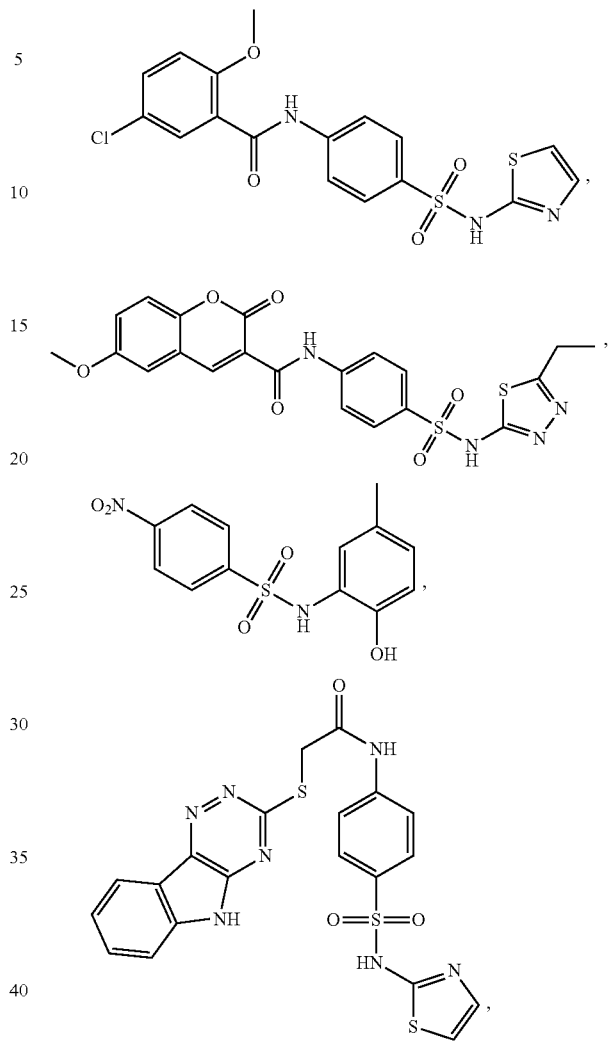
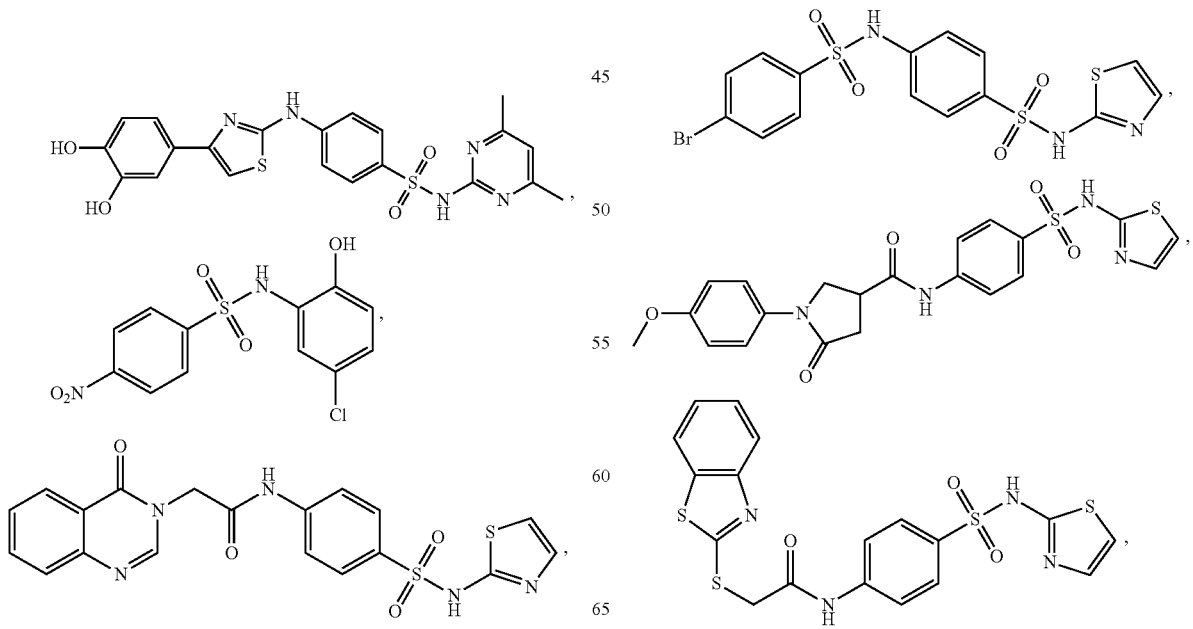

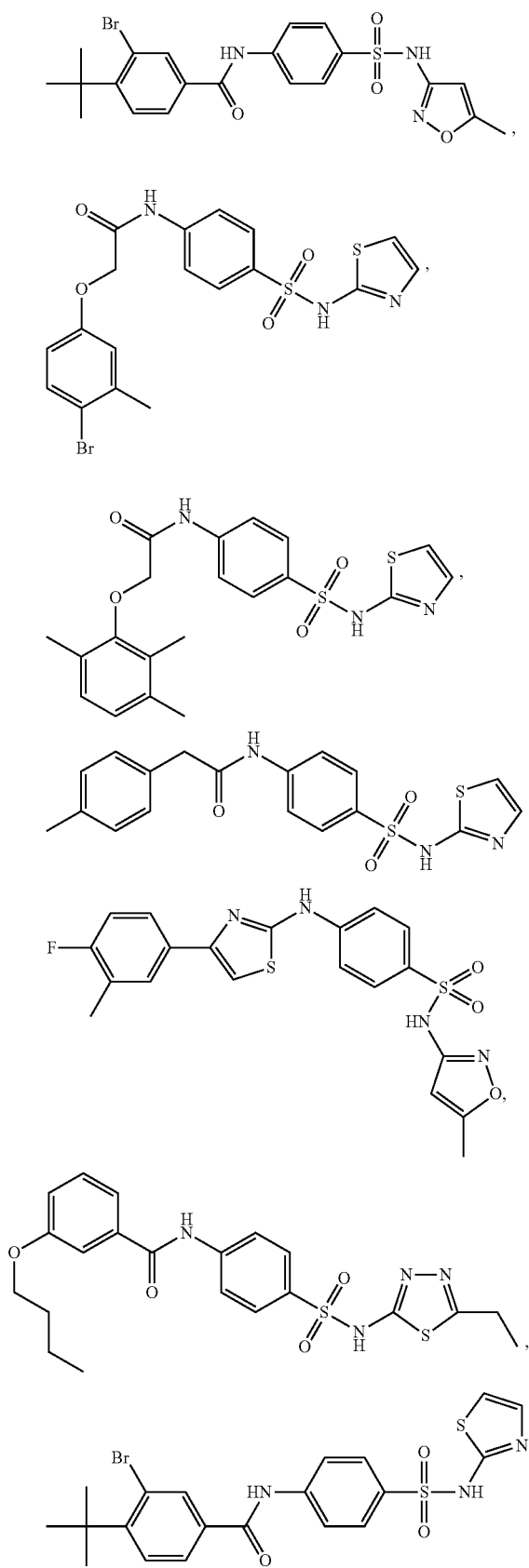
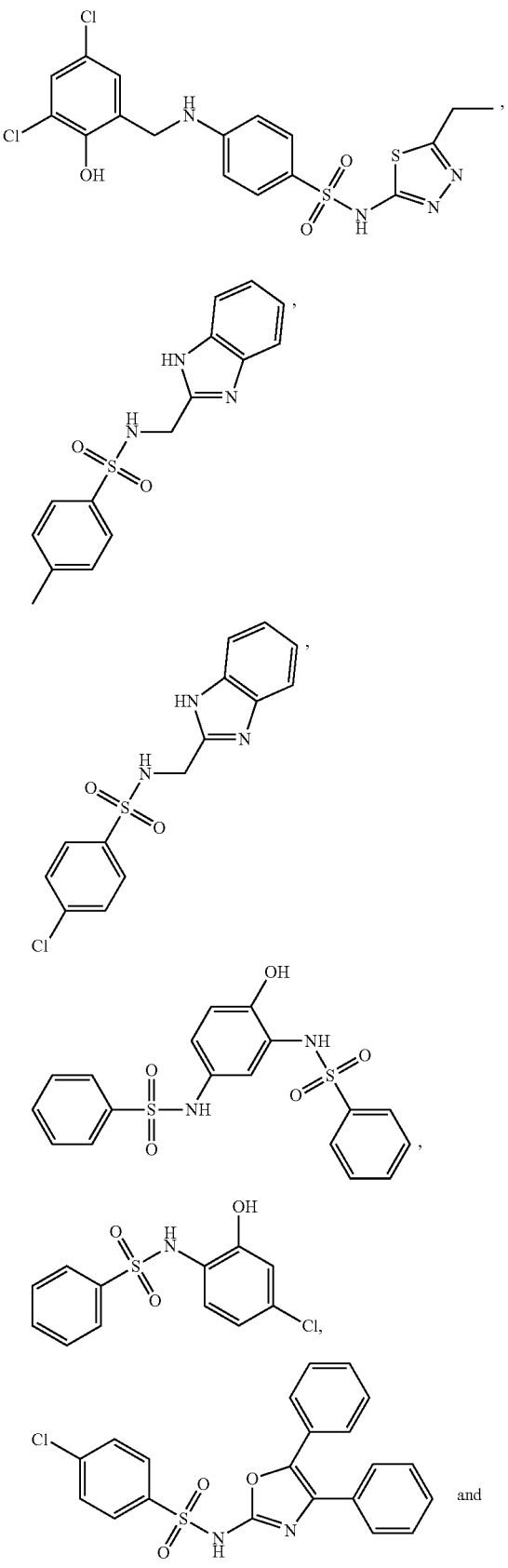

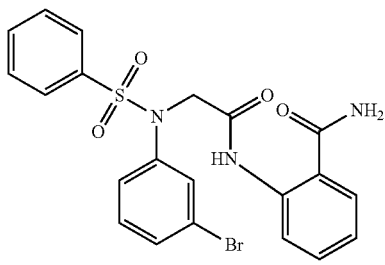

and pharmaceutically acceptable salts thereof.

In yet another embodiment, the RNA binding modulatory compound is a compound of formula III:

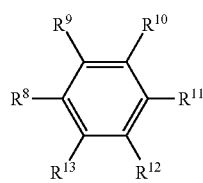
(III)

wherein $R^8$, $R^9$, $R^{10}$ and $R^{11}$ are each independently hydrogen, hydroxyl, alkyl, alkenyl, alkynyl, aryl, amino, sulfone, carbonyl, carboxylate, alkoxy, aryloxy, carbonyloxy, halogen, acyl, oximyl, hydrazinyl, —$NO_2$, —CN, a heterocyclic moiety or thioether;

$R^{12}$ is —$NR^{14}SO_2R^{15}$;

$R^{13}$ is —$NR^{16}SO_2R^{17}$;

$R^{14}$, $R^{15}$, $R^{16}$ and $R^{17}$ are each independently hydrogen, hydroxyl, alkyl, alkenyl, alkynyl, aryl, amino, sulfonyl, carbonyl, carboxylate, alkoxy, aryloxy, carbonyloxy, acyl, halogen or a heterocyclic moiety; or $R^{14}$ and $R^{15}$ and/or $R^{16}$ and $R^{17}$ together with the nitrogen atom to which they are attached are linked to form a 3-9-membered heterocyclic ring or 5-9 aryl ring; and pharmaceutically acceptable salts thereof.

In another embodiment, $R^{14}$ and $R^{16}$ are each hydrogen; $R^{15}$ and $R^{17}$ are each aryl, for example, phenyl, such as unsubstituted phenyl; $R^8$, $R^9$, and $R^{11}$ are each hydrogen and $R^{10}$ is —$NO_2$.

In another embodiment, $R^{14}$ and $R^{16}$ are each hydrogen; $R^8$, $R^{10}$ and $R^{11}$ are each hydrogen; $R^9$ is alkyl (e.g., methyl) or hydrogen; and $R^{15}$ and $R^{17}$ are each aryl, for example, phenyl, such as phenyl substituted with alkoxy (e.g., methoxy) or halogen (e.g., fluorine). In one embodiment, the phenyl is

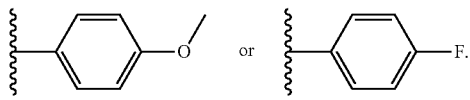

In yet another embodiment, $R^{14}$ and $R^{16}$ are each hydrogen; $R^{15}$ and $R^{17}$ are each alkyl (e.g., ethyl) and $R^8$, $R^9$, $R^{10}$ and $R^{11}$ are each hydrogen.

In one embodiment, the compound is selected from the group consisting of:

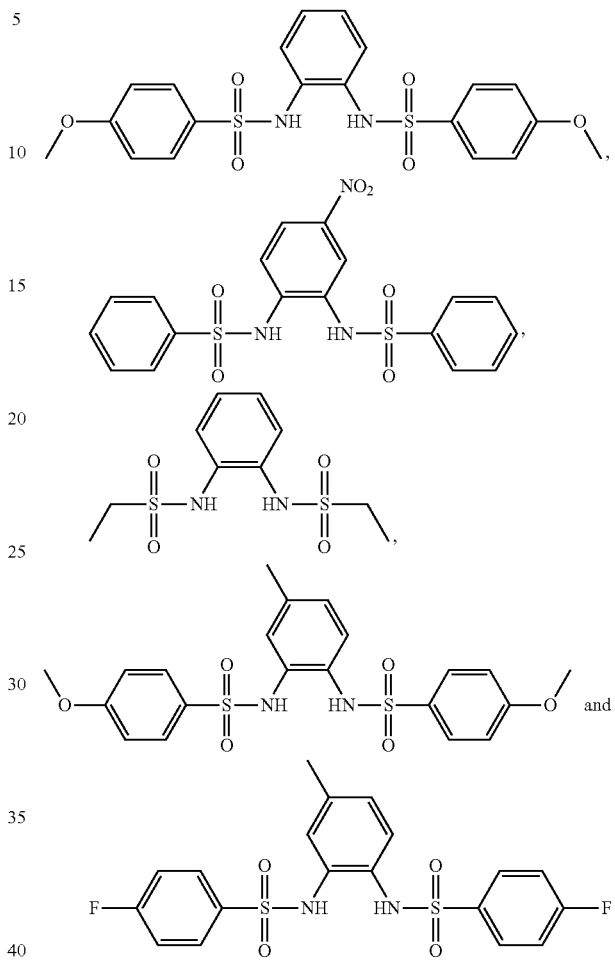

and pharmaceutically acceptable salts thereof.

In a further embodiment, the RNA binding modulatory compound is a compound of formula IV:

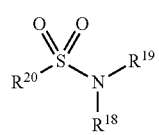
(IV)

wherein $R^{18}$ and $R^{19}$ are each independently hydrogen, hydroxyl, alkyl, alkenyl, alkynyl, aryl, amino, sulfonyl, carbonyl, carboxylate, alkoxy, aryloxy, carbonyloxy, acyl or a heterocyclic moiety; or $R^1$ and $R^3$ and/or $R^2$ and $R^4$ together with the nitrogen atom to which they are attached are linked to form a 3-9-membered heterocyclic or 5-9-membered heteroaryl ring; and $R^{20}$ is hydrogen, hydroxyl, alkyl, alkenyl, alkynyl, aryl, amino, sulfonyl, carbonyl, carboxylate, alkoxy, aryloxy, carbonyloxy, acyl, halogen or a heterocyclic moiety; and pharmaceutically acceptable salts thereof.

In one embodiment, $R^{18}$ is hydrogen; $R^{20}$ is aryl, for example, heteroaryl, such as thiophenyl, benzothiazolyl or phthalazinyl (e.g., 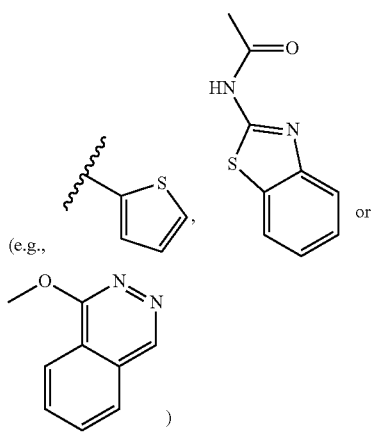 )

and $R^{19}$ is acyl (—COCH$_3$), alkyl, for example, alkyl substituted with a heterocyclic moiety (e.g., tetrahydrofuranyl), such as

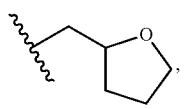 [SMILES: *CC1CCCO1]

or aryl, such as naphthyl, for example, naphthyl substituted with halogen (e.g., chlorine) and hydroxyl (e.g., 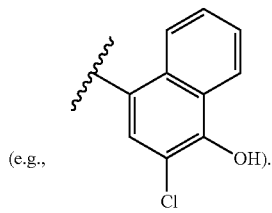 ).

In one embodiment, $R^{18}$ is hydrogen; $R^{20}$ is aryl, for example, phenyl (e.g., mono- or disubstituted phenyl), for example, phenyl substituted with —NO$_2$, alkyl (e.g., methyl) or aminocarbonyl (e.g., —CONH$_2$), such as

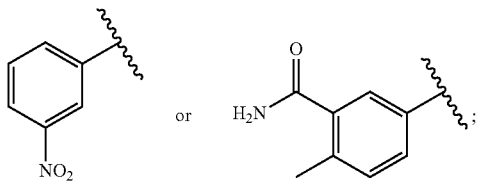 [SMILES: *c1cccc([N+](=O)[O-])c1 ; "or" ; *c1ccc(C)c(C(N)=O)c1]

and $R^{19}$ is aryl, for example, naphthyl, such naphthyl substituted with halogen (e.g., chlorine or bromine) and hydroxyl (e.g., 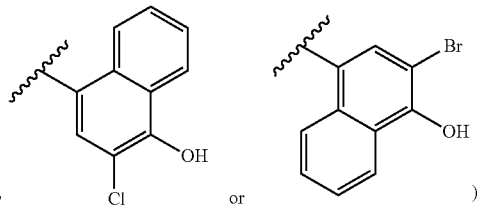 )

or phenyl, for example, phenyl substituted with alkoxy (e.g., ethoxy).

In yet another embodiment, the RNA binding modulatory compound of formula III is selected from the group consisting of:

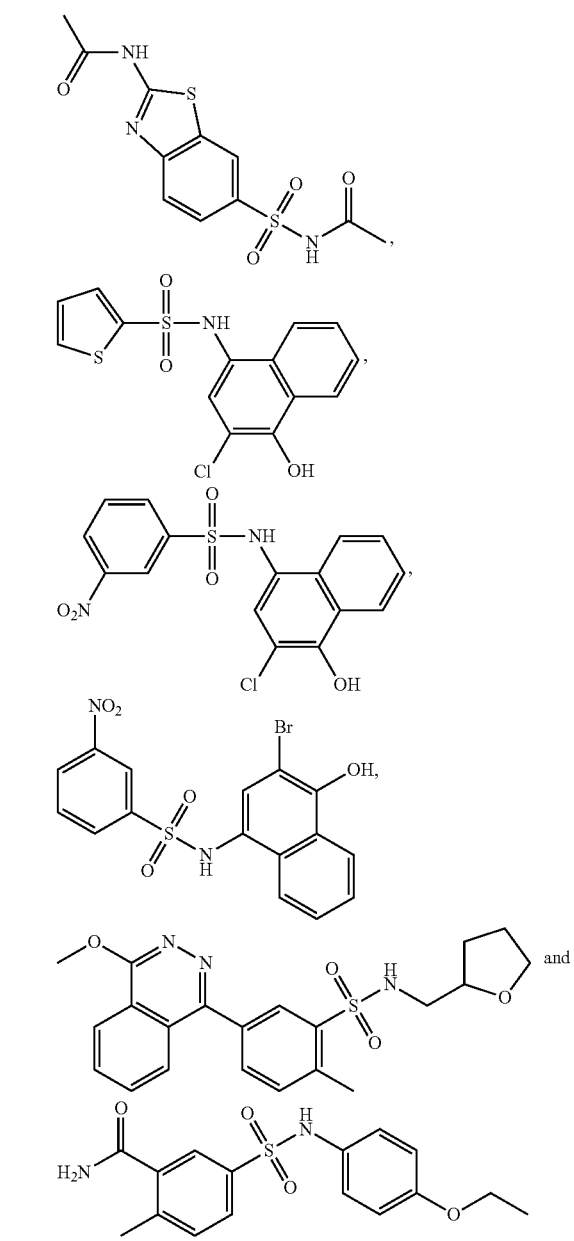

and pharmaceutically acceptable salt thereof.

In one embodiment, the RNA binding modulatory compound is a compound of formula V:

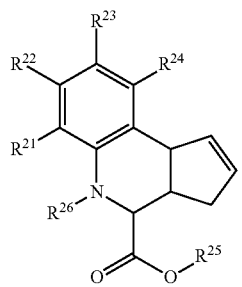

(V)

wherein $R^{21}$, $R^{22}$, $R^{23}$ and $R^{24}$ are each independently hydrogen, hydroxyl, alkyl, alkenyl, alkynyl, aryl, amino, sulfone, carbonyl, carboxylate, carbonyloxy, alkoxy, aryloxy, halogen, acyl, oximyl, hydrazinyl, —$NO_2$, —CN, a heterocyclic moiety or thioether;

$R^{25}$ is hydrogen, hydroxyl, alkyl, alkenyl, alkynyl, aryl, amino, sulfonyl, carbonyl, carboxylate, alkoxy, aryloxy, carbonyloxy, acyl or a heterocyclic moiety; and $R^{26}$ is hydrogen, hydroxyl, alkyl, alkenyl, alkynyl, aryl, amino, sulfonyl, carbonyl, carboxylate, alkoxy, aryloxy, carbonyloxy, acyl or a heterocyclic moiety; and pharmaceutically acceptable salts thereof.

In another embodiment, $R^{21}$, $R^{25}$ and $R^{26}$ are hydrogen; and $R^{23}$ is hydrogen and $R^{22}$ and $R^{24}$ are each halogen (e.g., chlorine).

In yet another embodiment, $R^{21}$, $R^{22}$, $R^{24}$, $R^{25}$ and $R^{26}$ are hydrogen; and $R^{23}$ is carboxy, for example, carboxy substituted with aryl, such as naphthyl or phenyl (e.g., phenyl substituted with alkoxycarbonyl, for example, methoxycarbonyl or ethoxycarbonyl). In one embodiment, the carboxy is

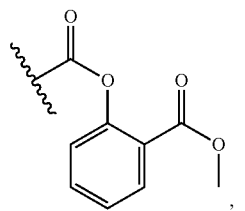

,

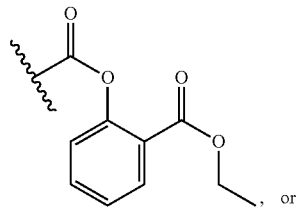

, or 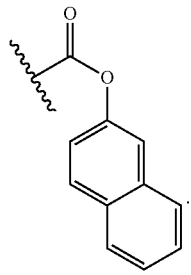 .

In yet another embodiment, $R^{21}$, $R^{22}$, $R^{24}$, $R^{25}$ and $R^{26}$ are hydrogen; and $R^{23}$ is carbonyloxy, such as carbonyloxy substituted with aryl (e.g., phenyl, including disubstituted phenyl, which may be substituted with halogen (e.g., chlorine)). In one embodiment, the carbonyloxy is

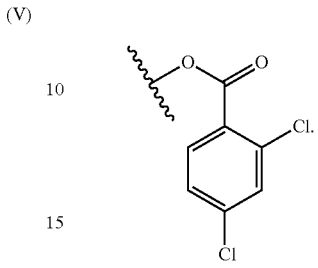

In one embodiment, the compound of formula V is selected from the group consisting of:

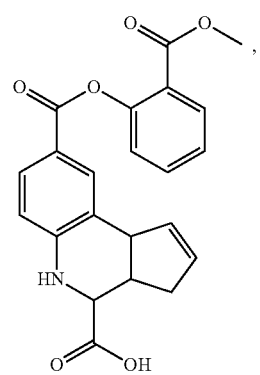

,

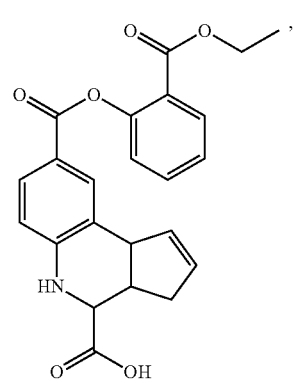

,

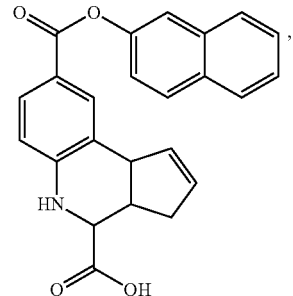

,

-continued

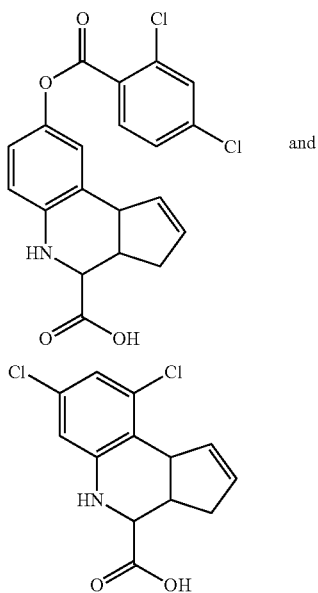
and and pharmaceutically acceptable salts thereof.

In another embodiment, the RNA binding modulatory compound is a compound of formula VI:

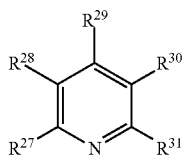
(VI)

wherein $R^{27}$, $R^{28}$, $R^{29}$, $R^{30}$ and $R^{31}$ are each independently hydrogen, hydroxyl, alkyl, alkenyl, alkynyl, aryl, amino, sulfonyl, carbonyl, carboxylate, carbonyloxy, alkoxy, aryloxy, halogen, acyl, oximyl, hydrazinyl, —$NO_2$, —CN, a heterocyclic moiety or thioether; or $R^{27}$ and $R^{28}$ or $R^{28}$ and $R^{29}$ or $R^{29}$ and $R^{30}$ or $R^{30}$ and $R^{31}$ together with the carbon atoms to which they are attached are linked to form a 4-9 carbocyclic, heterocyclic or aryl ring; and pharmaceutically acceptable salts thereof.

In one embodiment, $R^{27}$ and $R^{28}$ are linked to form an aryl moiety (e.g., phenyl); $R^{30}$ is hydrogen; $R^{31}$ is aryl, for example, furanyl (e.g., 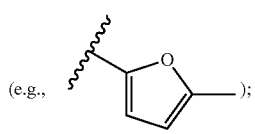 [SMILES: *c1ccc(C)o1]);

and $R^{29}$ is carbonyl, for example, carbonyl substituted with amino, which may in turn be substituted with aryl, for example, phenyl, such as phenyl substituted with halogen (e.g., chlorine). In one embodiment, $R^{29}$ is

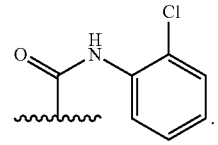

In another embodiment, $R^{27}$, $R^{28}$ and $R^{29}$ are each hydrogen and $R^{30}$ and $R^{31}$ are linked to form an aryl moiety, for example, phenyl (e.g., tri-substituted phenyl), for example, phenyl substituted with —$NO_2$, hydroxyl and alkyl, which may be substituted with a heterocyclic moiety, amino or aryl. In one embodiment, the heterocyclic moiety is morpholine or pyrrolidine, which may be substituted with alkyl (e.g., methyl). In one embodiment, the amino is substituted with carbonyl, which may be further substituted with alkyl (e.g., methyl, ethyl, n-propyl or n-butyl). In one embodiment, the aryl is furanyl or phenyl, for example, phenyl substituted with halogen (e.g., chlorine), hydroxyl or alkoxy (e.g., methoxy or alkoxy). In one embodiment, $R^{30}$ and $R^{31}$ are linked to form a ring selected from the group consisting of

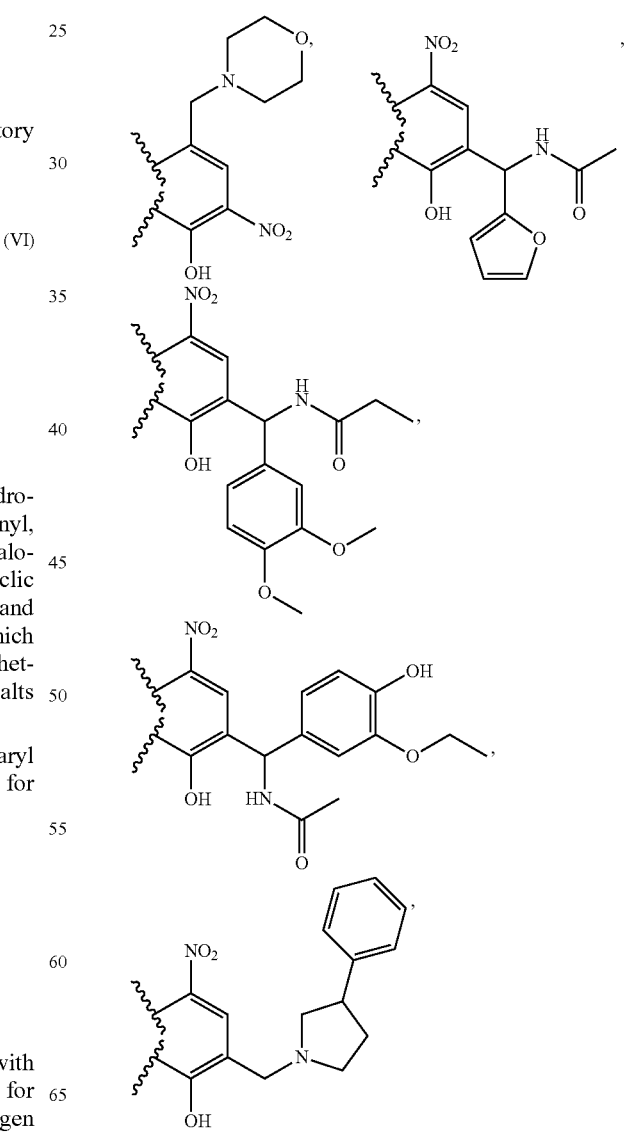

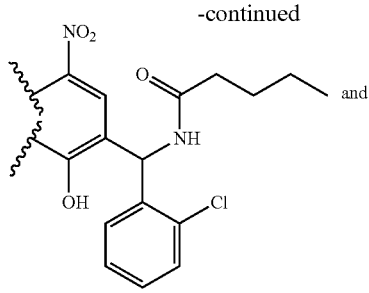

and

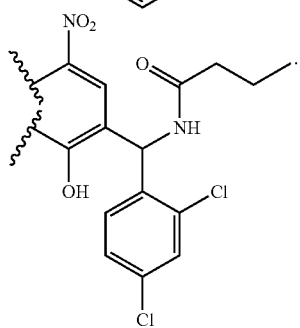

In yet another embodiment, $R^{28}$, $R^{29}$ and $R^{30}$ are each hydrogen and $R^{27}$ and $R^{31}$ are each substituted with carbonyl, for example, carbonyl substituted with amino, which may be substituted with aryl, such as thiadiazolyl (e.g., thiadiazolyl substituted with alkyl, for example, methyl or n-propyl) or benzothiazolyl. In one embodiment, $R^{27}$ and $R^{31}$ are

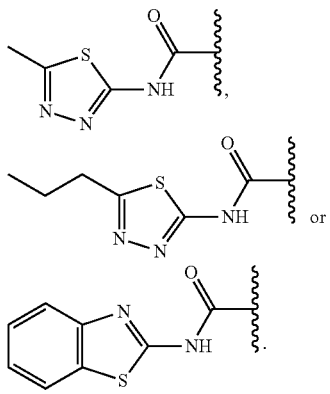

In a further embodiment, $R^{27}$, $R^{29}$ and $R^{30}$ are each hydrogen and $R^{28}$ and $R^{31}$ are each carbonyl, for example, carbonyl substituted with amino, which may be further substituted with alkyl (e.g., alkyl substituted with aryl, for example, phenyl, such as phenyl substituted with alkoxy (e.g., methoxy). In one embodiment, $R^{28}$ and $R^{31}$ are each

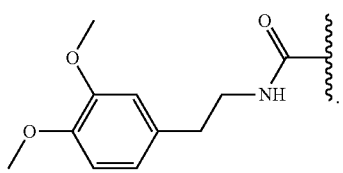 [SMILES: *C(=O)NCCc1ccc(OC)c(OC)c1]

In one embodiment, the RNA binding modulatory compound of formula VI is a compound of formula VIa:

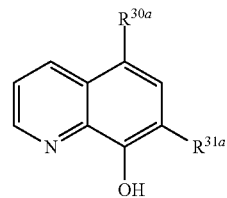
(VIa)

wherein
$R^{30a}$ and $R^{31a}$ are each —$NO_2$ or alkyl; and pharmaceutically acceptable salts thereof.

In one embodiment, $R^{31a}$ is —$NO_2$ and $R^{30a}$ is alkyl, which may be substituted with a heterocyclic moiety (e.g., morpholine).

In another embodiment, $R^{30a}$ is —$NO_2$ and $R^{31a}$ is alkyl, for example, alkyl substituted with a heterocyclic moiety, amino or aryl. In one embodiment, the heterocyclic moiety is pyrrolidine, which may be substituted with alkyl (e.g., methyl). In one embodiment, the amino is substituted with carbonyl, which may be further substituted with alkyl (e.g., methyl, ethyl, n-propyl or n-butyl). In one embodiment, the aryl is furanyl or phenyl, for example, phenyl substituted with halogen (e.g., chlorine), hydroxyl or alkoxy (e.g., methoxy or alkoxy). In one embodiment, $R^{31a}$ is selected from the group consisting of

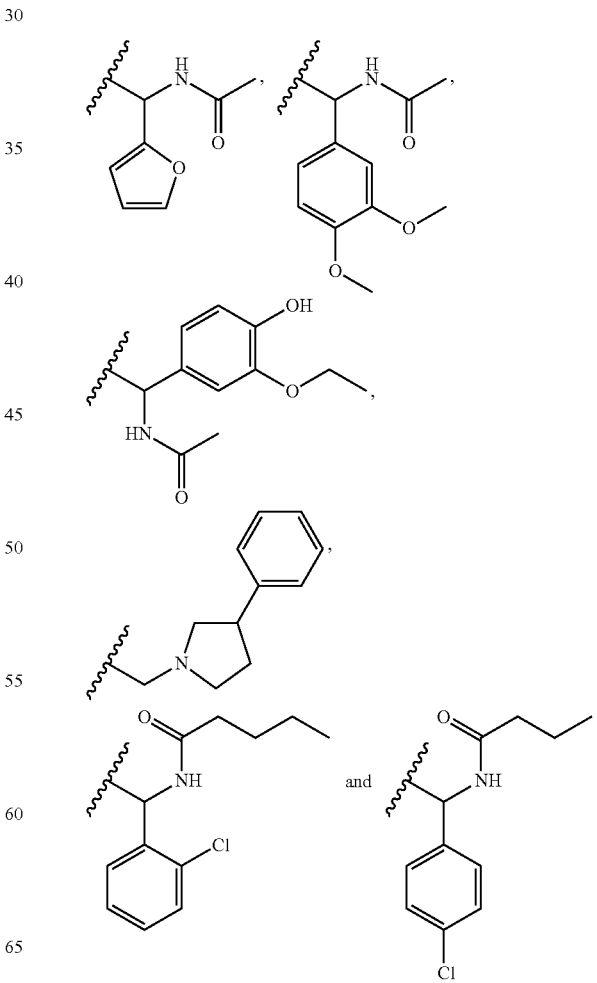

and

In yet another embodiment, the RNA binding modulatory compound of formula VI is a compound of formula VIb:

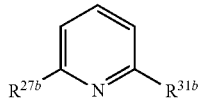
(VIb)

wherein $R^{27b}$ and $R^{31b}$ are each carbonyl; and pharmaceutically acceptable salts thereof.

In one embodiment, the carbonyl is substituted with amino, which may be substituted with aryl, such as thiadiazolyl (e.g., thiadiazolyl substituted with alkyl, for example, methyl or n-propyl) or benzothiazolyl. In one embodiment, the carbonyl is substituted with

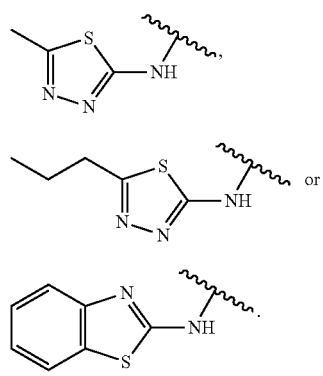

In another embodiment, the compound of formula VI is selected from the group consisting of

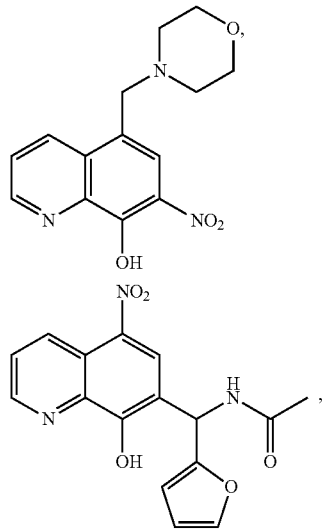

-continued

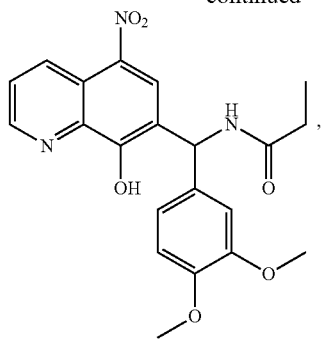

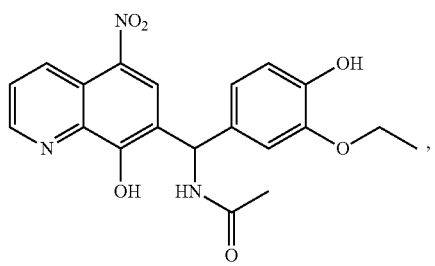

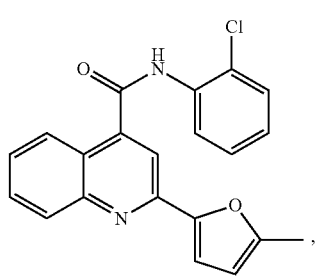

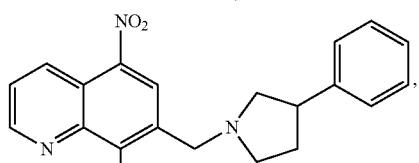

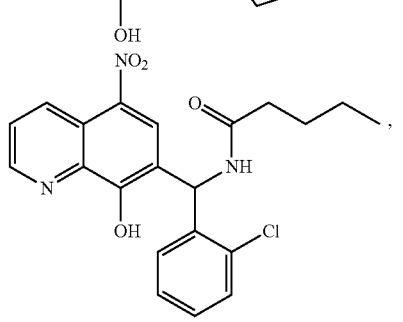

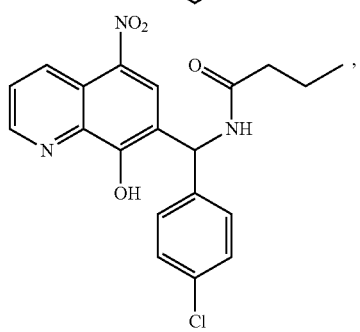

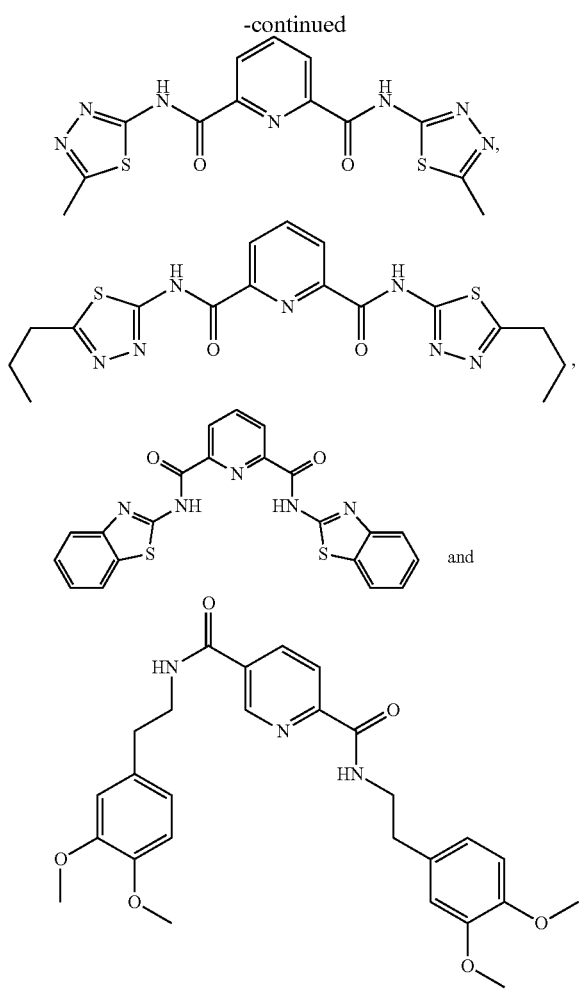

and pharmaceutically acceptable salts thereof.

In yet another embodiment, the RNA binding modulatory compound is a compound of formula VII:

(VII)

wherein

U is $NR^{32}$, O or S;

W is N or $CR^{33}$ when q is a double bond, or W is $NR^{44}$, $CR^{45}R^{46}$ or C=D when q is a single bond;

X is N or $CR^{34}$ when q is a double bond, or X is $NR^{47}$, $CR^{48}R^{49}$ or C=E when q is a single bond;

Y is $NR^{35}$, $CR^{36}R^{37}$ or C=G when p is a single bond, or Y is N or $CR^{38}$ when p is a double bond;

Z is $NR^{39}$, $CR^{40}R^{41}$ or C=A when p is a single bond, or Z is N or $CR^{42}$ when p is a double bond;

p and q are each independently a single or double bond;

$R^{32}$, $R^{35}$, $R^{39}$, $R^{43}$, $R^{44}$, $R^{47}$, $R^{52}$, $R^{55}$ and $R^{58}$ are each independently hydrogen, hydroxyl, alkyl, alkenyl, alkynyl, aryl, amino, sulfonyl, carbonyl, carboxylate, alkoxy, aryloxy, carbonyloxy, acyl or a heterocyclic moiety;

$R^{33}$, $R^{34}$, $R^{36}$, $R^{37}$, $R^{38}$, $R^{40}$, $R^{41}$, $R^{42}$, $R^{45}$, $R^{46}$, $R^{48}$, $R^{49}$, $R^{50}$, $R^{51}$, $R^{53}$, $R^{54}$, $R^{56}$, $R^{57}$, $R^{59}$ and $R^{60}$ are each independently hydrogen, hydroxyl, alkyl, alkenyl, alkynyl, aryl, amino, sulfonyl, carbonyl, carboxylate, alkoxy, aryloxy, carbonyloxy, halogen, acyl, oximyl, hydrazinyl, $-NO_2$, $-CN$, a heterocyclic moiety or thioether; or $R^{33}$ and $R^{34}$ together with the atoms to which they are attached are linked to form a 4-12 membered carbocyclic, aryl or heterocyclic ring; or $R^{35}$, $R^{36}$ or $R^{38}$ and $R^{39}$, $R^{40}$ or $R^{41}$ together with the atoms to which they are attached are linked to form a 4-12 membered carbocyclic, aryl or heterocyclic ring; or $R^{32}$ and $R^{33}$ together with the atoms to which they are attached are linked to form a 4-12 membered carbocyclic, aryl or heterocyclic ring; and A is O, S, $NR^{43}$ or $CR^{50}R^{51}$;

D is O, S, $NR^{52}$ or $CR^{53}R^{54}$;

E is O, S, $NR^{55}$ or $CR^{56}R^{57}$;

G is O, S, $NR^{58}$ or $CR^{59}R^{60}$; and pharmaceutically acceptable salts thereof.

In one embodiment, p and q are each a double bond; U is O; W is $CR^{33}$ and Z is $CR^{42}$; X is N; Y is N; $R^{42}$ is thiol (e.g., —SH) or aryl, for example, phenyl, such as phenyl substituted with halogen (e.g., bromine) or quinoline, for example, quinoline substituted with aryl (e.g., phenyl); $R^{33}$ is thiol, for example, thiol substituted with aryl (e.g., phenyl, which may be substituted with $-NO_2$ and carboxylate) or aryl. In one embodiment, $R^{33}$ is

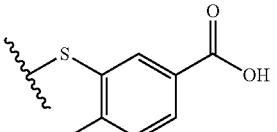

and $R^{42}$ is

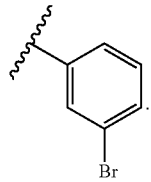 [SMILES: *c1cccc(Br)c1]

Alternatively, $R^{33}$ is

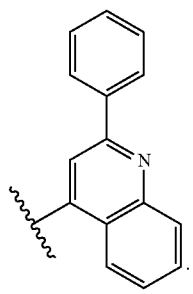 [SMILES: *c1cc(-c2ccccc2)nc2ccccc12]

In another embodiment, Y is $CR^{38}$; $R^{38}$ and $R^{42}$ are each aryl (e.g., phenyl) and $R^{33}$ is amino, for example, amino substituted with carbonyl, which may be substituted with aryl (e.g., phenyl, for example phenyl substituted with alkyl, such as methyl) In one embodiment, $R^{33}$ is

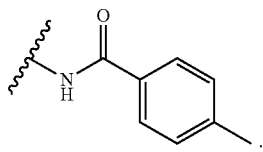 [SMILES: *NC(=O)c1ccc(C)cc1]

In yet another embodiment, p and q are each a double bond; U is S; W is CR$^{33}$ and Z is CR$^{42}$; X is N; Y is N; R$^{33}$ is amino or thiol. In one embodiment, R$^{33}$ is amino, for example, amino substituted with carbonyl or oximyl. In another embodiment, the oximyl is an aryl substituted oximyl, such as phenyl substituted oximyl in which the phenyl may be further substituted with —NO$_2$. In yet another embodioxy, such as ethoxy) or aryl (e.g., heteroaryl, for example, triazole). Alternatively, R$^{33}$ is thiol, for example, thiol substituted with alkyl (e.g., aryl substituted alkyl, such as phenyl substituted alkyl, which may be further substituted with halogen, such as chlorine). In one embodiment, R$^{33}$ is

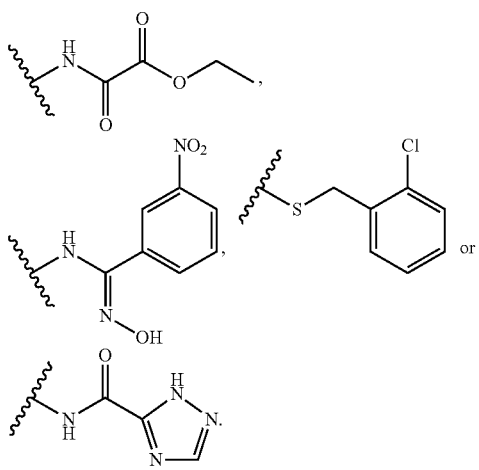

In another embodiment, R$^{42}$ is alkyl, for example, t-butyl or alkyl substituted with aryl (e.g., phenyl, for example phenyl substituted with halogen, such as chlorine) or carbonyl (e.g., alkoxy substituted carbonyl, for example, ethoxyl substituted carbonyl). Alternatively R$^{42}$ is aryl (e.g., heteroaryl, such as pyridine) or thiol (e.g., —SH). In another embodiment, R$^{42}$ is

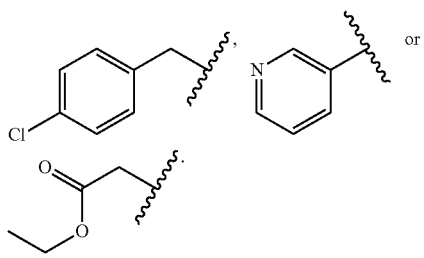

In yet another embodiment, p and q are each a double bond; U is S; W is CR$^{33}$ and Z is CR$^{42}$; X is N; Y is CR$^{38}$; R$^{42}$ is hydrogen; R$^{38}$ is aryl, for example, phenyl, such as phenyl substituted with hydroxyl (e.g., is 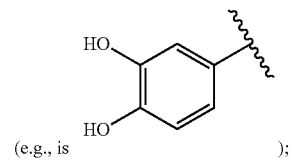 [SMILES: *c1ccc(O)c(O)c1] );

and R$^{33}$ is amino, for example, amino substituted with aryl, such as, naphthyl (e.g., 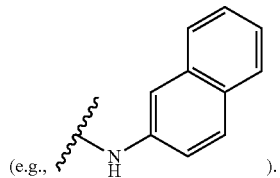 [SMILES: *Nc1ccc2ccccc2c1] ).

In another embodiment, p and q are each a double bond; U is S; W is CR$^{33}$ and Z is CR$^{42}$; X is CR$^{34}$; Y is CR$^{38}$; R$^{33}$ and R$^{34}$ are each alkyl (e.g., methyl); R$^{38}$ is carbonyl, for example, carbonyl substituted with amino (e.g., —NH$_2$); R$^{42}$ is amino, for example, amino substituted with carbonyl, such as aryl substituted carbonyl (e.g., pyrazine substituted carbonyl, for example,

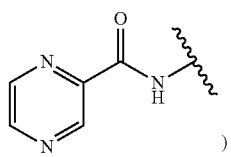 [SMILES: *NC(=O)c1cnccn1] )

and R$^{33}$ is amino (e.g., amino substituted with carbonyl, such as carbonyl substituted with cyclohexenyl, for example,

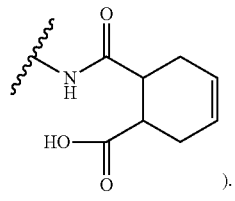 [SMILES: *NC(=O)C1CC=CCC1C(=O)O] ).

In another embodiment, R$^{34}$ is carbonyl, for example, carbonyl substituted with alkoxy (e.g., methoxy); R$^{42}$ is alkyl (e.g., ethyl); and R$^{38}$ is aryl, for example, phenyl, such as phenyl substituted with halogen (e.g., chlorine). In one embodiment, R$^{38}$ is

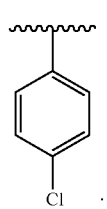 [SMILES: *c1ccc(Cl)cc1] .

In yet another embodiment, $R^{38}$ and $R^{42}$ are linked to join a ring (e.g., a 6-membered or 12-membered carbocyclic ring), for example,

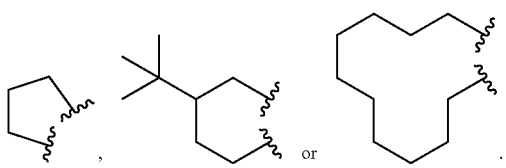

In one embodiment, $R^{33}$ is amino, for example, amino substituted with carbonyl (e.g., alkyl substituted carbonyl such as alkyl substituted with carboxylate). In one embodiment, $R^{33}$ is

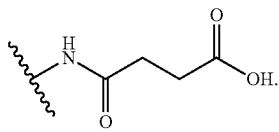 [SMILES: *NC(=O)CCC(=O)O]

In another embodiment, $R^{34}$ is carbonyl, for example, alkoxy (e.g., methoxy) substituted carbonyl.

In another embodiment, $R^{33}$ and $R^{34}$ are linked to form a 6-membered heterocyclic ring, for example,

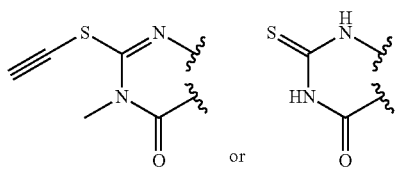

In yet another embodiment, p and q are each a double bond; U is $NR^{32}$; X is N; Y is N; W is $CR^{33}$ and Z is $CR^{42}$; $R^{42}$ is thiol (e.g., —SH); $R^{32}$ is hydrogen, alkyl (e.g., methy or alkyl substituted with aryl, for example, phenyl, or alkenyl) or aryl, for example, unsubstituted phenyl or phenyl substituted with alkyl (e.g., methyl) or halogen (e.g., fluorine). In one embodiment, $R^{32}$ is

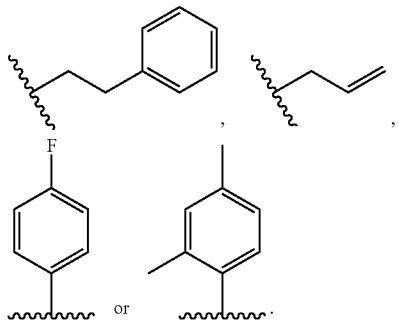

In a further embodiment, $R^{33}$ is alkyl, for example, alkyl substituted with aryloxy, for example, naphthyloxy or phenoxy, such as halogen (e.g., bromine) substituted phenoxy, alkyl (e.g., methyl) substituted phenoxy or alkoxy (e.g., methoxy) substituted phenoxy. In another embodiment $R^{33}$ is a thiol substituted alkyl (e.g., arylalkylthioalkyl, such as phenyl substituted alkylthioalkyl in which the phenyl may be further substituted with halogen, for example chlorine); a heterocyclic substituted alkyl (e.g., alkyl substituted with

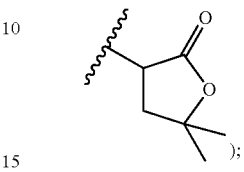

aryl substituted alkyl, for example, phenyl substituted alkyl (e.g., unsubstituted phenyl or phenyl substituted with halogen, such as chlorine, or phenyl substituted with alkoxy, such as isopropoxy). Alternatively, $R^{33}$ is aryl, for example, thiophenyl or phenyl, for example, phenyl substituted with hydroxyl or alkoxy (e.g., methoxy). In another embodiment, $R^{33}$ is selected from the group consisting of

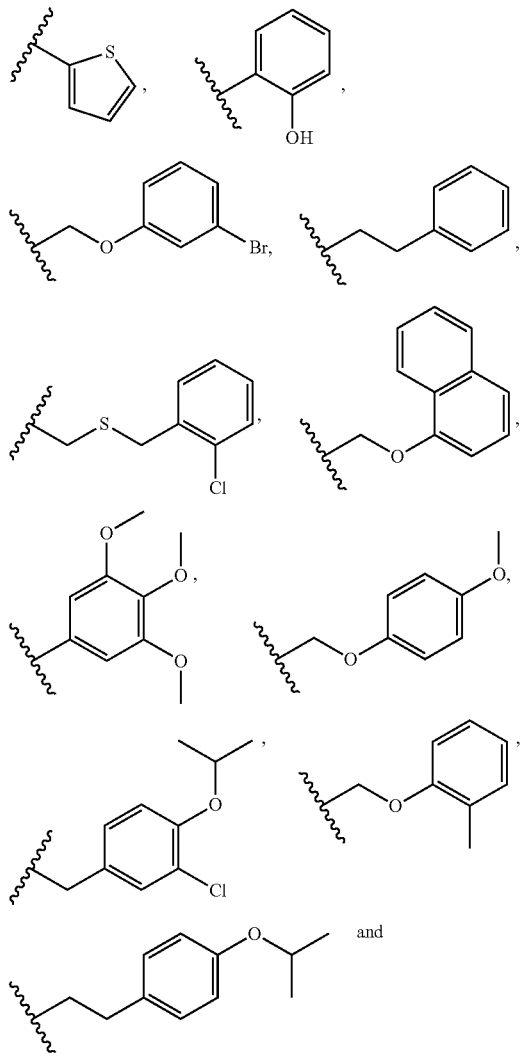

and

-continued

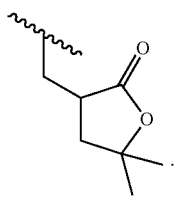

In another embodiment, $R^{32}$ and $R^{33}$ are linked to form a 6-membered heterocyclic ring

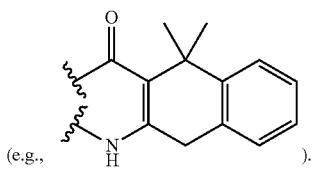 [SMILES: *NC1=C(C(*)=O)C(C)(C)c2ccccc2C1]
(e.g., ).

In another embodiment, U is $NR^{32}$; X is N; Y is N; W is $CR^{33}$; Z is $CR^{42}$; $R^{32}$ is hydrogen; $R^{33}$ is hydrogen; $R^{42}$ is amino, for example, amino substituted with carbonyl (e.g., carbonyl substituted with aryl, such as phenyl, which may be substituted with hydroxyl). In yet another embodiment, $R^{42}$ is a heterocyclic moiety

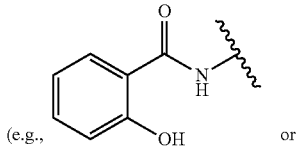
(e.g., OH or

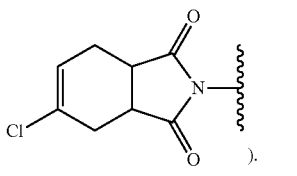
).

In another embodiment, U is $NR^{32}$; W is $CR^{33}$, X is $CR^{34}$, Y is $CR^{35}$; Z is N; $R^{32}$ is hydrogen or alkyl (e.g., alkyl substituted with carboxylate, for example, —CH$_2$CH$_2$COOH); $R^{33}$ is hydrogen or alkyl (e.g., methyl); $R^{34}$ is alkenyl (e.g., alkenyl substituted with a heterocyclic moiety, for example,

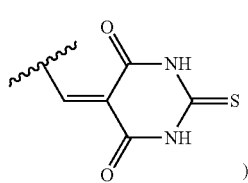 [SMILES: *C=C1C(=O)NC(=S)NC1=O]
)

or aryl (e.g., phenyl or benzothiazolyl); $R^{38}$ is aryl, for example, phenyl, such as phenyl substituted with hydroxyl, alkoxy (e.g., methoxy), alkyl (e.g., ethyl) or a heterocyclic moiety. In one embodiment, $R^{38}$ is

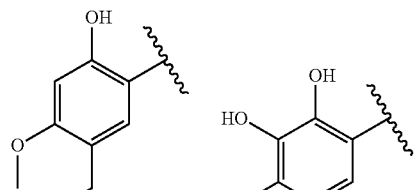
, or

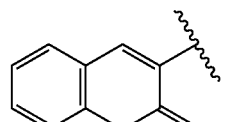

In another embodiment, p and q are each a double bond; U is $NR^{32}$; W is $CR^{33}$, X is N, Y is $CR^{38}$; Z is N; $R^{32}$ is aryl (e.g., phenyl); $R^{33}$ is a heterocyclic moiety

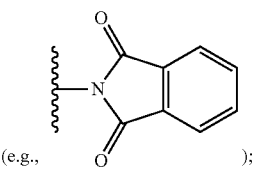 [SMILES: *N1C(=O)c2ccccc2C1=O]
(e.g., );

$R^{38}$ is amino, such as, amino substituted with carbonyl (e.g., carbonyl substituted with aryl, for example, phenyl, such as phenyl substituted with alkoxy (e.g., methoxy), alkyl (e.g., methyl)) or sulfonyl (e.g., sulfonyl substituted with aryl, for example, phenyl, which may be substituted with alkyl (e.g., methyl)). In one embodiment, $R^{38}$ is

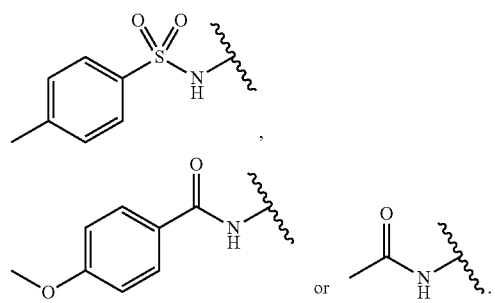

In another embodiment, $R^{32}$ and $R^{33}$ are linked to form a 5 or 6-membered heterocyclic ring, for example

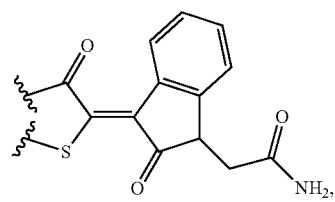

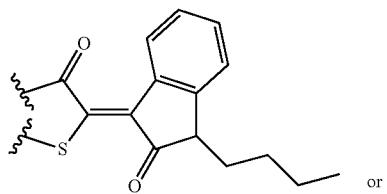

or

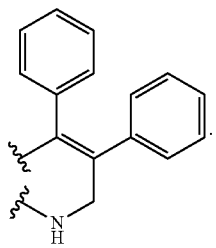

In another embodiment, R³⁸ is amino (e.g., amino substituted with carbonyl, for example, aryl substituted carbonyl, such as phenyl substituted carbonyl, including —NO₂ substituted phenyl) or aryl (e.g., phenyl, for example, phenyl substituted with carbonyloxy, such as alkyl substituted carbonyloxy, including, but not limited to methyl substituted carbonyloxy). In one embodiment, R³⁸ is

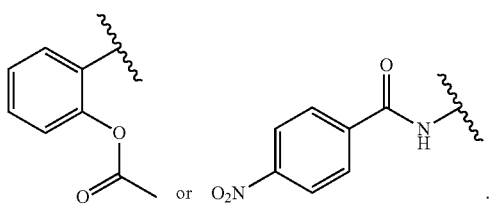 [SMILES: *c1ccccc1OC(C)=O ; *NC(=O)c1ccc([N+](=O)[O-])cc1]

In another embodiment, p and q are each a double bond; U is NR³²; W is N; X is N; Y is N; Z is CR⁴²; R³² is hydrogen; R⁴² is amino, for example, amino substituted with carbonyl (e.g., aryl substituted carbonyl, for example, heteroaryl substituted carbonyl, such as thiophenyl substituted carbonyl

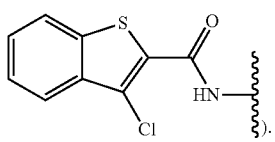 [SMILES: *NC(=O)c1sc2ccccc2c1Cl]

In yet another embodiment, U is NR³²; q is a double bond and p is a single bond; W is CR³³; X is N; Y is NR³⁵ and Z is C=A; A is S; R³⁵ is hydrogen; R³² is hydrogen, alkyl (e.g., methyl, ethyl or aryl substituted alkyl, for example, phenyl substituted alkyl) or aryl (e.g., phenyl, such as phenyl substituted with alkyl, such as methyl or ethyl, for example,

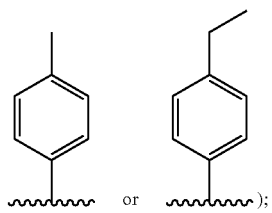

$R^{33}$ is aryl, such as furanyl or phenyl, for example, phenyl substituted with hydroxyl, halogen (e.g., bromine or chlorine) and alkoxy (e.g., methoxy). In one embodiment, $R^{33}$ is

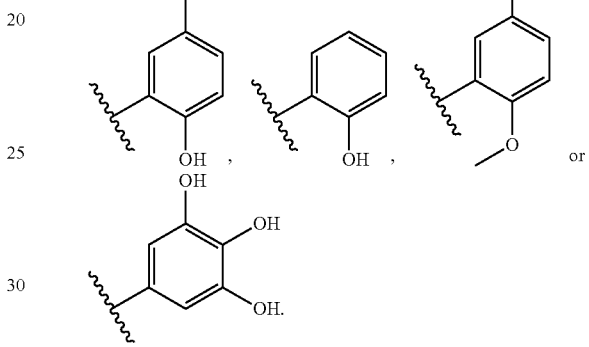

In one embodiment, U is NR³²; q is a double bond and p is a single bond; W is N; X is CR³⁴; Y is C=G; Z is C=A; A is O; R³² is aryl, for example, phenyl substituted with sulfonyl (e.g., amino substituted sulfonyl), carboxylate or halogen (e.g., chlorine), such as

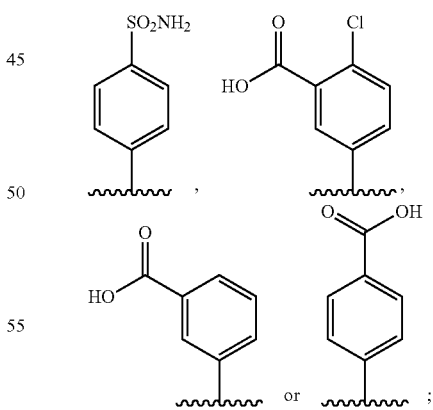

$R^{34}$ is alkyl (e.g., methyl); G is $CR^{59}R^{60}$, $R^{59}$ is hydrogen and $R^{60}$ is aryl, for example, phenyl, such as phenyl substituted with alkoxy (e.g., methoxy or ethoxy) or carbonyloxy, for example, carbonyloxy substituted with aryl (e.g., heteroaryl, for example, thiophenyl or furanyl). In one embodiment, $R^{60}$ is

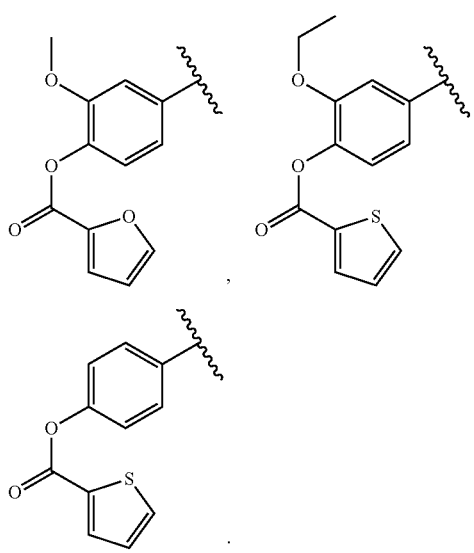

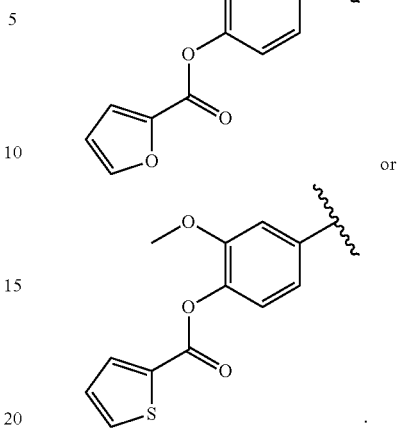

In yet another embodiment, U is NR$^{32}$; p and q are each a single bond; W is NR$^{44}$, X is C=E, Y is C=G; Z is C=A; R$^{44}$ is hydrogen; A and E are O; R$^{32}$ is aryl, for example, phenyl, such as unsubstituted phenyl or phenyl substituted with halogen (e.g., chlorine or fluorine) or carbonyl, for example, carbonyl substituted with alkoxy (e.g., ethoxy), for example,

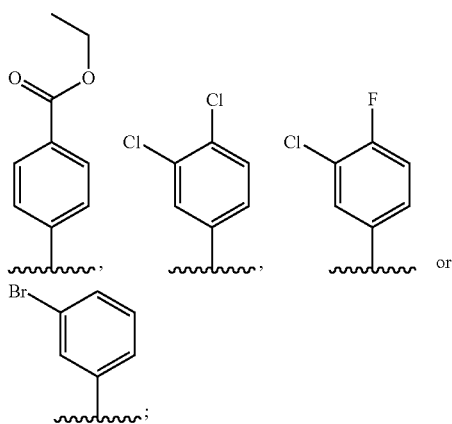

G is CR$^{59}$R$^{60}$; R$^{59}$ is hydrogen; R$^{60}$ is aryl, for example, phenyl, such as phenyl substituted with alkoxy (e.g., methoxy) or carbonyloxy (e.g., carbonyloxy substituted with aryl, for example, heteroaryl such as thiophenyl or furanyl). In one embodiment, R$^{60}$ is

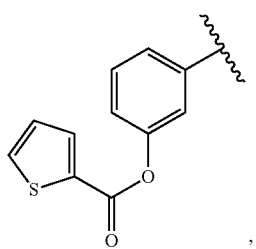

In one embodiment, the RNA binding modulatory compound of formula VII is a compound of formula VIIa:

(VIIa)

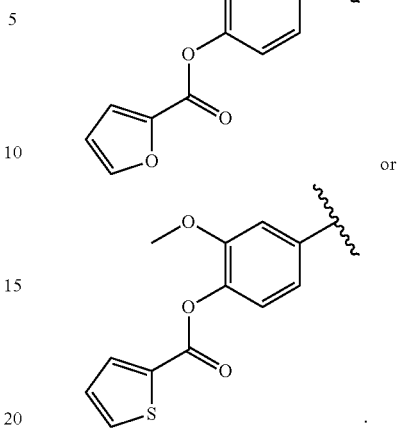

wherein

U$^a$ is O or S;

R$^{33a}$ is amino, thiol or aryl; and

R$^{42a}$ is aryl, thiol, or alkyl; and pharmaceutically acceptable salts thereof.

In one embodiment, U$^a$ is S; R$^{33a}$ is amino, for example, amino substituted with carbonyl or oximyl. In another embodiment, the oximyl is aryl substituted oximyl, such as phenyl substituted oximyl in which the phenyl may be further substituted with —NO$_2$. In yet another embodiment, the carbonyl may be substituted with carbonyl (e.g., carbonyl substituted with alkoxy, such as ethoxy) or aryl (e.g., heteroaryl, for example, triazole). Alternatively, R$^{33a}$ is thiol, for example, thiol substituted with alkyl (e.g., aryl substituted alkyl, such as phenyl substituted alkyl, which may be further substituted with halogen such as chlorine). In one embodiment, R$^{33a}$ is

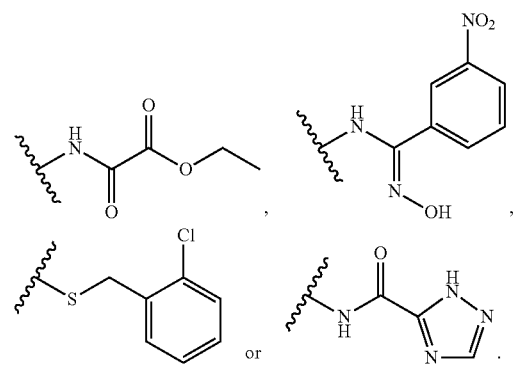

In another embodiment, $R^{42a}$ is alkyl, for example, t-butyl or alkyl substituted with aryl (e.g., phenyl, for example, phenyl substituted with halogen, such as chlorine) or carbonyl (e.g., alkoxy substituted carbonyl, for example, ethoxy substituted carbonyl). Alternatively $R^{42a}$ is aryl (e.g., heteroaryl, such as pyridine) or thiol (e.g., —SH). In another embodiment, $R^{42}$ is

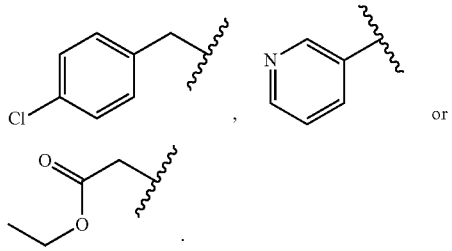

In another embodiment, $U^a$ is O; $R^{42a}$ is thiol (e.g., —SH) or aryl, for example, phenyl, such as phenyl substituted with halogen (e.g., bromine) or quinoline, for example, quinoline substituted with aryl (e.g., phenyl); $R^{33a}$ is thiol, for example, thiol substituted with aryl (e.g., phenyl, which may be substituted with —NO$_2$ and carboxylate) or aryl. In one embodiment, $R^{33a}$ is

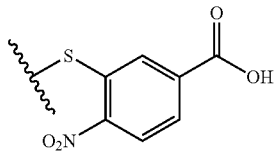

and $R^{42a}$ is

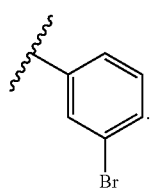 [SMILES: *c1cccc(Br)c1]

Alternatively, $R^{33a}$ is

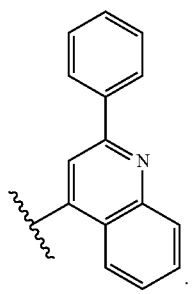

In another embodiment, the RNA binding modulatory compound of formula VII is a compound of formula VIIb:

wherein $R^{32b}$ is hydrogen, aryl or alkyl; and $R^{33b}$ is alkyl or aryl; or $R^{32b}$ and $R^{33b}$ together with the atoms to which they are attached are linked to form a 6-membered heterocyclic ring; and pharmaceutically acceptable salts thereof.

In one embodiment, $R^{32b}$ is hydrogen, alkyl (e.g., methy or alkyl substituted with aryl, for example, phenyl, or alkenyl) or aryl, for example, unsubstituted phenyl or phenyl substituted with alkyl (e.g., methyl) or halogen (e.g., fluorine). In one embodiment, $R^{32b}$ is

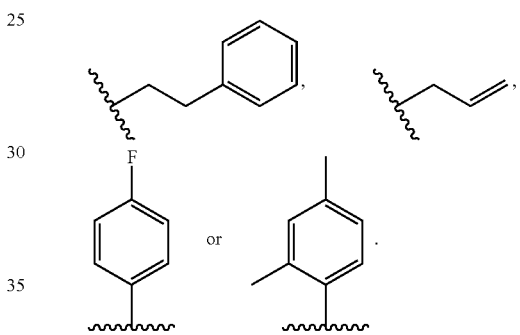

In a further embodiment, $R^{33b}$ is alkyl, for example, alkyl substituted with aryloxy, for example, naphthyloxy or phenoxy, such as halogen (e.g., bromine) substituted phenoxy, alkyl (e.g., methyl) substituted phenoxy or alkoxy (e.g., methoxy) substituted phenoxy. In another embodiment $R^{33b}$ is a thiol substituted alkyl (e.g., arylalkylthioalkyl, such as phenyl substituted alkylthioalkyl in which the phenyl may be further substituted with halogen, for example chlorine); a heterocyclic substituted alkyl (e.g., alkyl substituted with

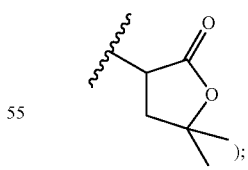

aryl substituted alkyl, for example, phenyl substituted alkyl (e.g., unsubstituted phenyl or phenyl substituted with halogen, such as chlorine, or phenyl substituted with alkoxy, such as isopropoxy). Alternatively, $R^{33b}$ is aryl, for example, thiophenyl or phenyl, for example, phenyl substituted with hydroxyl or alkoxy (e.g., methoxy). In another embodiment, $R^{33b}$ is selected from the group consisting of

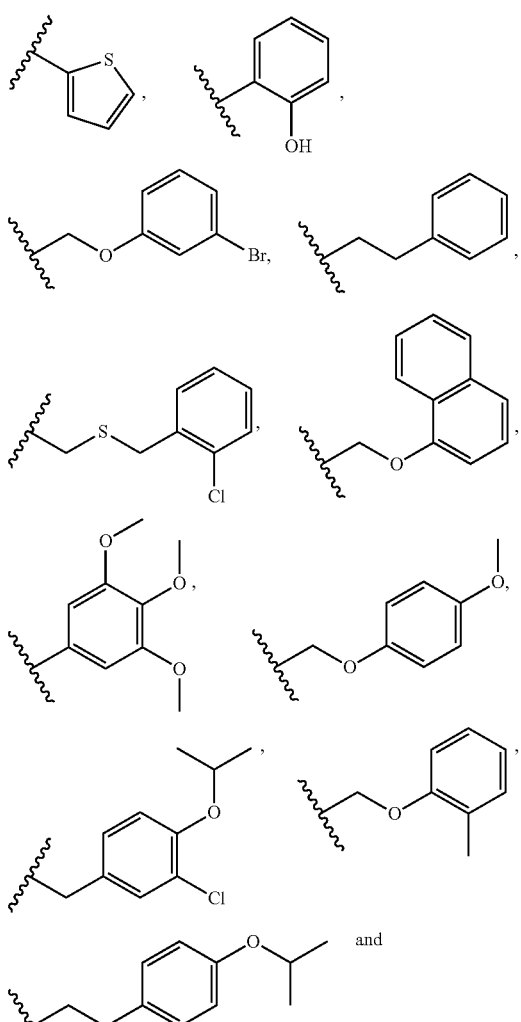

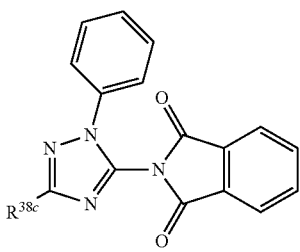

(VIIc)

wherein $R^{38c}$ is amino; and pharmaceutically acceptable salts thereof.

In one embodiment, $R^{38c}$ is substituted with carbonyl (e.g., carbonyl substituted with aryl, for example, phenyl, such as phenyl substituted with alkoxy, e.g., methoxy, or alkyl, for example, methyl) or sulfonyl (e.g., sulfonyl substituted with aryl, for example, phenyl, which may be substituted with alkyl, for example, methyl). In one embodiment, $R^{38c}$ is

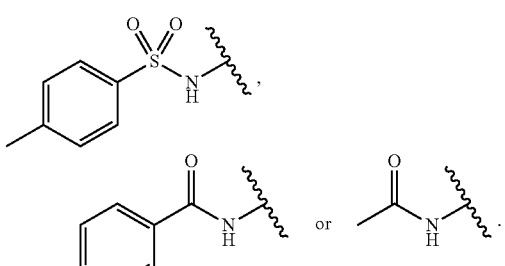

In a further embodiment, the RNA binding modulatory compound of formula VII is a compound of formula VIId:

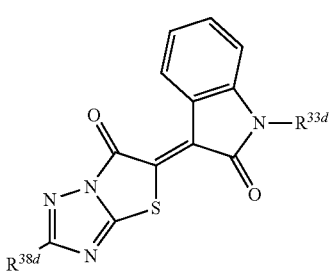

(VIId)

wherein $R^{33d}$ is alkyl; and $R^{38d}$ is aryl or amino; and pharmaceutically acceptable salts thereof.

In one embodiment, $R^{33d}$ is n-butyl. In another embodiment, $R^{33d}$ is substituted alkyl, for example, carbonyl substituted alkyl, such as aminocarbonyl substituted alkyl (e.g., 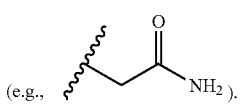 [SMILES: *CC(N)=O]).

In another embodiment, $R^{32b}$ and $R^{33b}$ are linked to form a 6-membered heterocyclic ring (e.g., 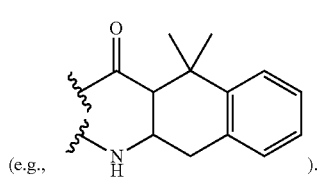).

In yet another embodiment, the RNA binding modulatory compound of formula VII is a compound of formula VIIIc:

In one embodiment, $R^{38d}$ is amino (e.g., amino substituted with carbonyl, for example, aryl substituted carbonyl, such as phenyl substituted carbonyl, including —$NO_2$ substituted phenyl) or aryl (e.g., phenyl, for example, phenyl substituted with carbonyloxy, such as alkyl substituted carbonyloxy, including, but not limited to methyl substituted carbonyloxy). In one embodiment, $R^{38d}$ is

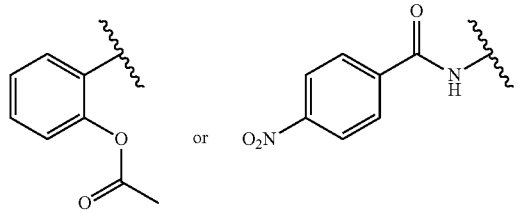

In a further embodiment, the RNA binding modulatory compound of formula VII is a compound of formula VIIe:

(VIIe)

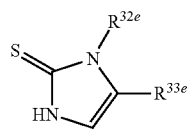

wherein $R^{32e}$ is hydrogen, alkyl or aryl; and $R^{33e}$ is aryl; and pharmaceutically acceptable salts thereof.

In one embodiment, $R^{32e}$ is hydrogen, alkyl (e.g., methyl, ethyl or aryl substituted alkyl, for example, phenyl substituted alkyl) or aryl (e.g., phenyl, for example, phenyl substituted with alkyl, such as methyl or ethyl, for example,

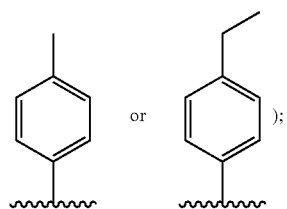

$R^{33e}$ is aryl such as furanyl or phenyl, for example, phenyl substituted with hydroxyl, halogen (e.g., bromine or chlorine) and alkoxy (e.g., methoxy). In one embodiment, $R^{33e}$ is

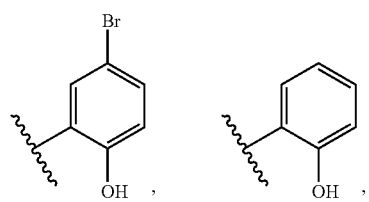

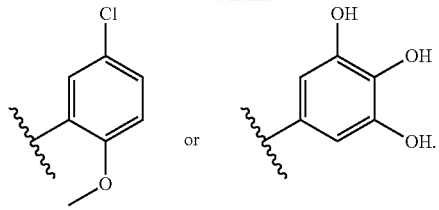

In one embodiment, the RNA binding modulatory compound of formula VII is a compound of formula VIIf:

(VIIf)

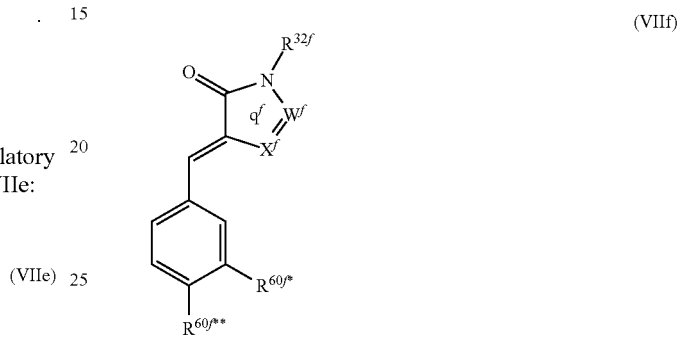

wherein $NR^{32f}$ is aryl;

$q^f$ is a single or double bond;

$W^f$ is NH when $q^f$ is a single bond; or N when $q^f$ is a double bond;

$X^f$ is C=O is when $q^f$ is a single bond; or $CR^{34f}$ when $q^f$ is a double bond;

$R^{34f}$ is alkyl;

$R^{60f*}$ is hydrogen, alkoxy or carbonyloxy; and $R^{60f**}$ is hydrogen or carbonyloxy; and pharmaceutically acceptable salts thereof.

In one embodiment, $q^f$ is a double bond, $X^f$ is $CR^{34f}$; $W^f$ is N; $R^{34f}$ is alkyl (e.g., methyl); $R^{32f}$ is phenyl substituted with sulfonyl (e.g., amino substituted sulfonyl), carboxylate or halogen (e.g., chlorine), such as

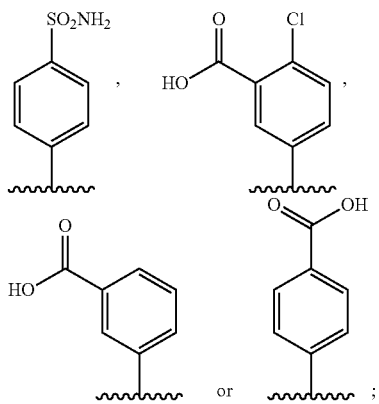

$R^{60f*}$ is hydrogen or alkoxy (e.g., methoxy or ethoxy) and $R^{60f**}$ is carbonyloxy, for example, aryl substituted carbonyloxy, such as furanyl or thiophenyl substituted carbonyloxy.

In another embodiment, $q^f$ is a single bond, $W^f$ is NH; $X^f$ is C=O; $R^{32f}$ is phenyl, such as unsubstituted phenyl or phenyl substituted with halogen (e.g., chlorine or fluorine) or carbonyl, for example, carbonyl substituted with alkoxy (e.g., ethoxy), for example,

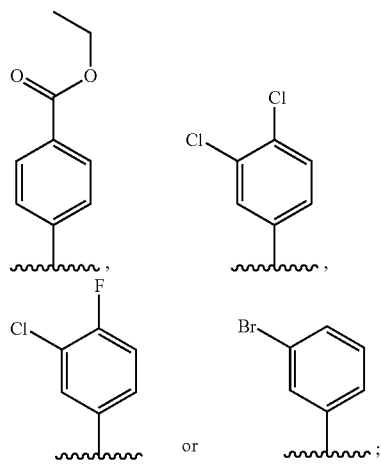

$R^{60f*}$ is hydrogen, alkoxy (e.g., methoxy) or carbonyloxy, for example, aryl substituted carbonyloxy, such as furanyl or thiophenyl substituted carbonyloxy; and $R^{60f**}$ is hydrogen or carbonyloxy, for example, aryl substituted carbonyloxy, such as furanyl or thiophenyl substituted carbonyloxy.

In another embodiment, the RNA binding modulatory compound of formula VII is a compound is selected from the group consisting of:

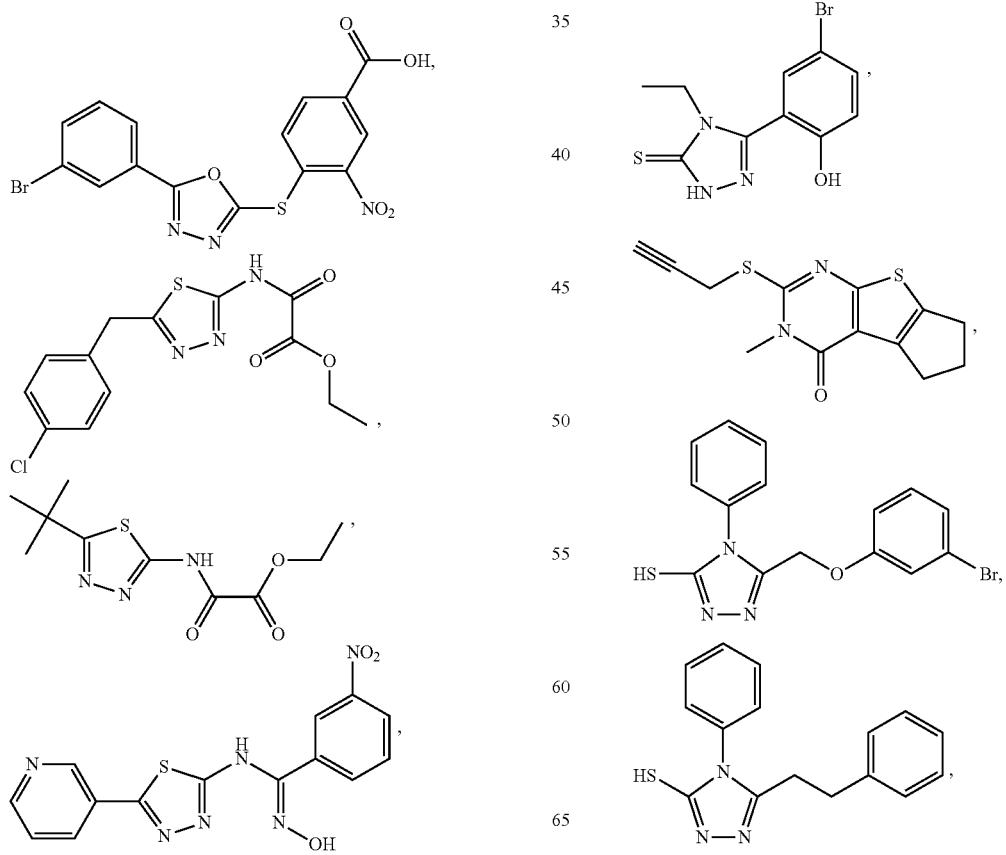

-continued

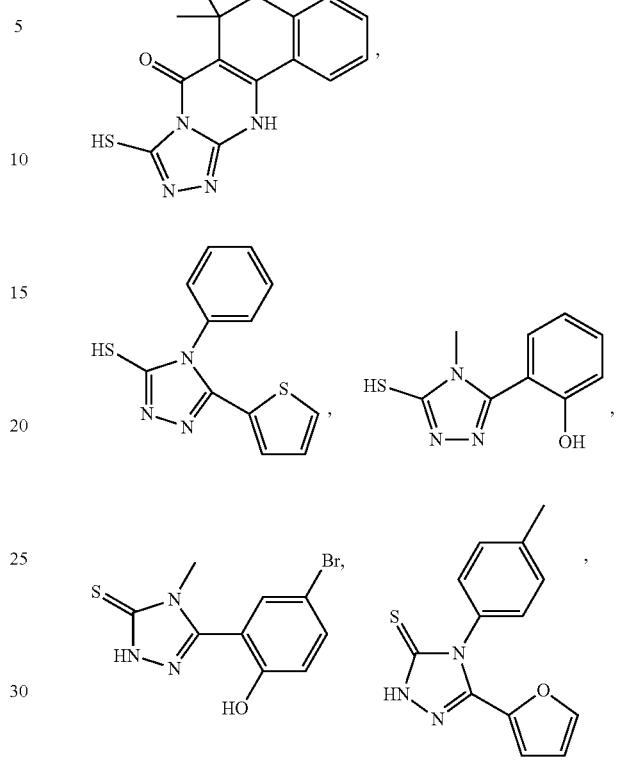

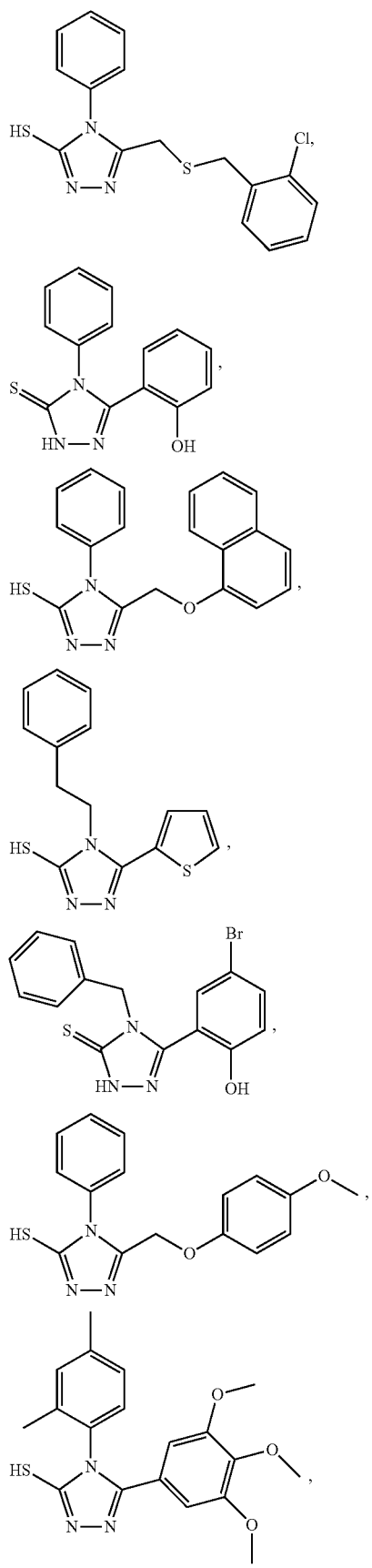
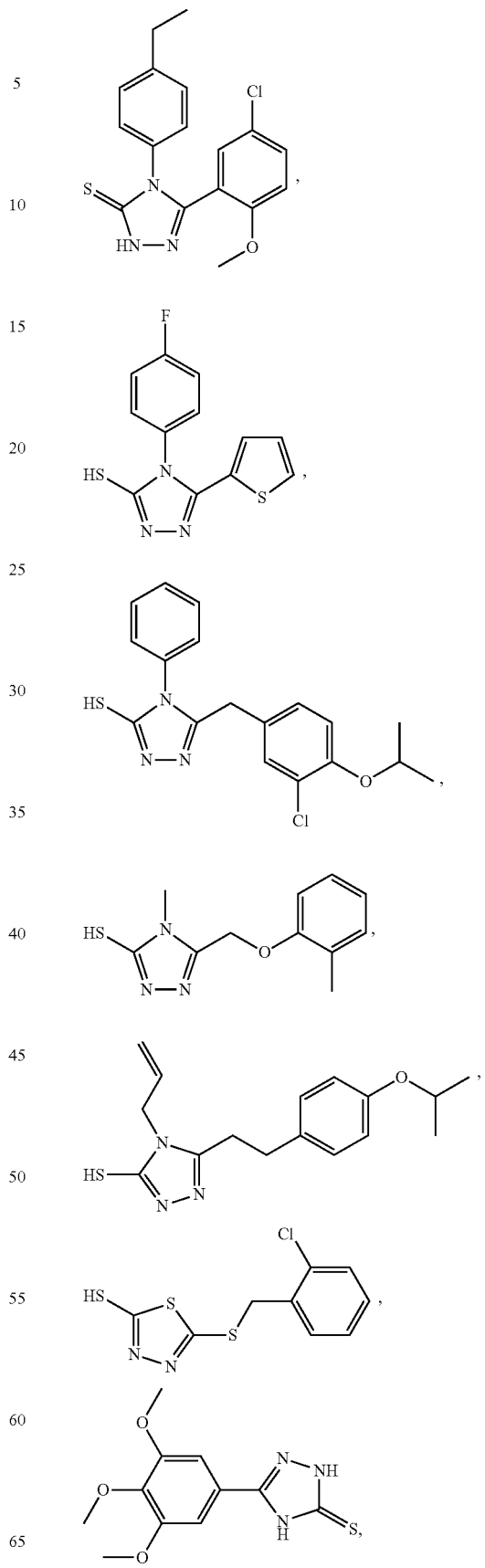

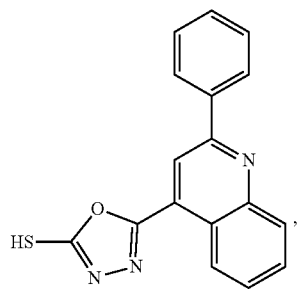
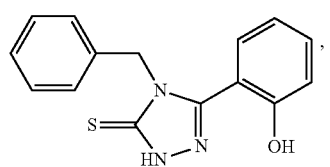
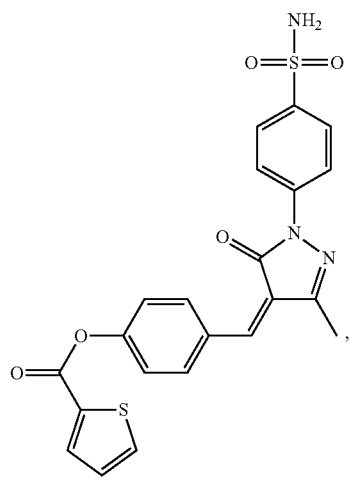
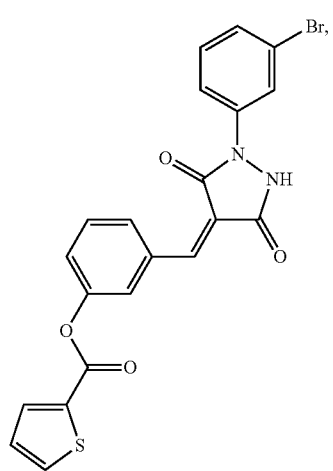
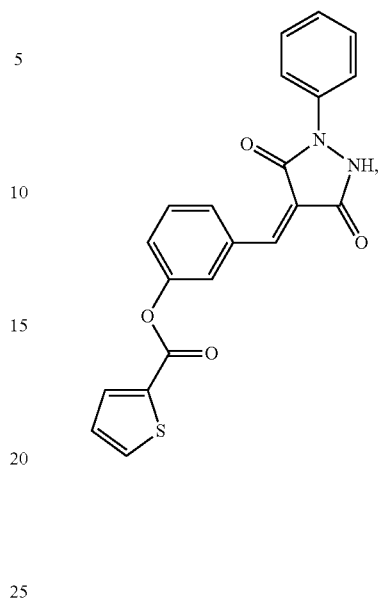
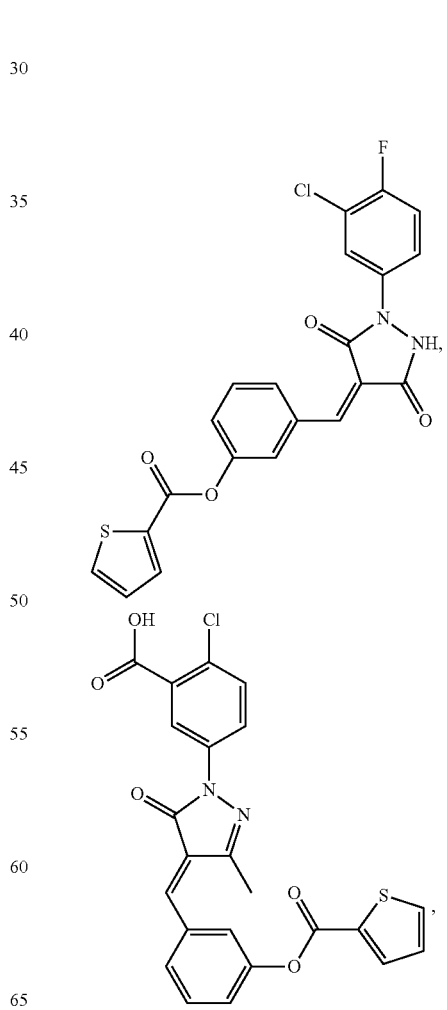

75
-continued
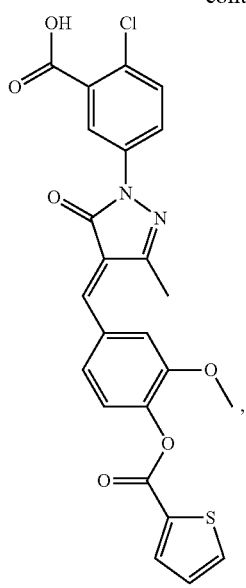
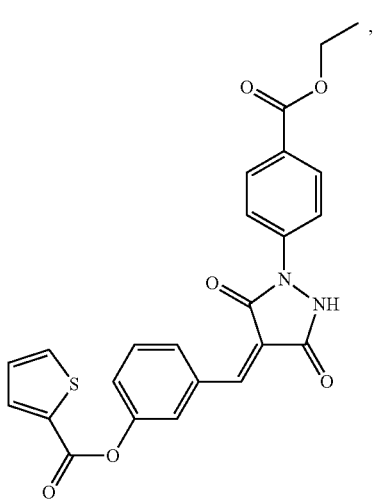
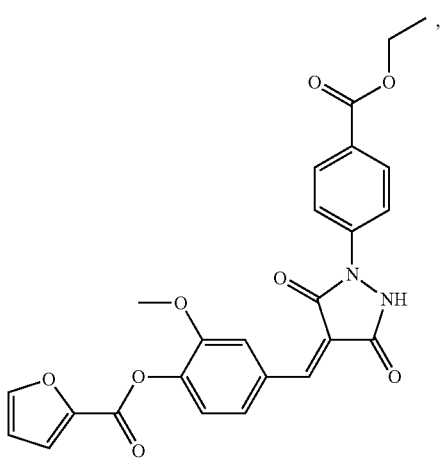
76
-continued
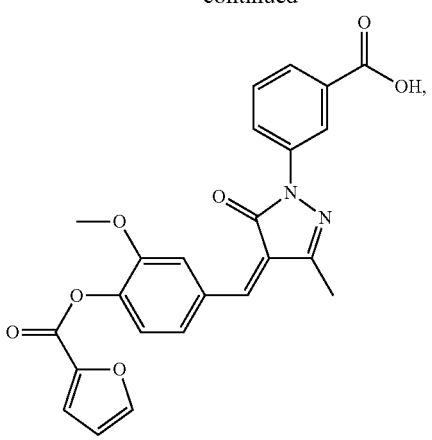
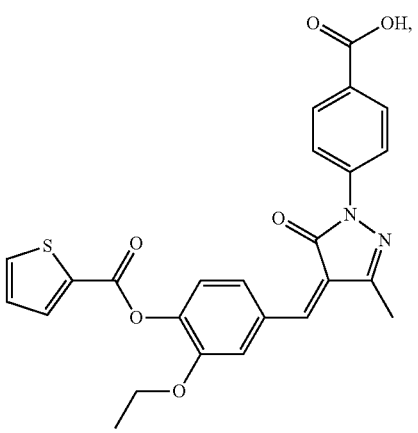
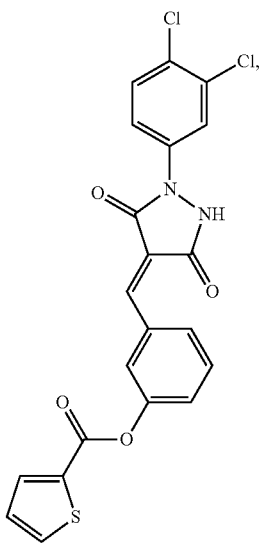

77
-continued
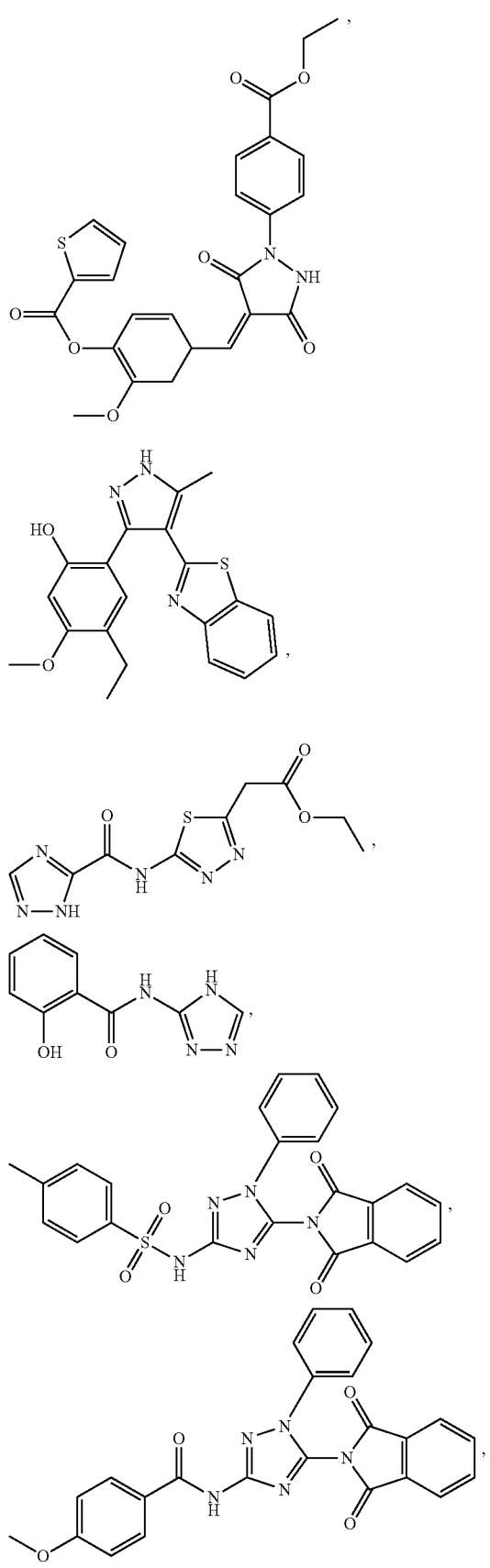
78
-continued
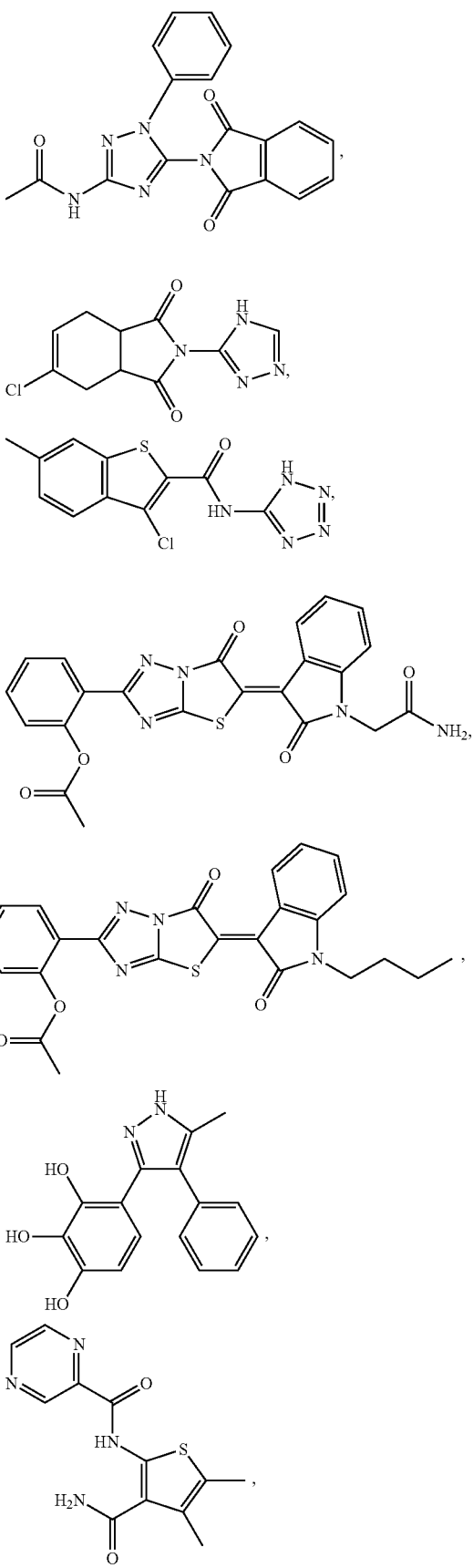

79
-continued
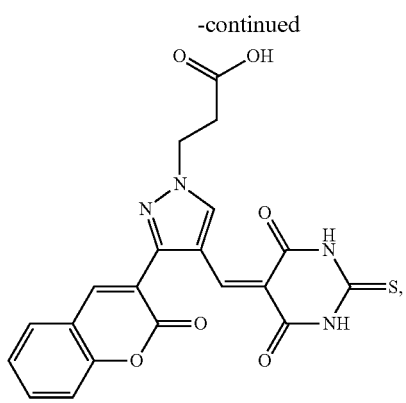
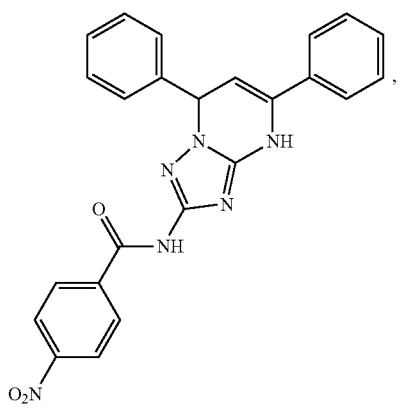
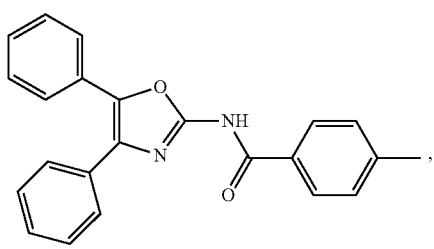
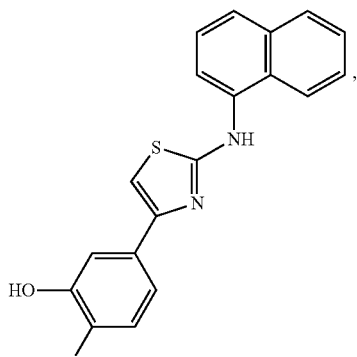
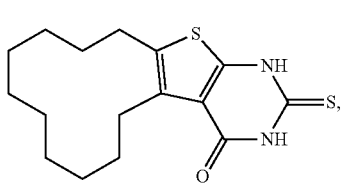
80
-continued
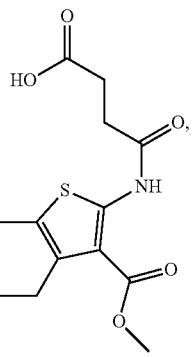
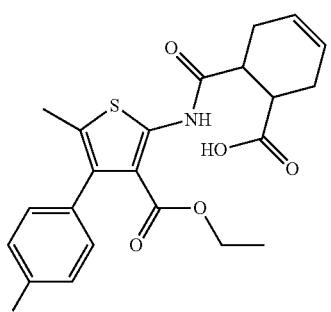
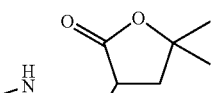 and
and pharmaceutically acceptable salts thereof.
In yet another embodiment, the RNA binding modulatory compound is a compound of Table 1:
TABLE 1
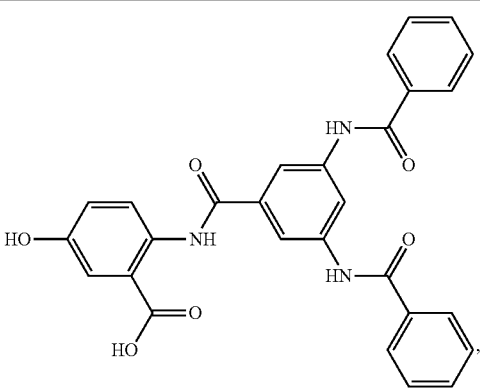 [SMILES: O=C(Nc1cc(NC(=O)c2ccccc2)cc(C(=O)Nc2ccc(O)cc2C(=O)O)c1)c1ccccc1]

TABLE 1-continued
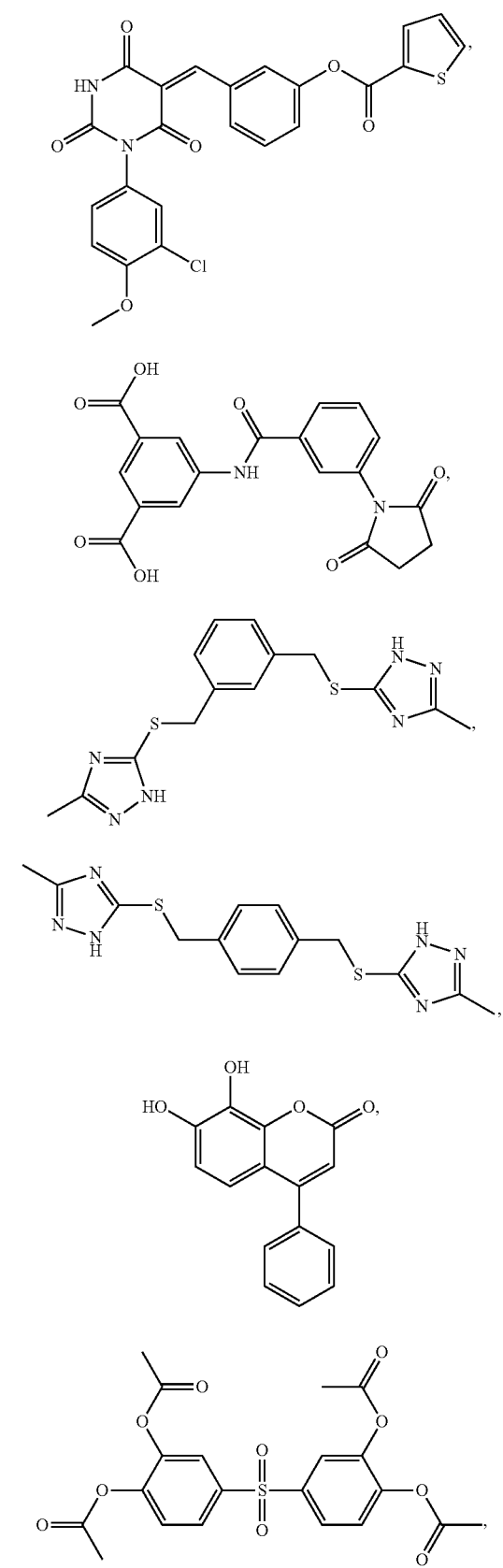
TABLE 1-continued
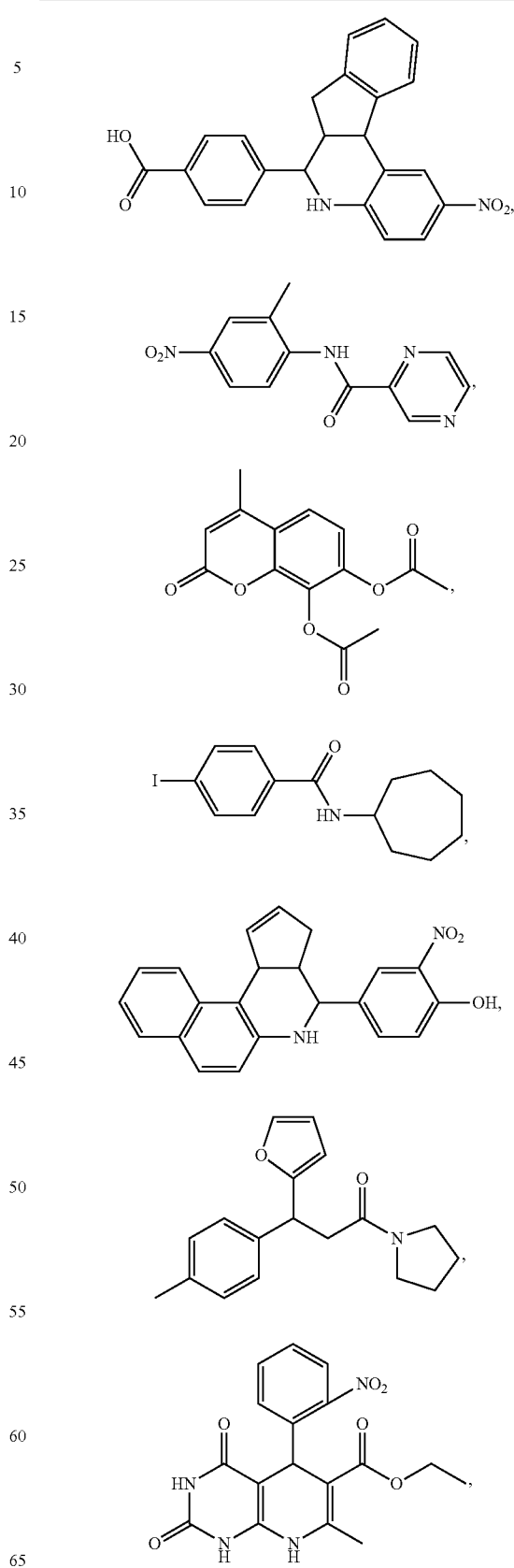

TABLE 1-continued

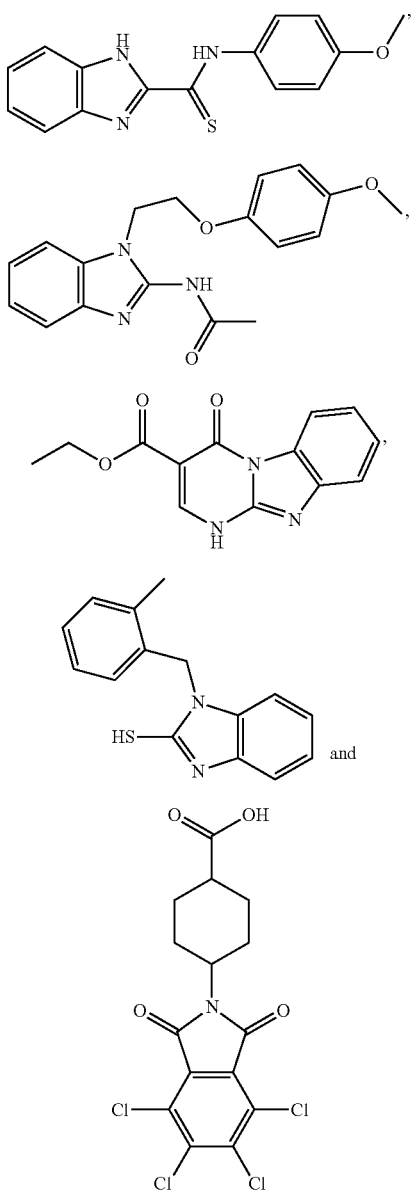

and pharmaceutically acceptable salts thereof.

In one embodiment, the compound is not abamectin, praziquantel, albendazole, diethylcarbamazine, mebendazole, niclosamide, ivermectin, suramin, thiabendazole, pyrantel pamoate, levamisole, triclabendazole, flubendazole, fenbendazole, octadepsipeptide, oxamniquine, metrifonate, bithionol, niridazole, stibophen, ciclobendazole, oxantel, pyrvinium, bephenium, desapidin or dichlorophen.

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclobutyl, cyclopentyl, cyclohexyl, cycloheptyl, cyclooctyl), alkyl substituted cycloalkyl groups, and cycloalkyl substituted alkyl groups. The term alkyl further includes alkyl groups that may include oxygen, nitrogen, sulfur or phosphorous atoms replacing one or more carbons of the hydrocarbon backbone.

In certain embodiments, a straight chain or branched chain alkyl has 6 or fewer carbon atoms in its backbone (e.g., $C_1$-$C_6$ for straight chain, $C_3$-$C_6$ for branched chain). Likewise, cycloalkyls may have from 3-8 carbon atoms in their ring structure. The term "$C_1$-$C_6$" includes alkyl groups containing 1 to 6 carbon atoms.

Moreover, the term alkyl includes both "unsubstituted alkyls" and "substituted alkyls," the latter of which refers to alkyl moieties having substituents replacing a hydrogen on one or more carbons of the hydrocarbon backbone. Such substituents can include, for example, alkyl, alkenyl, alkynyl, halogen, hydroxyl, aryl, alkylcarbonyloxy, arylcarbonyloxy, alkoxycarbonyloxy, aryloxycarbonyloxy, —COOH, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonate, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "arylalkyl" moiety is an alkyl substituted with an aryl (e.g., phenylmethyl (benzyl)). The term "alkyl" also includes the side chains of natural and unnatural amino acids.

The term "aryl" includes groups, e.g., 5- and 6-membered single-ring aromatic groups, that may include from zero to four heteroatoms, for example, benzene, phenyl, pyrrole, furan, thiophene, thiazole, isothiaozole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles," "heteroaryls" or "heteroaromatics." The aromatic ring can be substituted at one or more ring positions with such substituents as described above, as for example, alkyl, alkenyl, alkynyl, halogen, hydroxyl, alkoxy, aryl, alkylcarbonyloxy, arylcarbonyloxy, alkoxycarbonyloxy, aryloxycarbonyloxy, —COOH, alkylcarbonyl, alkylaminoacarbonyl, arylalkyl aminocarbonyl, alkenylaminocarbonyl, alkylcarbonyl, arylcarbonyl, arylalkylcarbonyl, alkenylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin). The term heteroaryl includes unsaturated cyclic compounds such as azirine, oxirene, dithiete, pyrroline, pyrrole, furan, dihydrofuran, dihydrothiophene, thiophene, pyrazole, imidazole, oxazole, thiazole, isothiazole, 12,2,3-triazole, 1,2,4, triazole, dithiazole, tetrazole, pyridine, pyran, pyrimidine, pyran, thiapyrane, diazine, thiazine, dioxine, triazine and tetrazene.

The term "heterocyclic moiety" includes saturated cyclic moieties having a closed ring of atoms in which at least one atom is not a carbon. As used herein, heterocyclic moieties do not include heteroaryl moieties, in which the closed ring of atoms is both heterocyclic and aromatic and/or unsaturated. Examples of heterocyclic moieties include aziridine, ethylene oxide, thiirane, dioxirane, azetidine, oxetane, thietane, dioxetane, dithietane, pyrrolidine, tetrahydrofuran, tetrahydrothiophene, imidazolidine, oxazolidine, thiazolidine, dioxolane, dithiolane, piperidine, tetrahydropyran, thiane, piperzine, pxazine, dithiane, dioxane and trioxane.

The term "heterocyclic moiety" includes both "unsubstituted heterocyclic moieties" and "substituted heterocyclic moieties," the latter of which includes moieties having substituents replacing a hydrogen on one or more of the atoms on the closed ring. Such substituents can include, for example, alkyl, alkenyl, alkynyl, halogens, hydroxyl, aryl alkylcarbonyloxy, arylcarbonyloxy, alkoxycarbonyl oxy, aryloxycarbonyloxy, —COOH, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkenyl" includes unsaturated aliphatic groups analogous in length and possible substitution to the alkyls described above, but that contain at least one double bond. For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclobutenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term "alkenyl" further includes alkenyl groups which include oxygen, nitrogen, sulfur or phosphorous atoms replacing one or more carbons of the hydrocarbon backbone. In certain embodiments, a straight chain or branched chain alkenyl group has 6 or fewer carbon atoms in its backbone (e.g., $C_2$-$C_6$ or straight chain, $C_3$-$C_6$ for branched chain). Likewise, cycloalkenyl groups may have from 3-8 carbon atoms in their ring structure. The term $C_2$-$C_6$ includes alkenyl groups containing 2 to 6 carbon atoms.

Moreover, the term "alkenyl" includes both "unsubstituted alkenyls" and "substituted alkenyls," the latter of which refers to alkenyl moieties having substituents replacing a hydrogen on one or more carbons of the hydrocarbon backbone. Such substituents can include, for example, alkyl, alkenyl, alkynyl, halogens, hydroxyl, aryl alkylcarbonyloxy, arylcarbonyloxy, alkoxycarbonyl oxy, aryloxycarbonyloxy, —COOH, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond. For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term "alkynyl" further includes alkynyl groups which include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

Moreover, the term "alkynyl" includes both "unsubstituted alkynyls" and "substituted alkynyls," the latter of which refers to alkynyl moieties having substituents replacing a hydrogen on one or more carbons of the hydrocarbon backbone. Such substituents can include, for example, alkyl, alkenyl, alkynyl, halogens, hydroxyl, aryl, alkylcarbonyloxy, arylcarbonyloxy, alkoxycarbonyloxy, aryloxycarbonyloxy, —COOH, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "acyl" includes compounds and moieties which contain the acyl radical ($CH_3CO$—). It also includes substituted acyl moieties. The term "substituted acyl" includes acyl groups where one or more of the hydrogen atoms are replaced by for example, alkyl, alkenyl, alkynyl, halogens, hydroxyl, aryl, alkylcarbonyloxy, arylcarbonyloxy, alkoxycarbonyloxy, aryloxycarbonyloxy, —COOH, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "acylamino" includes moieties wherein: an acyl moiety is bonded to an amino group. For example, the term includes alkylcarbonylamino, arylcarbonylamino, carbamoyl and ureido groups.

The terms "alkoxyalkyl," "alkylaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups.

Examples of substituted alkoxy groups include halogenated alkoxy groups. The alkoxy groups can be substituted with groups such as alkyl, alkenyl, alkynyl, halogen, hydroxyl, aryl, alkylcarbonyloxy, arylcarbonyloxy, alkoxycarbonyloxy, aryloxycarbonyloxy, —COOH, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphinato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "amine" or "amino" includes compounds where a nitrogen atom is covalently bonded to at least one carbon or heteroatom. The term includes "alkyl amino" which comprises groups and compounds wherein: the nitrogen is bound to at least one additional alkyl group. The term "dialkyl amino" includes groups wherein: the nitrogen atom is bound to at least two additional alkyl groups. The term "arylamino" and "diarylamino" include groups in which the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkaminoalkyl" refers to an alkyl, alkenyl, or alkynyl group bound to a nitrogen atom which is also bound to an alkyl group.

The term "amide," "amido" or "aminocarbonyl'" includes compounds or moieties which contain a nitrogen atom which is bound to the carbon of a carbonyl or a thiocarbonyl group. The term includes "alkaminocarbonyl" or "alkylaminocarbonyl" groups which include alkyl, alkenyl, aryl or alkynyl groups bound to an amino group bound to a carbonyl group. It includes arylaminocarbonyl and arylcarbonylamino groups, which include aryl or heteroaryl moieties bound to an amino group that is bound to the carbon of a carbonyl or thiocarbonyl group. The terms "alkylaminocarbonyl," "alkenylaminocarbonyl," "alkynylaminocarbonyl," "arylaminocarbonyl," "alkylcarbonylamino," "alkenyl carbonylamino," "alkynylcarbonylamino," and "arylcarbonylamino" are included in term "amide." Amides also include urea groups (aminocarbonylamino) and carbamates (oxycarbonylamino).

The term "carbonyl" or "carboxy" includes compounds and moieties which contain a carbon connected with a double bond to an oxygen atom. The carbonyl can be further substituted with any moiety which allows the compounds of the invention to perform its intended function. For example, carbonyl moieties may be substituted with alkyls, alkenyls, alkynyls, aryls, alkoxy, aminos, etc. Examples of moieties which contain a carbonyl include aldehydes, ketones, carboxylic acids, amides, esters, anhydrides, etc. The term "carboxy" further includes the structure of —COOH and —COO$^-$.

The term "oximyl" includes compounds and moieties that contain a carbon connected with a double bond to a nitrogen atom, which is, in turn connected to a hydroxyl or an alkoxyl group. The term "hydrazinyl" includes compounds and moieties that contain a carbon connected with a double bond to a nitrogen atom, which is, in turn, connected to an amino group.

The term "thiocarbonyl" or "thiocarboxy" includes compounds and moieties which contain a carbon connected with a double bond to a sulfur atom.

The term "ether" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "thioether" includes compounds and moieties which contain a sulfur atom bonded to two different carbon or hetero atoms. Examples of thioethers include, but are not limited to, alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and "alkthioalkynyl" refer to compounds or moieties in which an alkyl, alkenyl or alkynyl group is bonded to a sulfur atom that is covalently bonded to an alkenyl or alkynyl group, respectively.

The term "sulfonyl" includes moieties containing a sulfonyl functional group (e.g., $SO_2$) attached to two carbons via a covalent bond to the sulfur atom of the sulfonyl functional group.

The term "hydroxyl" or "hydroxyl" includes groups with an —OH or —O$^-$.

The term "halogen" includes fluorine, bromine, chlorine, iodine, etc.

The term "heteroatom" includes atoms of any element other than carbon or hydrogen. Preferred heteroatoms are nitrogen, oxygen, sulfur and phosphorus.

II. Screening Assays

The invention provides methods (also referred to herein as "screening assays") for identifying modulators, i.e., candidate or test compounds or agents (e.g., peptidomimetics, small molecules or other drugs) which modulate, for example one or more biological activities of an RNA-binding protein, e.g., the ability to 1) interact, e.g., bind, e.g., form a complex, with an RNA molecule, e.g., an RNA molecule comprising an RNA-binding recognition element of the RNA-binding protein, 2) modulate embryogenesis, 3) modulate cell viability, 4) modulate anterior patterning, 5) modulate germ cell totipotency, 6) modulate development of the intestine, 7) modulate development of germline blastomeres, 8) modulate development of pharyngeal tissue, 9) modulate expression and/or activity of a gene known to be directly or indirectly regulated by the RNA-binding protein, e.g., PAL-1, NOS-2, APX-1 protein, and GLD-1, 10) modulate tubercle formation, or for testing or optimizing the activity of such agents.

The assays can be used to identify agents that modulate the function of an RNA-binding protein or a molecule in a signal transduction pathway involving the RNA-binding protein. The function of an RNA-binding protein can be affected at any level, including transcription, protein expression, protein localization, and/or cellular activity. The subject assays can also be used to identify, e.g., agents that alter the interaction of an RNA-binding protein with a binding partner, e.g., an RNA molecule comprising an RNA-binding protein recognition element, or modulate, e.g., inhibit, the stability of such interaction.

The subject screening assays can measure the activity of an RNA-binding protein directly (e.g., formation of a complex with an RNA molecule comprising an RNA-binding protein recognition element), or can measure a downstream event controlled by modulation of the RNA-binding protein (e.g., embryogenesis, cell differentiation, expression and/or activity of, a gene known to be directly or indirectly regulated by the RNA-binding protein, e.g., PAL-1, NOS-2, APX-1 protein, and GLD-1).

The subject screening assays employ indicator compositions. These indicator compositions comprise the components required for performing an assay that detects and/or measures a particular event. The indicator compositions of the invention provide a reference readout and changes in the readout can be monitored in the presence of one or more test compounds. A difference in the readout in the presence and the absence of the compound indicates that the test compound is a modulator of the molecule(s) present in the indicator composition.

The indicator composition used in the screening assay can be a cell that expresses an RNA-binding protein and/or an RNA molecule comprising an RNA-binding protein recognition element. For example, a cell that naturally expresses or, more preferably, a cell that has been engineered to express the protein and/or the RNA molecule comprising an RNA-binding protein recognition element by introducing into the cell an expression vector encoding the protein may be used. The cell may be a helminth cell, a plant cell, a yeast cell, a bacterial cell, or a mammalian cell, e.g., a human cell. Alternatively, the indicator composition can be a cell-free composition that includes the protein and/or the RNA molecule comprising an RNA-binding protein recognition element (e.g., a cell extract or a composition that includes e.g., either purified natural or recombinant protein and/or RNA).

The indicator compositions used in the screening assays of the invention can be a cell that expresses an RNA-binding protein or biologically active fragment thereof, e.g., a fragment of the protein that interacts, e.g., binds, to an RNA-binding protein recognition element, e.g., a fragment comprising a CCCH-type tandem zinc finger or a KH domain.

In another embodiment, the indicator composition comprises more than one polypeptide. For example, in one embodiment the subject assays are performed in the presence of more than one RNA-binding protein, e.g., MEX-5, GLP-1, NOS-2, MEX-6, POS-1, MEX-3, PAL-1. It will be understood that in addition to the recited proteins, e.g., helminth proteins, e.g., nematode proteins, suitable proteins for use in the methods of the invention include plant and mammalian homologues of such proteins, e.g., TTP, the mammalian homologue of MEX-5. One of ordinary skill in the art can identify such proteins based on sequence and/or database and/or homology searching and analyses.

Compounds that modulate the expression and/or activity of an RNA-binding protein, identified using the assays described herein can be useful for treating a subject that would benefit from the modulation of expression and/or activity of the RNA-binding protein, e.g., a subject with a parasitic associate state.

In one embodiment, secondary assays can be used to confirm that the modulating agent affects the RNA-binding protein molecule in a specific manner. For example, compounds identified in a primary screening assay can be used in a secondary, tertiary, etc. screening assay to determine whether the compound affects an RNA-binding protein-related activity as described herein. Accordingly, in another aspect, the invention pertains to a combination of two or more of the assays described herein. For example, a modulating agent can be identified using a cell-based or a cell-free assay, e.g., to detect an interaction, e.g., formation of a complex, and the ability of the agent to modulate the activity of the RNA-binding protein or a molecule involved in a signal transduction pathway involving the RNA-binding protein can be confirmed using a biological read-out to measure, e.g., embryogenesis, an immune response, e.g., cytokine production, in vitro or in vivo.

Moreover, a modulator of an RNA-binding protein expression and/or activity identified as described herein (e.g., a small molecule) may be used in an animal model and/or plant model to determine the efficacy, toxicity, or side effects of treatment with such a modulator. Alternatively, a modulator identified as described herein may be used in an animal model to determine the mechanism of action of such a modulator. An example of a nematode parasite model that may be used to evaluate the efficacy of treatment of nematode parasitism with an RNA binding modulatory compound identified herein is described, for example, in Lok J. B. ("*Strongyloides stercoralis*: a model for translational research on parasitic nematode biology" 2007 WormBook, ed. The *C. elegans* Research Community, WormBook, doi/10.1895/wormbook.1.134.1, at www.wormbook.org), the entire contents of which is incorporated herein by reference. *S. stercoralis* is a significant pathogen of humans and can be maintained in laboratory dogs and gerbils. Examples of animal models that may be used to determine the efficacy of treatment of nematode parasitism with an RNA binding modulatory compound identified herein are described, for example, in Camberis, M. et al., (*Animal Model of Nippostrongylus brasiliensis and Heligmosomoides polygyrus,* 2003 Current Protocols in Immunology 19.12.1-19.12.27), the entire contents of which is incorporated herein by reference.

In one embodiment, the screening assays of the invention are high throughput or ultra high throughput (e.g., Fernandes, P. B., Curr Opin Chem. Biol. 1998 2:597; Sundberg, S A, Curr Opin Biotechnol. 2000, 11:47).

Exemplary cell based and cell free assays of the invention are described in more detail below.

Cell Based Assays

The indicator compositions of the invention may be cells that express an RNA-binding protein and/or an RNA molecule comprising an RNA-binding protein recognition element. For example, a cell that naturally expresses endogenous polypeptide and/or RNA molecule, or, more preferably, a cell that has been engineered to express one or more exogenous polypeptides and/or RNA molecules, e.g., by introducing into the cell an expression vector encoding the protein may be used in a cell based assay.

The cells used in the instant assays can be eukaryotic or prokaryotic in origin. For example, in one embodiment, the cell is a bacterial cell. In one embodiment, the cell is a helminth, e.g., nematode, cell. In another embodiment, the cell is a plant cell. In another embodiment, the cell is a fungal cell, e.g., a yeast cell. In another embodiment, the cell is a vertebrate cell, e.g., an avian or a mammalian cell (e.g., a murine cell, rat cell, rhesus monkey, or a human cell). In another embodiment, the cell is a human cell.

In another embodiment, cells for use in the methods of the invention are derived from a cell line, preferably one which expresses low levels of endogenous RNA-binding protein and/or an RNA molecule comprising an RNA-binding protein recognition element and is then engineered to express recombinant protein and/or RNA.

Recombinant expression vectors that may be used for expression of polypeptides are known in the art. For example, the cDNA is first introduced into a recombinant expression vector using standard molecular biology techniques. A cDNA can be obtained, for example, by amplification using the polymerase chain reaction (PCR) or by screening an appropriate cDNA library.

When used in mammalian cells, the expression vector's control functions are often provided by viral regulatory elements. For example, commonly used promoters are derived from polyoma virus, adenovirus, cytomegalovirus and Simian Virus 40. Non-limiting examples of mammalian expression vectors include pCDM8 (Seed, B., (1987) Nature 329: 840) and pMT2PC (Kaufman, et al. (1987), EMBO J. 6:187-195). A variety of mammalian expression vectors carrying different regulatory sequences are commercially available.

Vector DNA may be introduced into cells via conventional transfection techniques. As used herein, the various forms of the term "transfection" are intended to refer to a variety of art-recognized techniques for introducing foreign nucleic acid (e.g., DNA) into host cells, including calcium phosphate co-precipitation, DEAE-dextran-mediated transfection, lipofection, or electroporation. Suitable methods for transfecting host cells can be found in Sambrook, et al. (Molecular Cloning: A Laboratory Manual, 2nd Edition, Cold Spring Harbor Laboratory press (1989)), and other laboratory manuals.

For stable transfection of cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on a separate vector from that encoding an RNA-binding protein and/or an RNA molecule comprising an RNA-binding protein recognition element, on the same vector. Cells stably transfected with the introduced nucleic acid can be identified by drug selection (e.g., cells that have incorporated the selectable marker gene will survive, while the other cells die).

In one embodiment, within the expression vector coding sequences are operatively linked to regulatory sequences that allow for constitutive expression of the molecule in the indicator cell (e.g., viral regulatory sequences, such as a cytomegalovirus promoter/enhancer, may be used). Use of a recombinant expression vector that allows for constitutive expression of the genes in the indicator cell is preferred for identification of compounds that enhance or inhibit the activity of the molecule. In an alternative embodiment, within the expression vector the coding sequences are operatively linked to regulatory sequences of the endogenous gene (i.e., the promoter regulatory region derived from the endogenous gene). Use of a recombinant expression vector in which expression is controlled by the endogenous regulatory sequences is preferred for identification of compounds that enhance or inhibit the transcriptional expression of the molecule.

For example, an indicator cell can be transfected with an expression vector comprising an RNA-binding protein, or biologically active fragment thereof, incubated in the presence and in the absence of a test compound, and the effect of the compound on the expression and/or activity of the molecule or on a biological response regulated by the RNA-binding protein, e.g., an RNA-binding protein-related activity, can be determined. The biological activities of an RNA-binding protein include activities determined in vivo, or in vitro, according to standard techniques. Activity can be a direct activity, such as an association with a target molecule (e.g., an RNA molecule comprising an RNA-binding protein recognition element). Alternatively, activity may be an indirect activity, such as, for example, a cellular signaling activity occurring downstream of the interaction of the protein with a target molecule or a biological effect occurring as a result of the signaling cascade triggered by that interaction, such as embryogenesis and/or cell differentiation.

Compounds that modulate RNA-binding protein production, expression and/or activity of may be identified using various "read-outs."

For example, in one embodiment, gene expression of an RNA-binding protein can be measured. In another embodiment, expression of a gene controlled by an RNA-binding protein can be measured.

In another embodiment, protein expression may be measured. For example, standard techniques such as Western blotting or in situ detection can be used.

In one embodiment a downstream effect of modulation of an RNA-binding protein, e.g., the effect of a compound on cell viability and/or embryogenesis, and/or tubercle formation in a plant, may be used as an indicator of modulation of the activity of an RNA-binding protein by, for example, monitoring directly (e.g. by microscopic examination of the cells), or indirectly, e.g., by monitoring one or more markers of, for example, embryogenesis.

Standard methods for detecting mRNA of interest, such as reverse transcription-polymerase chain reaction (RT-PCR) and Northern blotting, are known in the art. Standard methods for detecting protein secretion in culture supernatants, such as enzyme linked immunosorbent assays (ELISA), are also known in the art. Proteins can also be detected using antibodies, e.g., in an immunoprecipitation reaction or for staining and FACS analysis.

The ability of the test compound to modulate an RNA-binding molecule interaction with a target molecule can also be determined. For example, in one embodiment, the interaction of an RNA-binding molecule and an RNA molecule comprising an RNA-binding protein recognition element can be measured as described in, for example, Pagano, et al. (2007) J. Biol. Chem. 282:8883 and Farley, et al. (2008) RNA 14: 2685. In certain embodiments of the invention, the RNA-binding protein recognition element comprises the consensus sequence $UA(U_{2-3})RD(N_{1-3})G$. In still other embodiments of the invention, the RNA-binding protein recognition element comprises the consensus sequence $DKAG(N_{0-3})UHUA$. In one embodiment, the RNA-binding protein recognition element, i.e., $DKAG(N_{0-3})UHUA$, binds with MEX-3. In another embodiment, the RNA-binding protein recognition element, i.e., $UA(U_{2-3})RD(N_{1-3})G$, binds with POS-1.

Determining the ability of the test compound to modulate, for example, an RNA-binding molecule, binding to a target molecule (e.g., a target RNA molecule, e.g., an RNA-binding protein recognition element) can also be accomplished, for example, by determining the ability of the molecules to be coimmunoprecipitated or by coupling the target molecule with a radioisotope or enzymatic label such that binding of the target molecule to an RNA-binding molecule or an RNA-binding molecule-interacting polypeptide can be determined, e.g., by detecting the labeled target molecule in a complex. Alternatively, for example, an RNA-binding molecule can be coupled with a radioisotope or enzymatic label to monitor the ability of a test compound to modulate an RNA-binding molecule binding to a target molecule in a complex.

Determining the ability of the test compound to interact with an RNA-binding molecule can be accomplished, for example, by coupling the compound with a radioisotope or enzymatic label such that interaction of the compound can be determined by detecting the labeled compound in a complex. For example, targets can be labeled with 125I, 35S, 14C, or 3H, either directly or indirectly, and the radioisotope detected by direct counting of radioemmission or by scintillation counting. Alternatively, compounds can be labeled, e.g., with, for example, horseradish peroxidase, alkaline phosphatase, or luciferase, and the enzymatic label detected by determination of conversion of an appropriate substrate to product.

In another embodiment, fluorescence technologies can be used, e.g., fluorescence polarization, time-resolved fluorescence, and fluorescence resonance energy transfer (Selvin, P R, Nat. Struct. Biol. 2000 7:730; Hertzberg R P and Pope A J, Curr Opin Chem Biol. 2000 4:445).

It is also within the scope of this invention to determine the ability of a compound to interact with an RNA-binding protein without the labeling of any of the interactants. For example, a microphysiometer may be used to detect the interaction of a compound with a an RNA-binding protein without the labeling of either the compound or the molecule (McConnell, H. M., et al. (1992) Science 257:1906-1912). As used herein, a "microphysiometer" (e.g., Cytosensor) is an analytical instrument that measures the rate at which a cell acidifies its environment using a light-addressable potentiometric sensor (LAPS). Changes in this acidification rate may be used as an indicator of the interaction between compounds.

In yet another aspect of the invention, an RNA-binding protein or fragments thereof may be used as "bait protein" e.g., in a two-hybrid assay or three-hybrid assay (see, e.g., U.S. Pat. No. 5,283,317; Zervos, et al. (1993) Cell 72:223-232; Madura, et al. (11993) J. Biol. Chem. 268:12046-12054; Bartel, et al. (1993) Biotechniques 14:920-924; Iwabuchi, et al. (1993) Oncogene 8: 1693-1696; and Brent WO94/10300), to identify other proteins, which bind to or interact with an RNA-binding protein ("binding proteins" or "bp") and are involved in an RNA-binding protein activity. Such proteins are also likely to be involved in the propagation of signals by the RNA-binding protein. The two-hybrid system is based on the modular nature of most transcription factors, which consist of separable DNA-binding and activation domains. Briefly, the assay utilizes two different DNA constructs. In one construct, the gene that codes for an RNA-binding protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming an RNA-binding protein-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the RNA-binding protein.

Cell-Free Assays

Alternatively, the indicator composition can be a cell-free composition that includes an RNA-binding protein, e.g., a cell extract from a cell expressing the protein or a composition that includes purified either natural or recombinant protein.

In one embodiment, the indicator composition is a cell free composition. Polypeptides expressed by recombinant methods in a host cells or culture medium can be isolated from the host cells, or cell culture medium using standard methods for protein purification. For example, ion-exchange chromatography, gel filtration chromatography, ultrafiltration, electrophoresis, and immunoaffinity purification with antibodies may be used to produce a purified or semi-purified protein that may be used in a cell free composition. Alternatively, a lysate or an extract of cells expressing the protein of interest can be prepared for use as cell-free composition. Cell extracts with the appropriate post-translation modifications of proteins can be prepared using commercially available resources found at, for example Promega, Inc.

In one embodiment, compounds that specifically modulate an activity of an RNA-binding protein may be identified. For example, compounds that modulate an activity of an RNA-binding protein are identified based on their ability to modulate the interaction of an RNA-binding protein with a target molecule to which the RNA-binding protein binds, e.g., RNA molecule comprising an RNA-binding protein recognition element. Suitable assays are known in the art that allow for the detection of protein-protein interactions (e.g., immunoprecipitations and the like) or that allow for the detection of interactions between a DNA or RNA binding protein and a target DNA or RNA sequence (e.g., electrophoretic mobility shift assays, DNAse I footprinting assays and the like). By performing such assays in the presence and absence of test compounds, these assays may be used to identify compounds that modulate (e.g., inhibit or enhance) the interaction of an RNA-binding protein with a target molecule.

In the methods of the invention for identifying test compounds that modulate an interaction between an RNA-binding protein and a target molecule, the complete RNA-binding protein may be used in the method, or, alternatively, only portions of the protein may be used. For example, an isolated CCH-type tandem zinger finder domain or a KH domain may be used. An assay may be used to identify test compounds that either stimulate or inhibit the interaction between the an RNA-binding protein and a target molecule. A test compound that stimulates the interaction between the protein and a target molecule is identified based upon its ability to increase the degree of interaction as compared to the degree of interaction in the absence of the test compound and such a compound would be expected to, e.g., increase, the activity of an RNA-binding protein in the cell. A test compound that inhibits the interaction between the protein and a target molecule is identified based upon its ability to decrease the degree of interaction between the protein and a target molecule as compared to the degree of interaction in the absence of the compound and such a compound would be expected to, e.g., decrease, RNA-binding protein activity.

In one embodiment, the amount of binding of an RNA-binding protein to an RNA molecule comprising an RNA-binding protein recognition element in the presence of the test compound is greater than the amount of binding in the absence of the test compound, in which case the test compound is identified as a compound that enhances binding of an RNA-binding protein to an RNA molecule comprising an RNA-binding protein recognition element. In another embodiment, the amount of binding of the RNA-binding protein to an RNA molecule comprising an RNA-binding protein recognition element in the presence of the test compound is less than the amount of binding of an RNA-binding protein to an RNA molecule comprising an RNA-binding protein recognition element in the absence of the test compound, in which case the test compound is identified as a compound that inhibits binding of an RNA-binding protein to an RNA molecule comprising an RNA-binding protein recognition element.

For example, interaction, e.g., formation of a complex, of the test compound to an RNA-binding protein can be determined either directly or indirectly as described above. Determining the ability of an RNA-binding protein to interact with a test compound can also be accomplished using a technology such as real-time Biomolecular Interaction Analysis (BIA) (Sjolander, S, and Urbaniczky, C. (1991) Anal. Chem. 63:2338-2345; Szabo, et al. (1995) Curr. Opin. Struct. Biol. 5:699-705). As used herein, "BIA" is a technology for studying biospecific interactions in real time, without labeling any of the interactants (e.g., BIAcore). Changes in the optical phenomenon of surface plasmon resonance (SPR) may be used as an indication of real-time reactions between biological molecules.

In one embodiment of the above assay methods, it may be desirable to immobilize either an RNA-binding protein or an RNA molecule comprising an RNA-binding protein recognition element for example, to facilitate separation of complexed from uncomplexed forms of one or both of the molecules, or to accommodate automation of the assay. Binding to a surface can be accomplished in any vessel suitable for containing the reactants. Examples of Such vessels include microtitre plates, test tubes, and micro-centrifuge tubes. In one embodiment, a fusion protein can be provided in which a domain that allows one or both of the proteins to be bound to a matrix is added to one or more of the molecules. For example, glutathione-S-transferase fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or RNA-binding protein, and the mixture incubated under conditions conducive to complex formation (e.g., at physiological conditions for salt and pH). Following incubation, the beads or microtitre plate wells are washed to remove any unbound components, the matrix is immobilized in the case of beads, and complex formation is determined either directly or indirectly, for example, as described above. Alternatively, the complexes can be dissociated from the matrix, and the level of binding or activity determined using standard techniques.

Other techniques for immobilizing proteins on matrices can also be used in the screening assays of the invention. For example, proteins may be immobilized utilizing conjugation of biotin and streptavidin. Biotinylated protein or target molecules can be prepared from biotin-NHS(N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies which are reactive with protein or target molecules but which do not interfere with binding of the protein to its target molecule can be derivatized to the wells of the plate, and unbound target or SLIM protein is trapped in the wells by antibody conjugation. Methods for detecting such complexes, in addition to those described above for the GST-immobilized complexes, include immunodetection of complexes using antibodies reactive with an RNA-binding protein.

Test Compounds

A variety of test compounds can be evaluated using the screening assays described herein. The term "test compound" includes any reagent or test agent which is employed in the assays of the invention and assayed. More than one compound, e.g., a plurality of compounds, can be tested at the same time in a screening assay. The term "screening assay" preferably refers to assays which test the ability of a plurality of compounds to influence the readout of choice rather than to tests which test the ability of one compound to influence a readout. Preferably, the subject assays identify compounds not previously known to have the effect that is being screened for. In one embodiment, high throughput screening may be used to assay for the activity of a compound.

In certain embodiments, the compounds to be tested can be derived from libraries (i.e., are members of a library of compounds). While the use of libraries of peptides is well established in the art, new techniques have been developed which have allowed the production of mixtures of other compounds, Such as benzodiazepines (Bunin, et al. (1992). J. Am. Chem. Soc. 114:10987; DeWitt et al. (1993). Proc. Natl. Acad. Sci., USA 90:6909) peptoids (Zuckerman. (1994). J. Med. Chem. 37:2678) oligocarbamates (Cho, et al. (1993). Science. 261:11303), and hydantoins (DeWitt, et al. supra). An approach for the synthesis of molecular libraries of small organic molecules with a diversity of 104-105 as been described (Carell, et al. (1994). Angew. Chem. Int. Ed. Engl. 33:2059; Carell, et al. (1994) Angew. Chem. Int. Ed. Engl. 33:2061).

The compounds of the present invention can be obtained using any of the numerous approaches in combinatorial library methods known in the art, including: biological libraries; spatially addressable parallel solid phase or solution phase libraries, synthetic library methods requiring deconvolution, the 'one-bead one-compound' library method, and synthetic library methods using affinity chromatography selection. The biological library approach is limited to peptide libraries, while the other four approaches are applicable to peptide, non-peptide oligomer or small molecule libraries of compounds (Lam, K. S. (1997) Anticancer Drug Des. 12:145). Other exemplary methods for the synthesis of molecular libraries can be found in the art, for example in: Erb, et al. (1994). Proc. Natl. Acad. Sci., USA 91:11422-; Horwell, et al. (1996) Immunopharmacology 33:68-; and in Gallop, et al. (1994); J. Med. Chem. 37:1233.

Exemplary compounds which can be screened for activity include, but are not limited to, peptides, nucleic acids, carbohydrates, small organic molecules, and natural product extract libraries.

Candidate/test compounds include, for example, 1) peptides such as soluble peptides, including Ig-tailed fusion peptides and members of random peptide libraries (see, e.g., Lam, K. S., et al. (1991) Nature 354:82-84; Houghten, R., et al. (1991) Nature 354:84-86) and combinatorial chemistry-derived molecular libraries made of D- and/or L-configuration amino acids; 2) phosphopeptides (e.g., members of random and partially degenerate, directed phosphopeptide libraries, see, e.g., Songyang, Z., et al. (1993) Cell 72:767-778); 3) antibodies (e.g., antibodies (e.g., intracellular, polyclonal, monoclonal, humanized, anti-idiotypic, chimeric, and single chain antibodies as well as Fab, F(ab')2, Fab expression library fragments, and epitope-binding fragments of antibodies); 4) small organic and inorganic molecules (e.g., molecules obtained from combinatorial and natural product libraries); 5) enzymes (e.g., endoribonucleases, hydrolases, nucleases, proteases, synthatases, isomerases, polymerases, kinases, phosphatases, oxido-reductases and ATPases), and 6) mutant forms of molecules.

The test compounds of the present invention can be obtained using any of the numerous approaches in combinatorial library methods known in the art, including: biological libraries; spatially addressable parallel solid phase or Solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) Anticancer Drug Des. 12:145).

Examples of methods for the synthesis of molecular libraries can be found in the art, for example in: DeWitt, et al. (1993) Proc. Natl. Acad. Sci., U.S.A. 90:6909; Erb, et al. (1994) Proc. Natl. Acad. Sci., USA 91:11422; Zuckermann, et al. (1994) J. Med. Chem. 37:2678; Cho, et al. (1993) Science 261:1303; Carrell, et al. (1994) Angew. Chem. Int. Ed. Engl. 33:2059; Carell, et al. (1994) Angew. Chem. Int. Ed. Engl. 33:2061; and Gallop, et al. (1994) J. Med. Chem. 37:1233.

Libraries of compounds can be presented in solution (e.g., Houghten (1992) Biotechniques 13:412-421), or on beads (Lam (1991) Nature 354:82-84), chips (Fodor (1993) Nature 364:555-556), bacteria (Ladner U.S. Pat. No. 5,223,409), spores (Ladner U.S. Pat. No. '409), plasmids (Cull, et al. (1992) Proc. Natl. Acad. Sci., USA 89:1865-1869) or phage (Scott and Smith (1990) Science 249:386-390; Devlin (1990) Science 249:404-406; Cwirla, et al. (1990) Proc. Natl. Acad. Sci., USA 87:6378-6382; Felici (1991) J. Mol. Biol. 222:301-310; Ladner supra.).

Compounds identified in the subject screening assays may be used, e.g., in methods of modulating embryogenesis, a parasitic associated state. It will be understood that it may be desirable to formulate such compound(s) as pharmaceutical compositions (described supra) prior to contacting them with cells.

Once a test compound is identified that directly or indirectly modulates, e.g., inhibits, an RNA-binding protein activity by one of the variety of methods described herein, the selected test compound (or "compound of interest") can then be further evaluated for its effect on cells, for example by contacting the compound of interest with cells either in vivo (e.g., by administering the compound of interest to a subject) or ex vivo (e.g., by isolating cells from the subject and contacting the isolated cells with the compound of interest or, alternatively, by contacting the compound of interest with a cell line) and determining the effect of the compound of interest on the cells, as compared to an appropriate control (such as untreated cells or cells treated with a control compound, or carrier, that does not modulate the biological response).

The instant invention also pertains to compounds identified in the subject screening assays.

III. Pharmaceutical Compositions

The invention also pertains to pharmaceutical compositions comprising a therapeutically effective amount of an RNA binding modulatory compound, e.g., a compound of formula I, Ia, Ib, II, IIa, IIb, IIc, III, IV, V, VI, VIa, VIb, VII, VIIa, VIIb, VIIc, VIId, VIIe, VIIf or a compound of Table 1 or 2, and a pharmaceutically acceptable carrier. Each of these compounds may be used alone or in combination as a part of a pharmaceutical composition of the invention.

In one embodiment, the RNA binding modulatory compound, e.g., compound of formula I, Ia, Ib, II, IIa, IIb, IIc, III, IV, V, VI, VIa, VIb, VII, VIIa, VIIb, VIIc, VIId, VIIe, VIIf or a compound of Table 1 or 2, is administered in combination with an additional agent, e.g., an anti-helminthic agent. The language "in combination with" an additional agent, e.g., an antihelminthic agent, includes co-administration of the compound with an additional agent, e.g., an antihelminthic agent, administration of the compound first, followed by administration of an additional agent, e.g., an antihelminthic agent, and administration of an additional agent, e.g., antihelminthic agent first, followed by administration of the compound. The compound can be administered substantially at the same time as the additional agent, e.g., antihelminthic agent, or at substantially different times as the additional agent, e.g., antihelminthic agent. Optimal administration rates for a given protocol of administration of the compound and/or the additional agent, e.g., antihelminthic agent, can be readily ascertained by those skilled in the art using conventional dosage determination tests conducted with regard to the specific compounds being utilized, the particular compositions formulated, the mode of application, the particular site of administration and the like.

The phrases "anti-helmintic agent" and "anti-helminthic agent," used interchangeably herein, include compounds that expel parasitic worms from the body of a subject. In one embodiment, the anti-helmintic agent is a vermifuge agent (e.g., a compound that stuns the parasitic worm prior to or substantially at the same time as the expelling). In another embodiment, the anti-helmintic agent is a vermicide (e.g., a compound that kills the parasitic worm prior to or substantially at the same time as the expelling). Examples of anti-helmintic agents include, but are not limited to, abamectin (e.g., Affirm®, Agri-Mek®, Avermectin®, Avid®, Vertimec® or Zephyr®), praziquantel (e.g., Biltricide®), albendazole (e.g., Albenza®, Eskazole® or Zentel®), diethylcarbamazine (e.g., Hetrazan®, Carbilazine®, Caricide®, Cypip®, Ethodryl®, Notezine®, Spatonin®, Filaribits® or Banocide Forte®), mebendazole (e.g., Ovex®, Vermox® or Antiox®), niclosamide (e.g., Niclocide®), ivermectin (e.g., Stromectol®, Mectizan® or Ivexterm®), suramin (e.g., Germanin®), thiabendazole (e.g., Mintezol®, Tresaderm® or Arbotect®), pyrantel pamoate, levamisole (e.g., Ergamisol®), triclabendazole, (e.g., Fasonex®) flubendazole (e.g., Flutelmium®, Flubenol®, Biovermin® or Flumoxal®), fenbendazole (e.g., Panacur®, Safe-Guard® or Panacur Rabbit®), octadepsipeptide (e.g., emodepside), piperazine derivatives, amino acetonitrile derivatives (e.g., monepantel, Zolvix®), oxamniquine (e.g., Vansil® or Mansil®), metrifonate (e.g., trichlorfon), bithionol, niridazole (e.g., Ambilgar®), stibophen, ciclobendazole, oxantel, pyrvinium, bephenium, desapidin and dichlorophen. One of skill in the art using conventional medical diagnoses would be able to determine the appropriate anti-helmintic agent to administer in combination with the RNA binding modulatory compound, e.g., the compounds of a compound of formula I, Ia, Ib, II, IIa, IIb, IIc, III, IV, V, VI, VIa, VIb, VII, VIIa, VIIb, VIIc, VIId, VIIe, VIIf or a compound of Table 1 or 2.

The RNA binding modulatory compounds, e.g., compounds of formula I, Ia, Ib, II, IIa, IIb, IIc, III, IV, V, VI, VIa, VIb, VII, VIIa, VIIb, VIIc, VIId, VIIe, VIIf or a compound of Table 1 or 2, that are basic in nature are capable of forming a wide variety of pharmaceutically acceptable salts with various inorganic and organic acids. The acids that may be used to prepare pharmaceutically acceptable acid addition salts of the compounds disclosed herein that are basic in nature are those that form non-toxic acid addition salts, i.e., salts containing pharmaceutically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and palmoate (i.e., 1,1'-methylene-bis-(2-hydroxy-3-naphthoate)] salts. Although such salts must be pharmaceutically acceptable for administration to a subject, e.g., a mammal, it is often desirable in practice to initially isolate the compound from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The preparation of other compounds not specifically described in the experimental section can be accomplished using combinations of the described reactions that will be apparent to those skilled in the art.

The RNA binding modulatory compounds, e.g., compounds of formula I, Ia, Ib, II, IIa, IIb, IIc, III, IV, V, VI, VIa, VIb, VII, VIIa, VIIb, VIIc, VIId, VIIe, VIIf or a compound of Table 1 or 2, that are acidic in nature are capable of forming a wide variety of pharmaceutically acceptable base salts. The chemical bases that may be used as reagents to prepare pharmaceutically acceptable base salts of those compounds that are acidic in nature are those that form non-toxic base salts with such compounds. Such non-toxic base salts include, but are not limited to those derived from such pharmaceutically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolamnionium and other base salts of pharmaceutically acceptable organic amines. The pharmaceutically acceptable base addition salts of the compounds that are acidic in nature may be formed with pharmaceutically acceptable cations by conventional methods. Thus, these salts may be readily prepared by treating the compounds disclosed herein with an aqueous solution of the desired pharmaceutically acceptable cation and evaporating the resulting solution to dryness, preferably under reduced pressure. Alternatively, a lower alkyl alcohol solution of the compounds of the invention may be mixed with an alkoxide of the desired metal and the solution subsequently evaporated to dryness.

The term "pharmaceutically acceptable carrier" includes any carrier that is suitable for administration to a mammal.

These compositions may also contain adjuvants such as preservatives, wetting agents, emulsifying agents and dispersing agents. Prevention of the action of microbes may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin. In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Pharmaceutical compositions of the present invention may be administered to a subject, e.g., a non-human animal or a human, orally, parenterally, topically, rectally, nasally, intravaginally or intracisternally. They are, of course, given by forms suitable for each administration route. For example, they are administered in tablets or capsule form, by injection, inhalation, eye lotion, ointment, etc., administration by injection, infusion or inhalation; topical by lotion or ointment; and rectal or vaginal suppositories.

The phrases "parenteral administration" and "administered parenterally" as used herein include modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally," as used herein, includes the administration of the RNA binding modulatory compound, e.g., compound of formula I, Ia, Ib, II, IIa, IIb, IIc, III, IV, V, VI, VIa, VIb, VII, VIIa, VIIb, VIIe, VIId, VIIe, VIIf or a compound of Table 1 or 2, other than directly into the central nervous system, such that it enters the subject's system and, thus, is subject to metabolism and other like processes, for example, subcutaneous administration.

In some methods, the compositions of the invention can be topically administered to any epithelial surface. An "epithelial surface" includes an area of tissue that covers external surfaces of a body, or which lines hollow structures including, but not limited to, cutaneous and mucosal surfaces. Such epithelial surfaces include oral, pharyngeal, esophageal, pulmonary, ocular, aural, nasal, buccal, lingual, vaginal, cervical, genitourinary, alimentary, and anorectal surfaces.

Compositions can be formulated in a variety of conventional forms employed for topical administration. These include, for example, semi-solid and liquid dosage forms, such as liquid solutions or suspensions, suppositories, douches, enemas, gels, creams, emulsions, lotions, slurries, powders, sprays, lipsticks, foams, pastes, toothpastes, ointments, salves, balms, douches, drops, troches, chewing gums, lozenges, mouthwashes, rinses.

Conventionally used carriers for topical applications include pectin, gelatin and derivatives thereof, polylactic acid or polyglycolic acid polymers or copolymers thereof, cellulose derivatives such as methyl cellulose, carboxymethyl cellulose, or oxidized cellulose, guar gum, acacia gum, karaya gum, tragacanth gum, bentonite, agar, carbomer, bladderwrack, ceratonia, dextran and derivatives thereof, ghatti gum, hectorite, ispaghula husk, polyvinypyrrolidone, silica and derivatives thereof, xanthan gum, kaolin, talc, starch and derivatives thereof, paraffin, water, vegetable and animal oils, polyethylene, polyethylene oxide, polyethylene glycol, polypropylene glycol, glycerol, ethanol, propanol, propylene glycol (glycols, alcohols), fixed oils, sodium, potassium, aluminum, magnesium or calcium salts (such as chloride, carbonate, bicarbonate, citrate, gluconate, lactate, acetate, gluceptate or tartrate).

Standard composition strategies for topical agents can be applied to the RNA binding modulatory compounds of the invention or a pharmaceutically acceptable salt thereof in order to enhance the persistence and residence time of the drug, and to improve the prophylactic efficacy achieved.

For topical application to be used in the lower intestinal tract or vaginally, a rectal suppository, a suitable enema, a gel, an ointment, a solution, a suspension or an insert can be used. Topical transdermal patches may also be used. Transdermal patches have the added advantage of providing controlled delivery of the compositions of the invention to the body. Such dosage forms can be made by dissolving or dispersing the agent in the proper medium.

Compositions of the invention can be administered in the form of suppositories for rectal or vaginal administration. These can be prepared by mixing the agent with a suitable non-irritating carrier which is solid at room temperature but liquid at rectal temperature and therefore will melt in the rectum or vagina to release the drug. Such materials include cocoa butter, beeswax, polyethylene glycols, a suppository wax or a salicylate that is solid at room temperature, but liquid at body temperature and, therefore, will melt in the rectum or vaginal cavity and release the active agent. Compositions which are suitable for vaginal administration also include pessaries, tampons, creams, gels, pastes, foams, films, or spray compositions containing such carriers as are known in the art to be appropriate. The carrier employed in the pharmaceutical compositions of the invention should be compatible with vaginal administration.

For ophthalmic applications, the pharmaceutical compositions can be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the compositions can be formulated in an ointment such as petrolatum. Exemplary ophthalmic compositions include eye ointments, powders, solutions and the like.

Powders and sprays can contain, in addition to the compound of the invention, carriers such as lactose, talc, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Ordinarily, an aqueous aerosol is made by formulating an aqueous solution or suspension of an RNA binding modulatory compound, e.g., compound of formula I, Ia, Ib, II, IIa, IIb, IIc, III, IV, V, VI, VIa, VIb, VII, VIIa, VIIb, VIIc, VIId, VIIe, VIIf or a compound of Table 1 or 2, together with conventional pharmaceutically acceptable carriers and stabilizers. The carriers and stabilizers vary with the requirements of the particular compound, but typically include nonionic surfactants (e.g., Tweens, Pluronics, polyethylene glycol and the like), proteins like serum albumin, sorbitan esters, oleic acid, lecithin, amino acids such as glycine, buffers, salts, sugars or sugar alcohols. Aerosols generally are prepared from isotonic solutions. Generation of the aerosol or any other means of delivery of the present invention may be accomplished by any of the methods known in the art. For example, in the case of aerosol delivery, the compound is supplied in a finely divided form along with any suitable carrier with a propellant.

Liquefied propellants are typically gases at ambient conditions and are condensed under pressure. The propellant may be any acceptable and known in the art including propane and butane, or other lower alkanes, such as those of up to 5 carbons. The composition is held within a container with an appropriate propellant and valve, and maintained at elevated pressure until released by action of the valve.

Compositions of the invention can also be orally administered in any orally-acceptable dosage form including, but not limited to, capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of sucrose octasulfate and/or antibiotic or contraceptive agent(s) as an active ingredient. A compound described herein may also be administered as a bolus, electuary or paste. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added. Tablets, and other solid dosage forms, such as dragees, capsules, pills and granules, may be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the RNA binding modulatory compound, e.g., compound of formula I, Ia, Ib, II, IIa, IIb, IIc, III, IV, V, VI, VIa, VIb, VII, VIIa, VIIb, VIIc, VIId, VIIe, VIIf or a compound of Table 1 or 2, only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients. Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to compounds of the invention, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Sterile injectable forms of the compositions of this invention can be aqueous or oleaginous suspension. These suspensions may be formulated according to techniques known in the art using suitable dispersing or wetting agents and suspending agents.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions. The sterile injectable preparation may also be a sterile injectable solution or suspension in a nontoxic parenterally-acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxethylated versions. These oil solutions or suspensions may also contain a long-chain alcohol diluent or dispersant. The RNA binding modulatory compound, e.g., compound of formula I, Ia, Ib, II, IIa, IIb, IIc, III, IV, V, VI, VIa, VIb, VII, VIIa, VIIb, VIIc, VIId, VIIe, VIIf or a compound of Table 1 or 2, or a pharmaceutically acceptable salt thereof will represent some percentage of the total dose in other dosage forms in a material forming a combination product, including liquid solutions or suspensions, suppositories, douches, enemas, gels, creams, emulsions, lotions slurries, soaps, shampoos, detergents, powders, sprays, lipsticks, foams, pastes, toothpastes, ointments, salves, balms, douches, drops, troches, lozenges, mouthwashes, rinses and others.

In one embodiment, the compounds of the invention may be administered prophylactically. For prophylactic applications, the pharmaceutical composition of the invention can be applied prior to potential infection. The timing of application prior to potential infection can be optimized to maximize the prophylactic effectiveness of the compound. The timing of application will vary depending on the mode of administration, doses, the stability and effectiveness of composition, the frequency of the dosage, e.g., single application or multiple dosage. One skilled in the art will be able to determine the most appropriate time interval required to maximize prophylactic effectiveness of the compound.

An RNA binding modulatory compound, e.g., compound of formula I, Ia, Ib, II, IIa, IIb, IIc, III, IV, V, VI, VIa, VIb, VII, VIIa, VIIb, VIIc, VIId, VIIe, VIIf or a compound of Table 1 or 2, when present in a composition will generally be present in an amount from about 0.000001% to about 100%, more preferably from about 0.001% to about 50%, and most preferably from about 0.01% to about 25% of total weight.

For compositions of the present invention comprising a carrier, the composition comprises, for example, from about 1% to about 99%, preferably from about 50% to about 99%, and most preferably from about 75% to about 99% by weight of at least one carrier.

Also, the separate components of the compositions of the invention may be preblended or each component may be added separately to the same environment according to a predetermined dosage for the purpose of achieving the desired concentration level of the treatment components and so long as the components eventually come into intimate admixture with each other. Further, the present invention may be administered or delivered on a continuous or intermittent basis.

The RNA binding modulatory compounds, e.g., compounds of formula I, Ia, Ib, II, IIa, IIb, IIc, III, IV, V, VI, VIa, VIb, VII, VIIa, VIIb, VIIc, VIId, VIIe, VIIf or a compound of Table 1 or 2, may be used in the veterinary sector in any technique routine to one of skill in the art, including, for example, oral administration, parenterally (e.g., intraruminal, intramuscular, intravenous or subcutaneous injection) or by transdermal methods. The RNA binding modulatory compounds, e.g., compounds of formula I, Ia, Ib, II, IIa, IIb, IIc, III, IV, V, VI, VIa, VIb, VII, VIIa, VIIb, VIIc, VIId, VIIe, VIIf or a compound of Table 1 or 2 may also be dispersed or dissolved in a pharmaceutically acceptable carrier for injection or transdermal application. Alternatively, the RNA binding modulatory compounds, e.g., compounds of formula I, Ia, Ib, II, IIa, IIb, IIc, III, IV, V, VI, VIa, VIb, VII, VIIa, VIIb, VIIc, VIId, VIIe, VIIf or a compound of Table 1 or 2, may be formulated into an implant for subcutaneous administration.

For oral administration to warm-blooded animals, the RNA binding modulatory compounds, e.g., compounds of formula I, Ia, Ib, II, IIa, IIb, IIc, III, IV, V, VI, VIa, VIb, VII, VIIa, VIIb, VIIc, VIId, VIIe, VIIf or a compound of Table 1 or 2, may be formulated as animal feeds, animal feed premixes, animal feed concentrates, pills, pastes, suspensions, solutions, gels, tablets, boluses and capsules. In addition, the an RNA binding modulatory compounds, e.g., compounds of formula I, Ia, Ib, II, IIa, IIb, IIc, III, IV, V, VI, VIa, VIb, VII, VIIa, VIIb, VIIc, VIId, VIIe, VIIf or a compound of Table 1 or 2, may be administered to the animals in their drinking water.

For oral administration, the dosage form chosen should provide the animal with about 0.01 mg/kg to 100 mg/kg of animal body weight per day of the RNA binding modulatory compound, e.g., compounds of formula I, Ia, Ib, II, IIa, IIb, IIc, III, IV, V, VI, VIa, VIb, VII, VIIa, VIIb, VIIc, VIId, VIIe, VIIf or a compound of Table 1 or 2. For parenteral administration, the dosage form chosen should provide the animal with about 0.01 mg/kg to 100 mg/kg of animal body weight per day of the RNA binding modulatory compound, e.g., compound of formula I, Ia, Ib, II, IIa, IIb, IIc, III, IV, V, VI, VIa, VIb, VII, VIIa, VIIb, VIIc, VIId, VIIe, VIIf or a compound of Table 1 or 2.

The RNA binding modulatory compounds, e.g., compounds of formula, Ia, Ib, II, IIa, IIb, IIc, III, IV, V, VI, VIa, VIb, VII, VIIa, VIIb, VIIc, VIId, VIIe, VIIf or a compound of Table 1 or 2, may also be applied topically to the animals in the form of dips, dusts, collars, medallions, sprays and pour-on formulations. For topical application, dips and sprays usually contain about 0.5 ppm to 5,000 ppm or about 1 ppm to 3,000 ppm of the RNA binding modulatory compound, e.g., compound of formula I, Ia, Ib, II, IIa, IIb, IIc, III, IV, V, VI, VIa, VIb, VII, VIIa, VIIb, VIIc, VIId, VIIe, VIIf or a compound of Table 1 or 2. In addition, the RNA binding modulatory compounds, e.g., compounds of formula I, Ia, Ib, II, IIa, IIb, IIc, III, IV, V, VI, VIa, VIb, VII, VIIa, VIIb, VIIc, VIId, VIIe, VIIf or a compound of Table 1 or 2, may be formulated as ear tags for animals, particularly quadrupeds such as cattle and sheep.

Pesticidal Compositions

The invention also pertains to pesticidal compositions comprising a pesticidally effective amount of an RNA binding modulatory compound, e.g., compound of formula I, Ia, Ib, II, IIa, IIb, IIc, III, IV, V, VI, VIa, VIb, VII, VIIa, VIIb, VIIc, VIId, VIIe, VIIf or a compound of Table 1 or 2, and an agronomically acceptable carrier. Each of these compounds may be used alone or in combination as a part of a pesticidal composition of the invention.

In one embodiment, the RNA binding modulatory compound, e.g., compound of formula I, Ia, Ib, II, IIa, IIb, IIc, III, IV, V, VI, VIa, VIb, VII, VIIa, VIIb, VIIc, VIId, VIIe, VIIf or a compound of Table 1 or 2, is administered in combination with an agricultural agent. The language "in combination with" an agricultural agent includes co-administration of the compound and with an agricultural agent, administration of the compound first, followed by administration of an agricultural agent, and administration of an agricultural agent first, followed by administration of the compound. The compound can be administered substantially at the same time as the agricultural agent or at substantially different times as the agricultural agent. Optimal administration rates for a given protocol of administration of the compound and/or the agricultural agent can be readily ascertained by those skilled in the art using conventional determination tests conducted with regard to the specific compounds being utilized, the particular compositions formulated, the mode of application, the particular site of administration and the like.

The term "agricultural agent" includes, for example, insecticides, attractants, sterilizing agents, bactericides, acaricides, nematicides, fungicides, growth-regulating substances, fertilizers or herbicides, such as aldimorph, ampropylfos, ampropylfos-potassium, andoprim, anilazine, azaconazole, azoxystrobin, benalaxyl, benodanil, benomyl, benzamacril, benzamacryl-isobutyl, bialaphos, binapacryl, biphenyl, bitertanol, blasticidin-S, bromuconazole, bupirimate, buthiobate, calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur, quinconazole, quintozene (PCNB), sulphur and sulphur preparations, tebuconazole, tecloftalam, tecnazene, tetcyclasis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, triichlamide, tricyclazole, tridemorph, triflumizole, triforine, triticonazole, uniconazole, validamycin A, vinclozolin, viniconazole, zarilamide, zineb, ziram, Dagger G, OK-8705, OK-8801, α.-(1,1-dimethylethyl)-β-(2-phenoxyethyl)-1H-1,2,4-triazole-1-ethanol, α-(2,4-dichlorophenyl)-β-fluoro-β-propyl-1H-1,2,4-triazole-1-ethanol, α-(2,4-dichlorophenyl)-β-methoxy-α-methyl-1H-1,2,4-triazole-1-ethanol, α-(5-methyl-1,3-dioxan-5-yl)-β-[[4-(trifluoromethyl)-phenyl]-methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-α-(methoxyimino)-N-methyl-2-phenoxy-phenylacetamide, 1-isopropyl{2-methyl-1-[[[1-(4-methylphenyl)-ethyl]-amino]-carbonyl]-propyl}-carbamate, 1-(2,4-dichlorophenyl)-2-(1H-1,2,4-triazol-1-yl)-ethanone-O-(phenylmethyl)-oxime, 1-(2-methyl-1-naphthalenyl)-1H-pyrrol-2,5-dione, 1-(3,5-dichlorophenyl)-3-(2-propenyl)-2,5-pyrrolidindione, 1-[(diiodomethyl)-sulphonyl]4-methyl-benzene, 1-[[2-(2,4-dichlorophenyl)-1,3-dioxolan-2-yl]-methyl]-1H-imidazole, 1-[1-[2-(4-chlorophenyl)-3-phenyloxiranyl]-methyl]-1H-1,2,4-triazole, 1-[1-[2-[(2,4-dichlorophenyl)-methoxy]-phenyl]-ethenyl]-1H-imidazole, 1-methyl-5-nonyl-2-(phenylmethyl)-3-pyrrolidinole. 2',6'-dibromo-2-methyl-4'-trifluoromethoxy-4'-trifluoro-methyl-1,3-thiazole-5-carboxanilide, 2,2-dichloro-N-[1-(4-chlorophenyl)-ethyl]-1-ethyl-3-methyl-cyclopropanecarboxamide, 2,6-dichloro-5-(methylthio)-4-pyrimidinyl-thiocyanate, 2,6-dichloro-N-(4-trifluoromethylbenzyl)-benzamide, 2,6-dichloro-N-[[4-(trifluoromethyl)-phenyl]-methyl]-benzamide, 2-(2,3,3-triiodo-2-propenyl)-2H-tetrazole, 2-[(1-methylethyl)-sulphonyl]-5-(trichloromethyl)-1,3,4-thiadiazole, 2-[[6-deoxy-4-O-(4-O-methyl-β-D-glycopyranosyl)-α-D-glucopyranosyl]-amino]-4-methoxy-1H-pyrrolo[2,3-d]pyrimidine-5-carbonitrile, 2-aminobutane, 2-bromo-2-(bromomethyl)-pentanedinitrile, 2-chloro-N-(2,3-dihydro-1,1,3-trimethyl-1H-inden-4-yl)-3-pyridinecarboxamide, 2-chloro-N-(2,6-dimethylphenyl)-N-(isothiocyanatomethyl)-acetamide, 2-phenylphenol (OPP), 3,4-dichloro-1-[4-(difluoromethoxy)-phenyl]-1H-pyrrol-2,5-dione, 3,5-dichloro-N-[cyano[(1-methyl-2-propynyl)-oxy]-methyl]-benzamide, 3-(1,1-dimethylpropyl-1-oxo-1H-indene-2-carbonitrile, 3-[2-(4-chlorophenyl)-5-ethoxy-3-isoxazolidinyl]-pyridine, 4-chloro-2-cyano-N,N-dimethyl-5-(4-methylphenyl)-1H-imidazole-1-sulphonamide, 4-methyl-tetrazolo[1,5-a]quinazolin-5(4H)-one, 8-(1,1-dimethylethyl)-N-ethyl-N-propyl-1,4-dioxaspiro[4,5]decane-2-methanamine, 8-hydroxyquinoline sulphate, 9H-xanthene-2-[(phenylamino)-carbonyl]-9-carboxylic hydrazide, bis-(1-methylethyl)-3-methyl-4-[(3-methylbenzoyl)-oxy]-2,5-thiophenedicarboxylate, cis-1-(4-chlorophenyl)-2-(1H-1,2,4-triazol-1-yl)-cycloheptanol, cis-4-[3-[4-(1,1-dimethylpropyl)-phenyl-2-methylpropyl]-2,6-dimethyl-morpholine hydrochloride, ethyl[(4-chlorophenyl)-azo]-cyanoacetate, potassium bicarbonate, methanetetrathiol-sodium salt, methyl 1-(2,3-dihydro-2,2-dimethyl-1H-inden-1-yl)-1H-imidazole-5-carboxylate, methyl N-(2,6-dimethylphenyl)-N-(5-isoxazolylcarbonyl)-DL-alaninate, methyl N-(chloroacetyl)-N-(2,6-dimethylphenyl)-DL-alaninate, N-(2,3-dichloro-4-hydroxyphenyl)-1-methylcyclohexanecarboxamide, N-(2,6-dimethylphenyl)-2-methoxy-N-(tetrahydro-2-oxo-3-furanyl)-acetamide, N-(2,6-dimethylphenyl)-2-methoxy-N-(tetrahydro-2-oxo-3-thienyl)-acetamide, N-(2-chloro-4-nitrophenyl)-4-methyl-3-nitro-benzenesulphonamide, N-(4-cyclohexylphenyl)-1,4,5,6-tetrahydro-2-pyrimidinamine, N-(4-hexylphenyl)-1,4,5,6-tetrahydro-2-pyrimidinamine, N-(5-chloro-2-methylphenyl)-2-methoxy-N-(2-oxo-3-oxazolidinyl)-acetamide, N-(6-methoxy)-3-pyridinyl)-cyclopropanecarboxamide, N-[2,2,2-trichloro-1-[(chloroacetyl)-amino]-ethyl]-benzamide, N-[3-chloro-4,5-bis(2-propinyloxy)-phenyl]-N'-methoxy-methanimidamide, N-formyl-N-hydroxy-DL-alanine-sodium salt, O,O-diethyl [2-(dipropylamino)-2-oxoethyl]-ethylphosphoramidothioate, 0-methyl S-phenyl phenylpropylphosphoramidothioate, S-methyl 1,2,3-benzothiadiazole-7-carbothioate, spiro[2H]-1-benzopyrane-2,1'(3'H)-isobenzofuran]-3'-one, bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations, abamectin, acephate, acetamiprid, acrinathrin, alanycarb, aldicarb, aldoxycarb, alpha-cypermethrin, alphamethrin, amitraz, avermectin, AZ 60541, azadirachtin, azamethiphos, azinphos A, azinphos M, azocyclotin, *Bacillus popilliae, Bacillus sphaericus, Bacillus subtilis, Bacillus thuringiensis, baculoviruses, Beauveria bassiana, Beauveria tenella*, bendiocarb, benfuracarb, bensultap, benzoximate, betacyfluthrin, bifenazate, bifenthrin, bioethanomethrin, biopermethrin, BPMC, bromophos A, bufencarb, buprofezin, butathiofos, butocarboxim, butylpyridaben, cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, cis-resmethrin, cispermethrin, clocythrin, cloethocarb, clofentezine, cyanophos, cycloprene, cycloprothrin, cyfluthrin, cyhalothrin, cyhexatin, cypermethrin, cyromazine, deltamethrin, demeton M, demeton S, demeton-S-methyl, diafenthiuron, diazinon, dichlorvos, diflubenzuron, dimethoate, dimethylvinphos, diofenolan, disulfoton, docusat-sodium, dofenapyn, eflusilanate, emamectin, empenthrin, endosulfan, *Entomopfthora* spp., esfenvalerate, ethiofencarb, ethion, ethoprophos, etofenprox, etoxazole, etrimfos, fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazinam, fluazuron, flubrocythrinate, flucycloxuron, flucythrinate, flufenoxuron, flutenzine, fluvalinate, fonophos, fosmethilan, fosthiazate, fubfenprox, furathiocarb, granulosis viruses, halofenozide, HCH, heptenophos, hexaflumuron, hexythiazox, hydroprene, imidacloprid, isazofos, isofenphos, isoxathion, ivermectin, nuclear polyhedrosis viruses, lambda-cyhalothrin, lufenuron, malathion, mecarbam, metaldehyde, methamidophos, *Metarhizium anisopliae, Metarhizium flavoviride*, methidathion, methiocarb, methomyl, methoxyfenozide, metolcarb, metoxadiazone, mevinphos, milbemectin, monocrotophos, naled, nitenpyram, nithiazine, novaluron, omethoate, oxamyl, oxydemethon M, *Paecilomyces fumosoroseus*, parathion A, parathion M, permethrin, phenthoate, phorate, phosalone, phosmet, phosphamidon, phoxim, pirimicarb, pirimiphos A, pirimiphos M, profenofos, promecarb, propoxur, prothiofos, prothoate, pymetrozine, pyraclofos, pyresmethrin, pyrethrum, pyridaben, pyridathion, pyrimidifen, pyriproxyfen, quinalphos, ribavirin, salithion, sebufos, silafluofen, spinosad, sulfotep, sulprofos, tau-fluvalinate, tebufenozide, tebufenpyrad, tebupirimiphos, teflubenzuron, tefluthrin, temephos, temivinphos, terbufos, tetrachlorvinphos, thetacypermethrin, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb, vamidothion, vaniliprole, *Verticillium lecanii*, YI 5302, zeta-cypermethrin, zolaprofos, (1R-cis)-[5-(phenylmethyl)-3-furanyl]-methyl-3-[(dihydro-2-oxo-3(2H)-furanylidene)-methyl]-2,2-dimethylcyclopropanecarboxylate, (3-phenoxyphenyl)-methyl-2,2,3,3-tetramethylcyclopropanecarboxylate, 1-[(2-chloro-5-thiazolyl)methyl]tetrahydro-3,5-dimethyl-N-nitro-1,3,5-triazine-2(1H)-imine, 2-(2-chloro-6-fluorophenyl)-4-[4-(1,1-dimethylethyl)phenyl]-4,5-dihydro-oxazole, 2-(acetyloxy)-3-dodecyl-1,4-naphthalenedione, 2-chloro-N-[[[4-(1-phenylethoxy)-phenyl]-amino]-carbonyl]-benzamide, 2-chloro-N-[[[4-(2,2-dichloro-1,1-difluoroethoxy)-phenyl]-amino]-carbonyl]-benzamide, 3-methylphenyl propylcarbamate, 4-[4-(4-ethoxyphenyl)-4-methylpentyl]-1-fluoro-2-phenoxy-benzene, 4-chloro-2-(1,1-dimethylethyl)-5-[[2-(2,6-dimethyl-4-phenoxyphenoxy)ethyl]thio]-3(2H)-pyridazinone, 4-chloro-2-(2-chloro-2-methylpropyl)-5-[(6-iodo-3-pyridinyl)methoxy]-3(2H)-pyridazinone, 4-chloro-5-[(6-chloro-3-pyridinyl)methoxy]-2-(3,4-dichlorophenyl)-3 (2H)-pyridazinone, *Bacillus thuringiensis* strain EG-2348, [2-benzoyl-1-(1,1-dimethylethyl)-hydrazinobenzoic acid, 2)-dimethyl-3-(2,4-dichlorophenyl)-2-oxo-1-oxaspiro[4,5] dec-3-en-4-ylbutanoate, [3-[(6-chloro-3-pyridinyl)methyl]-2-thiazolidinyldene]-cyanamide, dihydro-2-(nitromethylene)-2H-1,3-thiazine-3(4H)-carboxaldehyde, ethyl[2-[[1,6-dihydro-6-oxo-1-(phenylmethyl)-4-pyridazinyl]oxy]ethyl]-carbamate, N-(3,4,4-trifluoro-1-oxo-3-butenyl)-glycine, N-(4-chlorophenyl)-3-[4-(difluoromethoxy)phenyl]-4,5-dihydro-4-phenyl-1H-pyrazole-1-carboxamide, N-[(2-chloro-5-thiazolyl)methyl]-N'-methyl-N'-nitro-guanidine, N-methyl-N'-(1-methyl-2-propenyl)-1,2-hydrazinedicarbothioamide, N-methyl-N'-2-propenyl-1,2-hydrazinedicarbothioamide and O,O-diethyl[2-(dipropylamino)-2-oxoethyl]-ethylphosphoramidothioate.

Treatment of the plants and soil with the RNA binding modulatory compounds, e.g., compounds of formula I, Ia, Ib, II, IIa, IIb, IIc, III, IV, V, VI, VIa, VIb, VII, VIIa, VIIb, VIIc, VIId, VIIe, VIIf or a compound of Table 1 or 2, may be carried out directly or by allowing the compounds to act on the surroundings, environment or storage space by the customary treatment methods, for example by immersion, spraying, evaporation, fogging, scattering, painting on and, in the case of propagation material, in particular in the case of seeds, also by applying one or more coats.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions to be used, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products that exceed the effects which were actually to be expected may occur.

The RNA binding modulatory compounds, e.g., compounds of I, Ia, Ib, II, IIa, IIb, IIc, III, IV, V, VI, VIa, VIb, VII, VIIa, VIIb, VIIc, VIId, VIIe, VIIf or a compound of Table 1 or 2, may used in unchanged form or together with an agronomically acceptable carrier. The term "agronomically acceptable carrier" includes any carrier suitable for administration to a plant or soil, for example, customary excipients in formulation techniques, such as solutions (e.g., directly sprayable or dilutable solutions), emulsions, (e.g., emulsion concentrates and diluted emulsions), wettable powders, suspensions, soluble powders, powders, dusts, pastes, soluble powders, granules, suspension-emulsion concentrates, encapsulation into polymeric materials, coatable pastes, natural and synthetic materials impregnated with active compound and microencapsulations in polymeric substances. These formulations are produced in a known manner, for example by mixing the compounds with agronomically acceptable carrier, such as liquid solvents or solid carriers, optionally with the use of surfactants, including emulsifiers, dispersants, and/foam-formers.

If the agronomically acceptable carrier is water, it may also possible to employ, for example, organic solvents as auxiliary solvents. Suitable liquid solvents include, for example, aromatics (e.g., xylene, toluene and alkylnaphthalenes); chlorinated aromatics or chlorinated aliphatic hydrocarbons (e.g., chlorobenzenes, chloroethylenes and methylene chloride); aliphatic hydrocarbons (e.g., cyclohexane); paraffins (e.g., petroleum fractions, mineral and vegetable oils); alcohols (e.g., butanol or glycol and also their ethers and esters);

ketones (e.g., acetone, methyl ethyl ketone, methyl isobutyl ketone and cyclohexanone) and strongly polar solvents (e.g., dimethylformamide and dimethyl sulphoxide).

Suitable solid agronomically acceptable carriers include, for example, ammonium salts and ground natural minerals (e.g., kaolins, clays, talc, chalk, quartz, attapulgite, montmorillonite and diatomaceous earth); ground synthetic minerals (e.g., highly disperse silica, alumina and silicates); crushed and fractionated natural rocks (e.g., calcite, marble, pumice, sepiolite and dolomite); synthetic granules of inorganic and organic meals; granules of organic material (e.g., sawdust, coconut shells, maize cobs and tobacco stalks);

Suitable emulsifiers and foam-formers include, for example, nonionic and anionic emulsifiers (e.g., polyoxyethylene fatty acid esters, polyoxyethylene fatty alcohol ethers, for example, alkylaryl polyglycol ethers, alkylsulphonates, alkyl sulphates and arylsulphonates) protein hydrolysates.

Suitable dispersants include, for example, lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives may include, for example, mineral and vegetable oils.

Colorants such as inorganic pigments, for example, iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc may also be included in the agronomically acceptable carrier.

The pesticidal compositions may be administered to the plant or soil by any techniques known in the art, including, for example, spraying, atomizing, dusting, scattering, coating or pouring. One of skill in the art would be able to determine the appropriate technique for administration without undue experimentation according the specific pest to be combated, the specific chemical composition and formulation of the compound being employed, the method of applying the compound/formulation, and the locus of treatment.

In one embodiment, the pesticidal compositions comprising an RNA binding modulatory compound, e.g., compound of formula I, Ia, Ib, II, IIa, IIb, IIc, III, IV, V, VI, VIa, VIb, VII, VIIa, VIIb, VIIc, VIId, VIIe, VIIf or a compound of Table 1 or 2, may be administered by foliar application. In another embodiment, the pesticidal composition may also reach the plants through the root system via the soil (systemic action) by drenching the locus of the plant with a liquid preparation or by incorporating the substances into the soil in solid form, e.g., in the form of granules (soil application). In rice cultivations, these granules may be dispensed over the flooded paddy field. The pesticidal compositions of the invention may also be applied to tubers or seed grain, for example, by soaking, spraying or drenching the seed grain or tubers in a liquid pesticidal composition or by coating the tubers or seed grain with a solid pesticidal composition.

The pesticidal compositions disclosed herein generally comprise between 0.1 and 95% by weight of active compound, preferably between 0.5 and 90%. Favorable application rates are, in general, 1 g to 2 kg of active substance (AS) per hectare (ha), for example, 10 g to 1 kg AS/ha or 20 g to 600 g AS/ha. For application of tubers or seed grain, dosages of 10 mg to 1 g active substance per kg of seed grain or tubers may be used.

The contents of all references, patent applications and patents, cited throughout this application are hereby expressly incorporated by reference. Each reference disclosed herein is incorporated by reference herein in its entirety. Any patent application to which this application claims priority is also incorporated by reference herein in its entirety.

EXEMPLIFICATION OF THE INVENTION

Example 1

Identification of Modulators of RNA Binding Proteins MEX-5, POS-1 and MEX-3

Expression and Purification of Recombinant MEX-5, POS-1, and MEX-3

MEX-5: The expression and purification of recombinant MEX-5 protein has previously been described in Pagano, J. M., Farley, B. M., McCoig, L. M. and Ryder, S. P. (2007) "Molecular basis of RNA recognition by the embryonic polarity determinant MEX-5;" *J Biol Chem;* 282, 8883-8894. The fragment of mex-5 containing the TZF domain (amino acids 236-350) was amplified from a commercially available ORFeome clone (Open Biosystems) and sub-cloned into the vector pMal-c (NEB), which encodes maltose binding protein as an N-terminal fusion. This construct is termed pMal-MEX-5 (236-350).

MEX-5 is expressed in *Escherchia. coli* JM109 liquid cultures grown at 37° C. Cultures were induced during mid log phase by the addition of 0.1 mM isopropyl 1-thio-β-D-galactopyranoside (IPTG) and allowed to grow for three hours. An amount of 100 μM zinc acetate (final concentration) was added at the time of induction. The pelleted cells were resuspended in lysis buffer (50 mM Tris pH 8.8, 200 mM NaCl, 2 mM DTT, EDTA free protease inhibitor tablet (Roche), 100 μM Zn(OAc)$_2$) and lysed by sonication. The soluble protein was purified in three steps using standard chromatography methods: (1) amylose affinity (NEB), (2) Hi-TRAP-Q (GE Healthcare), and (3) Hi-TRAP-S (GE Healthcare). The Q buffer was composed of 50 mM Tris, pH 8.8, 20 mM-1500 mM NaCl, 2 mM DTT, and 100 μM Zn(OAc)$_2$. The S buffer was composed of 50 mM MOPS, pH 6.0, 20 mM-1500 mM NaCl, 2 mM DTT, 100 μM Zn(OAc)$_2$. The pure fractions, determined by coomassie-stained SDS-PAGE, were dialyzed into storage buffer (20 mM Tris, pH 8.0, 25 mM NaCl, 100 μM Zn(OAc)$_2$, 2 mM DTT). The protein concentration was determined by measuring absorbance at 280 nm and the calculated extinction coefficient. The protein was stored at 50 μM concentration at 4° C.

POS-1: The expression and purification of recombinant POS-1 protein has been previously described in Farley, B. M., Pagano, J. M. and Ryder, S. P. (2008) "RNA target specificity of the embryonic cell fate determinant POS-1." RNA, 14, 2685-2697. The sequence encoding amino acids 80-180 of POS-1 was amplified from the corresponding ORFeome (Open Biosystems) clone via PCR and cloned in frame into the multiple cloning site of pHMTc, a derivative of pMal-c2x (NEB) that includes an N-terminal 6-his tag and a TEV protease site after MBP.

The protein was expressed from this construct in *E. coli* strain BL21 (DE3) Gold (Stratagene). The protein expression was induced by addition of 1 mM IPTG and 100 μM Zn(OAc)$_2$ at mid-log phase. Cells were induced for three hours prior to harvesting and the cells were lysed and purified using an amylose column (NEB). The eluate was passed through a HiTrap SP column, and the collected flow through was purified over a HiTrap Q (GE Healthcare) column. The following buffers were used: Lysis buffer (50 mM Tris, pH 8.0, 200 mM NaCl, 2 mM DTT, 100 µM Zn(OAc)$_2$), S buffer (50 mM MOPS pH 6.0, 20 mM NaCl, 2 mM DTT, 100 µM Zn(OAc)$_2$), and Q buffer (50 mM Tris, pH 8.8, 20 mM-750 mM NaCl, 2 mM DTT, 100 µM Zn(OAc)$_2$). The purified POS-1 was dialyzed into storage buffer (25 mM Tris-Cl pH 8.0, 25 mM NaCl, 100 µM Zn(OAc)$_2$, 2 mM DTT), concentrated to approximately 100 µM using a 30,000 MWCO spin concentrator (vivascience Group), and stored at 4° C. for up to two months.

MEX-3: The sequence encoding amino acids 45-205 of MEX-3 was amplified from the ORFeome clone (Open Biosystems) and subcloned into pMal-c (NEB). MBP-MEX-3 (45-205) was expressed and purified from BL21 (DE3) Gold (Stratagene) E. coli. A liquid culture grown at 37° C. was induced at mid-log phase with 1 mM isopropyl 1-thio-β-D-galactopyranoside and grown for 3 hours before harvesting cells. The cells were lysed in lysis buffer and purified using amylose affinity resin (NEB), followed by a HiTrap Q and Source 15Q (GE Healthcare) columns at 4° C. using the lysis buffer and Q-buffer outlined for MEX-5, above. The purified MEX-3 was dialyzed into storage buffer (25 mM Tris, pH 8.0, 25 mM NaCl, 2 mM DTT) and stored at 4° C. at a concentration between 30-50 µM.

Fluorescein-Labeled RNA Oligonucleotides:

All RNA oligonucleotides were chemically synthesized by Dharmacon or Integrated DNA Technologies. Upon arrival, each RNA was deprotected and stored according to the manufacturer's instructions. Prior to use, the RNA was resuspended in 10 mM Tris-HCl, pH 8.0, 0.1 mM EDTA, and the concentration determined by UV spectrophotometry using the calculated extinction coefficient at 260 nm based on the specific sequence. The sequence of the MEX-5 binding RNA (TCR2) is UUUCUUUAUAACUUGUUACAAU-UUUUGAAA (SEQ ID NO:1). The POS-1 binding RNA (BMF018) is AACUAUUAUUAUUUGUUAUUCAUAU-UUU (SEQ ID NO:2). The MEX-3 binding RNA (SEQ14) is CGAGCAGGAAGUGUGCAGAGUUUAGGACGU (SEQ ID NO:3).

The RNA used for the small molecule screen was labeled at the 3'-end with fluorescein by Dharmacon during synthesis. In a few cases, follow up experiments were performed with post-synthetically labeled RNA. In this case, fluorescein 5-thiosemicarbazide (FTS C, Invitrogen) was used to 3'-end label each RNA after treatment with sodium periodate (see Reines, S. A. and Cantor, C. R. (1974) "New fluorescent hydrazide reagents for the oxidized 3'-terminus of RNA" Nucleic Acids Res. 1, 767-786). A representative 50 µl reaction consisted of 0.5 nanomoles RNA, 100 mM NaOAc, pH 5.1, and 5 nanomoles NaIO$_4$. After the reaction was complete (90 minutes at room temperature), the sample was ethanol precipitated by adding 1 µl RNase free glycogen (Invitrogen 20 µg/µl), ½0$^{th}$ volume of 5 M NaCl, and 2 volumes of 100% ice-cold ethanol. The resulting pellet was resuspended in 50 µl of 100 mM NaOAc, pH 5.1 containing 1 mM FTSC and was allowed to react overnight at 4° C. in the dark. The unreacted label was removed by ethanol precipitation with resuspension of the pellet in a small volume of TE, and purification over a Roche G-25 size exclusion spin column. The labeling efficiency is determined by calculating the ratio of fluorescein absorbance at 490 nm to RNA-fluorescein absorbance at 260 nm. Typical efficiencies are 60-80%.

Screening Protocol:

MEX-5: The ability of MEX-5 to associate with RNA was monitored by fluorescence polarization using a victor V3 or victor V2V plate reader (Perkin Elmer) in 384-well FluoTrak microplates (Grenier). Each plate contained 320 wells with 32 no protein control wells and 32 no compound control wells. The concentration of MEX-5 and fluorescein-labeled TCR2 RNA was chosen to maximize signal to noise while maintaining sub-saturation binding. The final concentration of reagents in each experimental well was 120 nM MBP-MEX-5, 2 nM TCR2 RNA, 192 µM test compound, 50 mM Tris-HCl, pH 8.0, 100 mM NaCl 0.01% IGEPAL CA-360, 0.01 mg/mL tRNA from S. cerevisiae (Sigma, 2000 Units) and 100 µM Zn(OAc)$_2$. The Z-value calculated for each plate from the no protein and no compound controls ranged between 0.8 and 0.9 (see Zhang, J. H., Chung, T. D. and Oldenburg, K. R. (1999) "A Simple Statistical Parameter for Use in Evaluation and Validation of High Throughput Screening Assays" J. Biomol. Screen 4, 67-73).

Each day, two stock solutions were prepared, a protein mix and an RNA mix. The protein mix contained 200 nM MBP-MEX-5 dissolved in 100 µM Zn(OAc)$_2$. The RNA mix contained 5 nM labeled TCR2 RNA, 125 mM Tris-HCl, pH 8.0, 250 mM NaCl, 0.025% IGEPAL CA-360 (Sigma), 0.025 mg/mL tRNA, and 100 µM Zn(OAc)$_2$. A 96-pin liquid handling robot was used to transfer 2 µL of 2 mM stock of test compound dissolved in DMSO into 320 wells of a microplate. The remaining 84 wells were filled with 2 µL of DMSO (no protein and no compound controls). Subsequently, a µFill plate dispenser was used to transfer 30 µL of protein stock into the plate 352 wells of the plate. The remaining 32 wells received 30 µL of 100 µM Zn(OAc)$_2$ (no protein controls). Finally, The µFill plate dispenser was used to transfer 20 µL of RNA stock into all 384 wells of the plate.

The apparent polarization (mP) of each well of the plate was determined using victor V3 or victor V2V plate reader. Each plate was measured in triplicate with a measurement time of 0.4 seconds per well, an excitation band pass filter of 480±31 nm, and an emission band pass filter of 535±40 nm. The data was processed with Microsoft Excel and Wavemetrics Igor Pro. The well score was defined by the following equation:

$$\text{SCORE} = (mP - mP_{average\_no\_protein\_controls}) / (mP_{average\_no\_drug\_controls} - mP_{average\_no\_protein\_controls})$$

Compounds with a score of less than or equal to 0.25 (75% inhibition) where the fluorescence intensity (S) is within 2-fold of the control wells were identified as compounds capable of modulating, e.g., inhibiting, the RNA binding activity of MEX-5.

POS-1: POS-1 inhibitor screening proceeded using the protocol described above, except MBP-POS-1 and BMF018 RNA were used in place of MEX-5 and TCR2 RNA.

MEX-3: MEX-3 screening proceeded as above with the following modifications. MBP-MEX-3 protein and SEQ14 RNA were used in place of MEX-5 and TCR2 RNA. The final concentration of MBP-MEX-3 was reduced to 80 nM in each well, thus the concentration in the protein stock was reduced to 133.3 nM. Zinc acetate was not used in the either the RNA stock or the Protein stock.

Results of the screening assays for each of MEX-5, POS-1 and MEX-3 are shown below in Table 2. Table 2 provides those test compounds which were identified as modulators, e.g., inhibitors, of the RNA binding activity of MEX-5, POS-1 and/or MEX-3, and includes the corresponding scores (where the lowest score correlates to the greatest inhibition) for each compound that were obtained in the assays for each of MEX-5, POS-1 and MEX-3.

TABLE 2

| Compound Code | Structure | MEX-5 | POS-1 | MEX-3 |
|---|---|---|---|---|
| A | 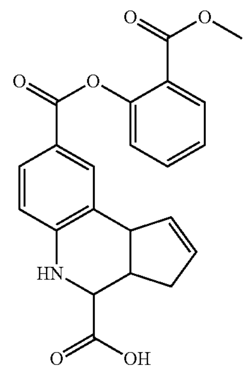 [SMILES: COC(=O)c1ccccc1OC(=O)c1ccc2c(c1)C1C=CCC1C(C(=O)O)N2] | −0.103068 | 0.0750083 | — |
| B | 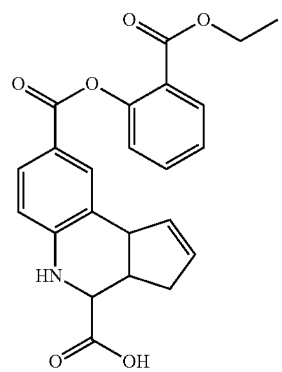 [SMILES: CCOC(=O)c1ccccc1OC(=O)c1ccc2c(c1)C1C=CCC1C(C(=O)O)N2] | −0.0369119 | 0.0551393 | — |
| C | 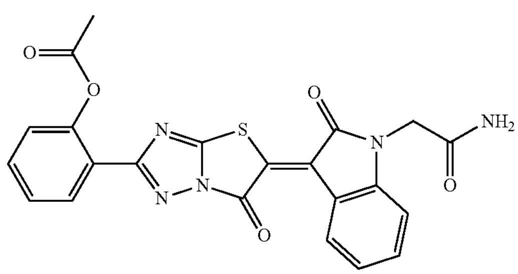 [SMILES: CC(=O)Oc1ccccc1-c1nc2s/c(=C3\C(=O)N(CC(N)=O)c4ccccc43)c(=O)n2n1] | −0.0208829 | −0.0247867 | — |
| D | 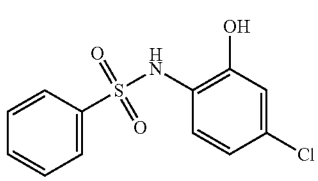 [SMILES: O=S(=O)(Nc1ccc(Cl)cc1O)c1ccccc1] | −0.0158025 | −0.0379222 | — |
| E | 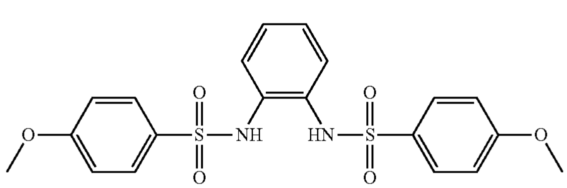 | −0.0106525 | −0.0161771 | — |

TABLE 2-continued

| Compound Code | Structure | MEX-5 | POS-1 | MEX-3 |
|---|---|---|---|---|
| F | 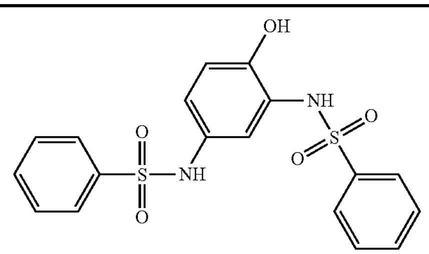 | −0.007108 | −0.0278922 | — |
| G | 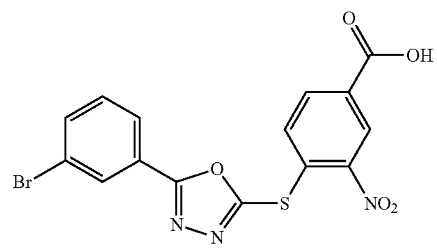 [SMILES: O=C(O)c1ccc(Sc2nnc(-c3cccc(Br)c3)o2)c([N+](=O)[O-])c1] | −0.00640326 | 0.241935 | — |
| H | 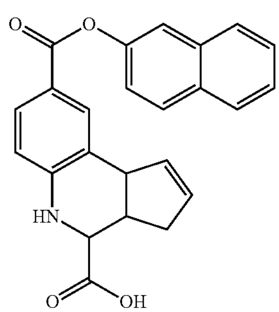 [SMILES: O=C(Oc1ccc2ccccc2c1)c1ccc2c(c1)C1C=CCC1C(C(=O)O)N2] | −0.00335626 | 0.0195217 | — |
| I | 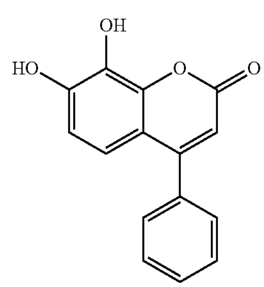 [SMILES: O=c1cc(-c2ccccc2)c2ccc(O)c(O)c2o1] | −0.00142058 | 0.0054316 | — |
| J | 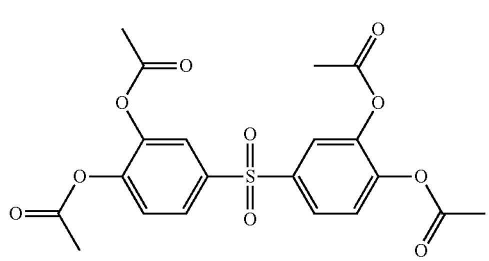 [SMILES: CC(=O)Oc1ccc(S(=O)(=O)c2ccc(OC(C)=O)c(OC(C)=O)c2)cc1OC(C)=O] | −0.000941405 | 0.085093 | — |

TABLE 2-continued
| Compound Code | Structure | MEX-5 | POS-1 | MEX-3 |
|---|---|---|---|---|
| K | 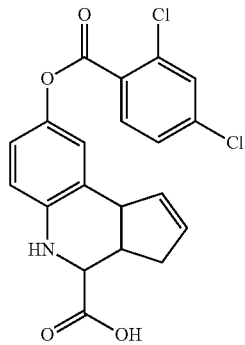 [SMILES: O=C(Oc1ccc2c(c1)C1C=CCC1C(C(=O)O)N2)c1ccc(Cl)cc1Cl] | 1.38E-05 | 0.0581118 | — |
| L | 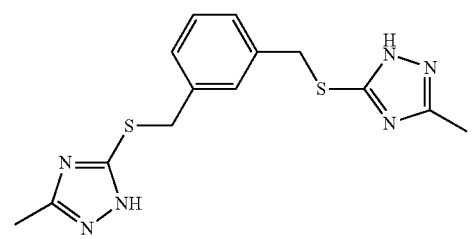 | 0.0121396 | −0.000863837 | — |
| M | 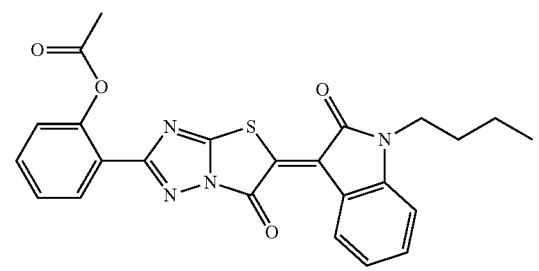 [SMILES: CCCCN1C(=O)/C(=c2\sc3nc(-c4ccccc4OC(C)=O)nn3c2=O)c2ccccc21] | 0.0162117 | 0.116787 | — |
| N | 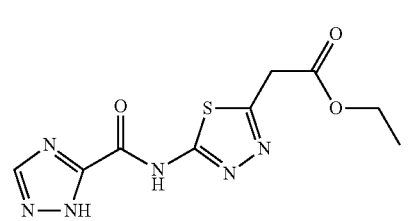 [SMILES: CCOC(=O)Cc1nnc(NC(=O)c2ncn[nH]2)s1] | 0.0208867 | — | — |
| O | 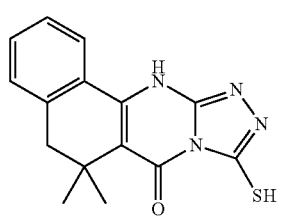 [SMILES: CC1(C)Cc2ccccc2-c2[nH]c3nnc(S)n3c(=O)c21] | 0.0229711 | 0.0476617 | — |
| P | 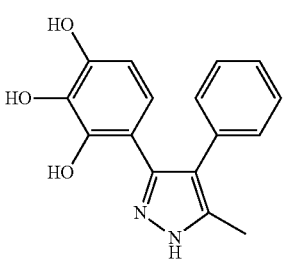 [SMILES: Cc1[nH]nc(-c2ccc(O)c(O)c2O)c1-c1ccccc1] | 0.0341767 | 0.0430453 | — |

TABLE 2-continued

| Compound Code | Structure | MEX-5 | POS-1 | MEX-3 |
|---|---|---|---|---|
| Q | 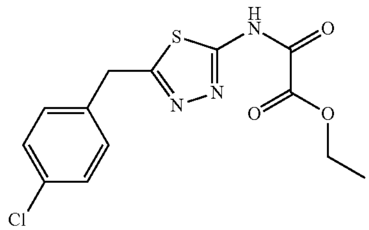 [SMILES: CCOC(=O)C(=O)Nc1nnc(Cc2ccc(Cl)cc2)s1] | 0.0351486 | — | — |
| R | 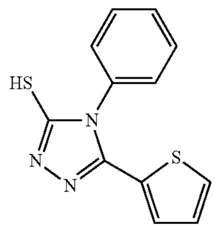 | 0.0351786 | — | — |
| S | 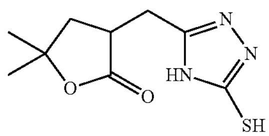 | 0.050021 | 0.105408 | — |
| T | 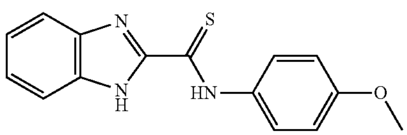 [SMILES: COc1ccc(NC(=S)c2nc3ccccc3[nH]2)cc1] | 0.0550846 | 0.0898578 | — |
| U | 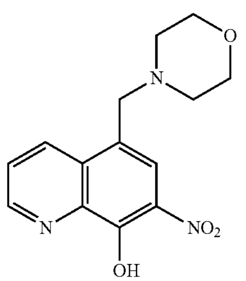 [SMILES: O=[N+]([O-])c1cc(CN2CCOCC2)c2cccnc2c1O] | 0.0621123 | — | — |
| V | 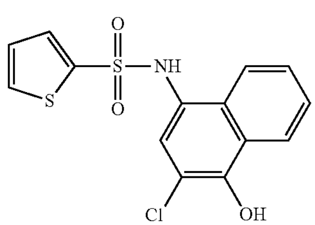 [SMILES: O=S(=O)(Nc1cc(Cl)c(O)c2ccccc12)c1cccs1] | 0.0626293 | — | — |
| W | 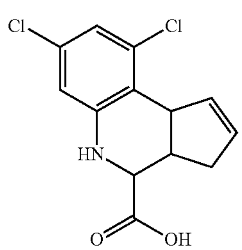 [SMILES: O=C(O)C1Nc2cc(Cl)cc(Cl)c2C2C=CCC12] | 0.064008 | 0.0539474 | — |

TABLE 2-continued
| Compound Code | Structure | MEX-5 | POS-1 | MEX-3 |
|---|---|---|---|---|
| X | 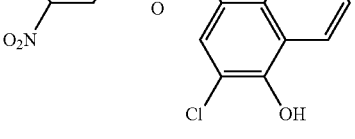 | 0.0668833 | — | — |
| Y | 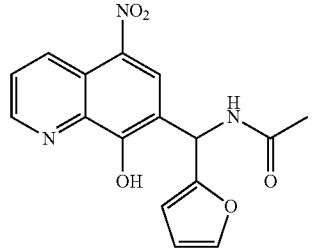 [SMILES: CC(=O)NC(c1ccco1)c1cc([N+](=O)[O-])c2cccnc2c1O] | 0.067749 | 0.0604342 | — |
| Z | 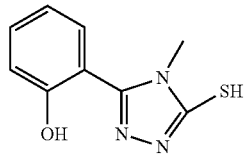 | 0.0687865 | 0.126705 | — |
| AA | 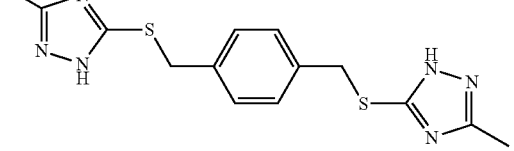 | 0.0713937 | 0.00702445 | — |
| AB | 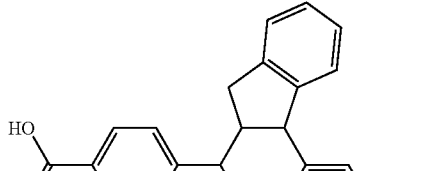 | 0.0730459 | 0.108744 | — |
| AC | 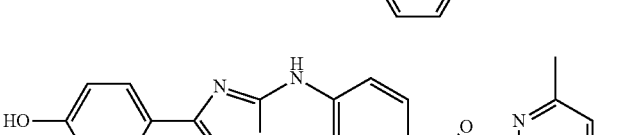 | 0.0758265 | — | — |
| AD | 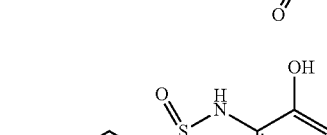 | 0.0803921 | 0.0826922 | — |

TABLE 2-continued

| Compound Code | Structure | MEX-5 | POS-1 | MEX-3 |
|---|---|---|---|---|
| AE | 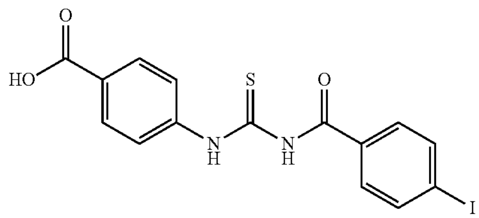 [SMILES: O=C(O)c1ccc(NC(=S)NC(=O)c2ccc(I)cc2)cc1] | 0.0810947 | 0.0360551 | 0.162354 |
| AF | 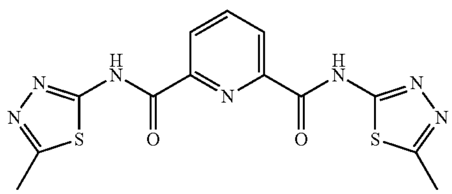 [SMILES: Cc1nnc(NC(=O)c2cccc(C(=O)Nc3nnc(C)s3)n2)s1] | 0.081336 | 0.226509 | — |
| AG | 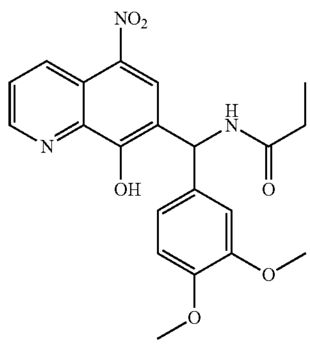 [SMILES: CCC(=O)NC(c1ccc(OC)c(OC)c1)c1cc([N+](=O)[O-])c2cccnc2c1O] | 0.0861502 | — | — |
| AH | 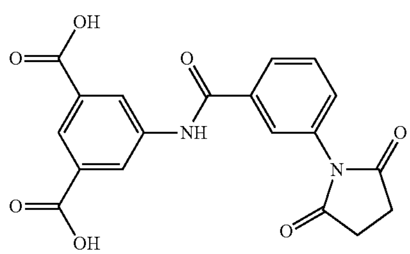 [SMILES: O=C(O)c1cc(NC(=O)c2cccc(N3C(=O)CCC3=O)c2)cc(C(=O)O)c1] | 0.0875937 | 0.145547 | — |
| AI | 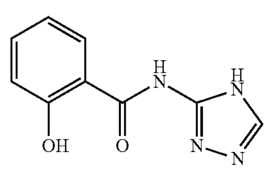 [SMILES: O=C(Nc1nnc[nH]1)c1ccccc1O] | 0.0912883 | 0.0249758 | — |
| AJ | 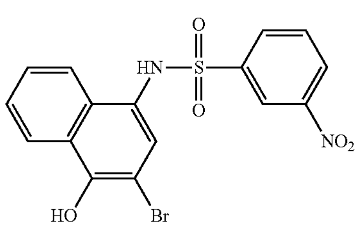 [SMILES: O=[N+]([O-])c1cccc(S(=O)(=O)Nc2cc(Br)c(O)c3ccccc23)c1] | 0.0923393 | — | — |

TABLE 2-continued

| Compound Code | Structure | MEX-5 | POS-1 | MEX-3 |
|---|---|---|---|---|
| AK | 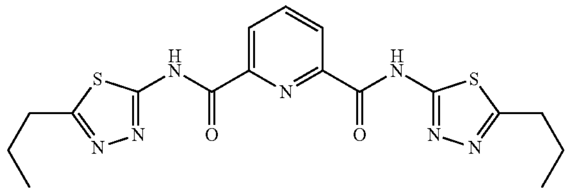 [SMILES: CCCc1nnc(NC(=O)c2cccc(C(=O)Nc3nnc(CCC)s3)n2)s1] | 0.101513 | — | — |
| AL | 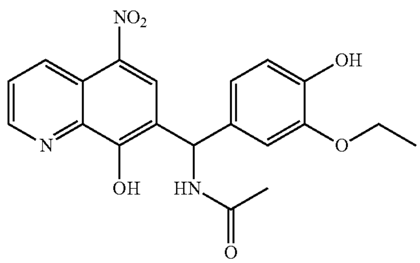 [SMILES: CCOc1cc(C(NC(C)=O)c2cc([N+](=O)[O-])c3cccnc3c2O)ccc1O] | 0.103973 | 0.123145 | — |
| AM | 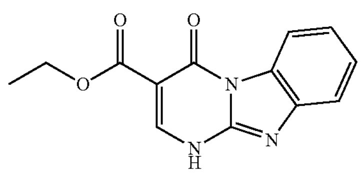 [SMILES: CCOC(=O)c1c[nH]c2nc3ccccc3n2c1=O] | 0.104822 | — | — |
| AN | 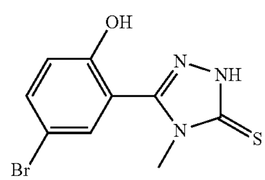 | 0.105086 | — | — |
| AO | 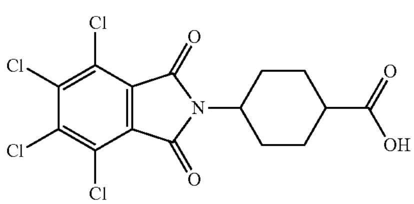 [SMILES: O=C(O)C1CCC(N2C(=O)c3c(Cl)c(Cl)c(Cl)c(Cl)c3C2=O)CC1] | 0.105831 | 0.0681423 | — |
| AP | 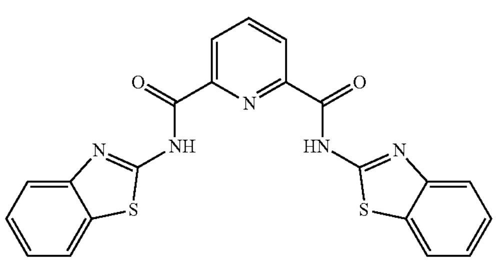 [SMILES: O=C(Nc1nc2ccccc2s1)c1cccc(C(=O)Nc2nc3ccccc3s2)n1] | 0.122397 | — | — |
| AQ | 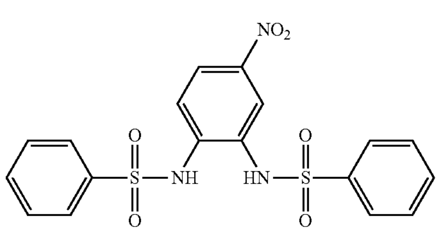 [SMILES: O=[N+]([O-])c1ccc(NS(=O)(=O)c2ccccc2)c(NS(=O)(=O)c2ccccc2)c1] | 0.123778 | 0.115705 | — |

TABLE 2-continued

| Compound Code | Structure | MEX-5 | POS-1 | MEX-3 |
|---|---|---|---|---|
| AR | 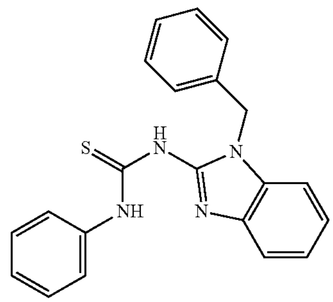 [SMILES: S=C(Nc1ccccc1)Nc1nc2ccccc2n1Cc1ccccc1] | 0.129328 | — | — |
| AS | 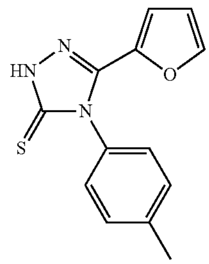 [SMILES: Cc1ccc(-n2c(-c3ccco3)n[nH]c2=S)cc1] | 0.131352 | — | — |
| AT | 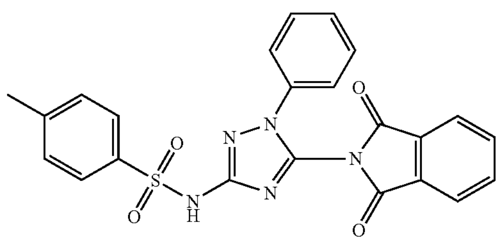 [SMILES: Cc1ccc(S(=O)(=O)Nc2nc(N3C(=O)c4ccccc4C3=O)n(-c3ccccc3)n2)cc1] | 0.132089 | — | — |
| AU | 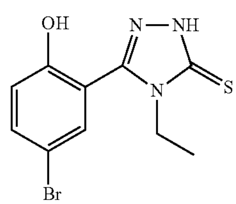 [SMILES: CCn1c(-c2cc(Br)ccc2O)n[nH]c1=S] | 0.134432 | 0.247521 | — |
| AV | 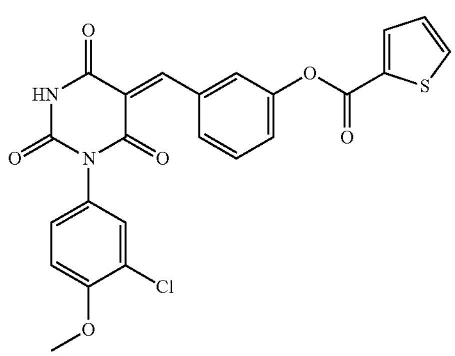 [SMILES: COc1ccc(N2C(=O)NC(=O)/C(=C/c3cccc(OC(=O)c4cccs4)c3)C2=O)cc1Cl] | 0.140139 | 0.109312 | — |
| AW | 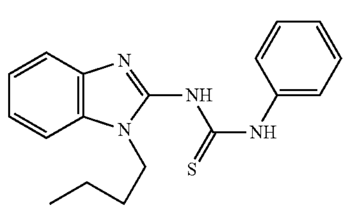 [SMILES: CCCCn1c(NC(=S)Nc2ccccc2)nc2ccccc21] | 0.140504 | — | — |

TABLE 2-continued

| Compound Code | Structure | MEX-5 | POS-1 | MEX-3 |
|---|---|---|---|---|
| AX | 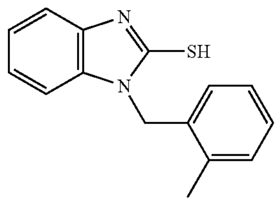 [SMILES: Cc1ccccc1Cn1c(S)nc2ccccc21] | 0.141245 | — | — |
| AY | 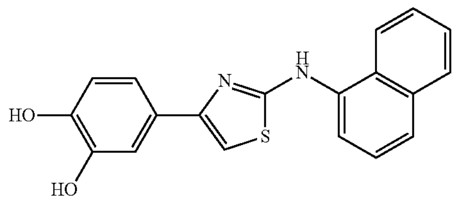 [SMILES: Oc1ccc(-c2csc(Nc3cccc4ccccc34)n2)cc1O] | 0.141274 | 0.180409 | — |
| AZ | 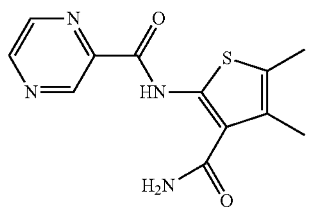 [SMILES: Cc1sc(NC(=O)c2cnccn2)c(C(N)=O)c1C] | 0.143526 | 0.253527 | — |
| BA | 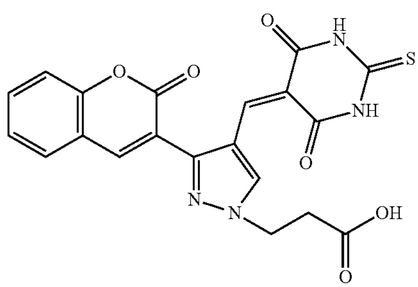 [SMILES: O=C(O)CCn1cc(C=C2C(=O)NC(=S)NC2=O)c(-c2cc3ccccc3oc2=O)n1] | 0.151983 | 0.221567 | — |
| BB | 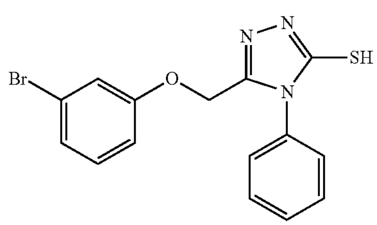 [SMILES: Sc1nnc(COc2cccc(Br)c2)n1-c1ccccc1] | 0.153606 | — | — |
| BC | 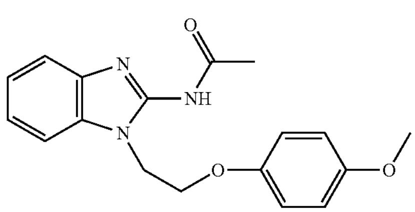 [SMILES: COc1ccc(OCCn2c(NC(C)=O)nc3ccccc32)cc1] | 0.154715 | — | — |
| BD | 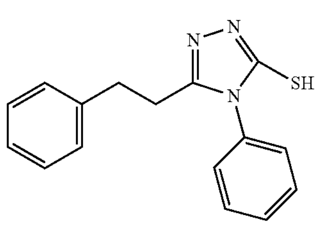 [SMILES: Sc1nnc(CCc2ccccc2)n1-c1ccccc1] | 0.154759 | — | — |

TABLE 2-continued

| Compound Code | Structure | MEX-5 | POS-1 | MEX-3 |
|---|---|---|---|---|
| BE | 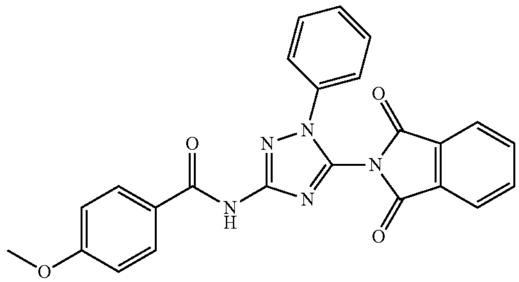 [SMILES: COc1ccc(C(=O)Nc2nc(N3C(=O)c4ccccc4C3=O)n(-c3ccccc3)n2)cc1] | 0.160602 | — | — |
| BF | 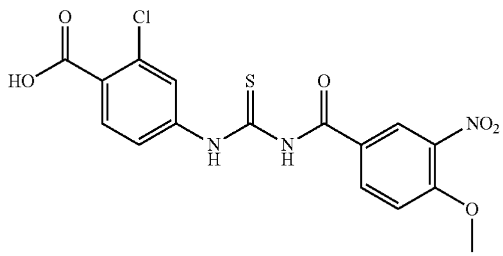 [SMILES: COc1ccc(C(=O)NC(=S)Nc2ccc(C(=O)O)c(Cl)c2)cc1[N+](=O)[O-]] | 0.166567 | 0.0904628 | — |
| BG | 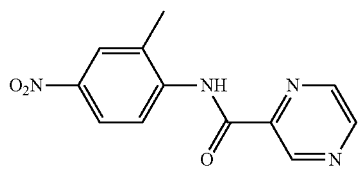 [SMILES: Cc1cc([N+](=O)[O-])ccc1NC(=O)c1cnccn1] | 0.171728 | — | — |
| BH | 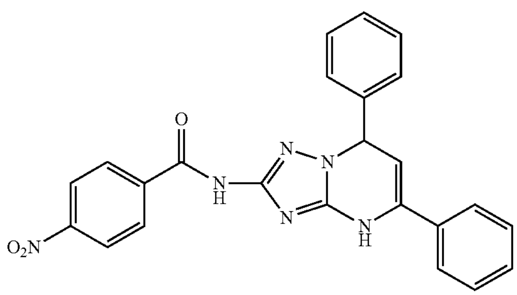 [SMILES: O=C(Nc1nc2n(n1)C(c1ccccc1)C=C(c1ccccc1)N2)c1ccc([N+](=O)[O-])cc1] | 0.176422 | — | — |
| BI | 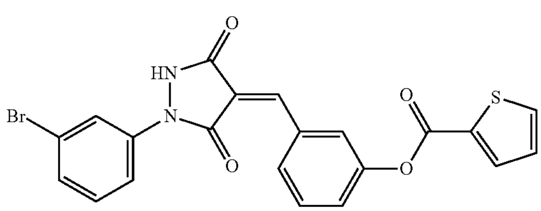 [SMILES: O=C1NN(c2cccc(Br)c2)C(=O)/C1=C\c1cccc(OC(=O)c2cccs2)c1] | 0.178688 | 0.106184 | — |
| BJ | 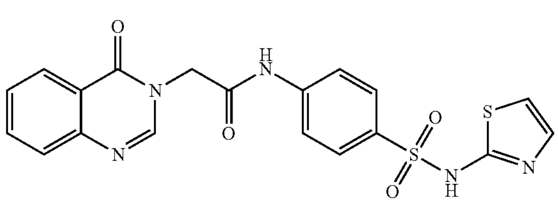 [SMILES: O=C(Cn1cnc2ccccc2c1=O)Nc1ccc(S(=O)(=O)Nc2nccs2)cc1] | 0.181913 | 0.11881 | — |

TABLE 2-continued

| Compound Code | Structure | MEX-5 | POS-1 | MEX-3 |
|---|---|---|---|---|
| BK | 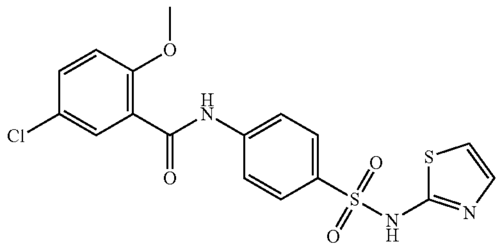 [SMILES: COc1ccc(Cl)cc1C(=O)Nc1ccc(S(=O)(=O)Nc2nccs2)cc1] | 0.183519 | — | — |
| BL | 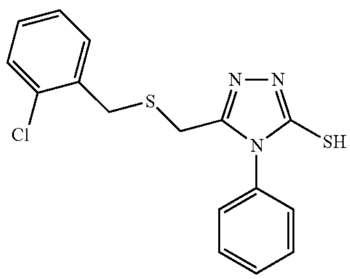 [SMILES: Sc1nnc(CSCc2ccccc2Cl)n1-c1ccccc1] | 0.188022 | 0.275526 | — |
| BM | 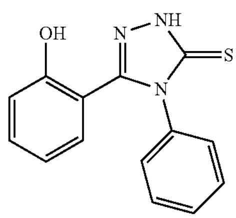 [SMILES: Oc1ccccc1-c1n[nH]c(=S)n1-c1ccccc1] | 0.188023 | — | — |
| BN | 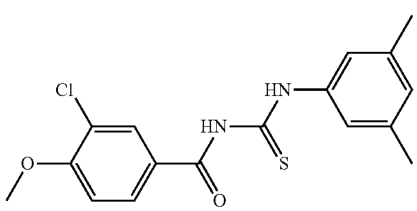 | 0.188711 | — | — |
| BO | 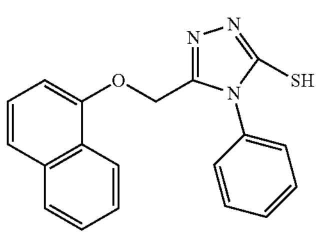 [SMILES: Sc1nnc(COc2cccc3ccccc23)n1-c1ccccc1] | 0.190286 | — | — |
| BP | 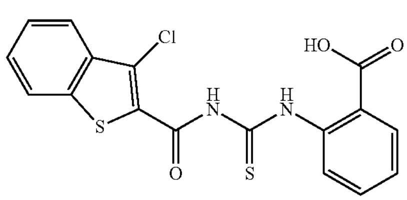 [SMILES: O=C(O)c1ccccc1NC(=S)NC(=O)c1sc2ccccc2c1Cl] | 0.19239 | 0.0454242 | — |

TABLE 2-continued

| Compound Code | Structure | MEX-5 | POS-1 | MEX-3 |
| --- | --- | --- | --- | --- |
| BQ | 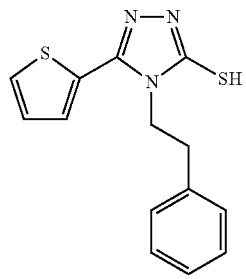 [SMILES: Sc1nnc(-c2cccs2)n1CCc1ccccc1] | 0.195494 | — | — |
| BR | 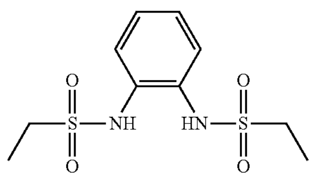 [SMILES: CCS(=O)(=O)Nc1ccccc1NS(=O)(=O)CC] | 0.19904 | — | — |
| BS | 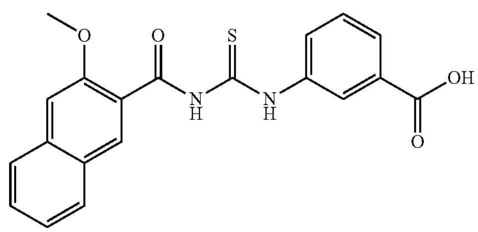 [SMILES: COc1cc2ccccc2cc1C(=O)NC(=S)Nc1cccc(C(=O)O)c1] | 0.200487 | 0.24294 | — |
| BT | 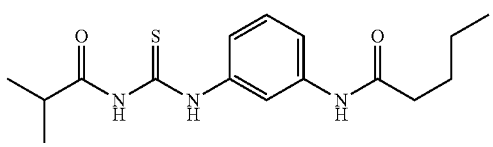 [SMILES: CCCCC(=O)Nc1cccc(NC(=S)NC(=O)C(C)C)c1] | 0.201886 | — | — |
| BU | 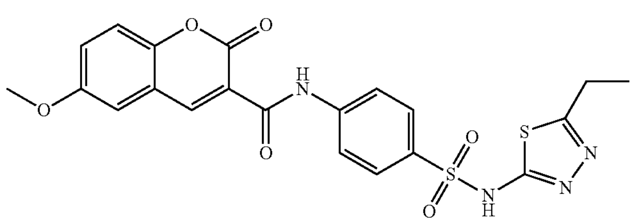 [SMILES: CCc1nnc(NS(=O)(=O)c2ccc(NC(=O)c3cc4cc(OC)ccc4oc3=O)cc2)s1] | 0.208329 | 0.181499 | — |
| BV | 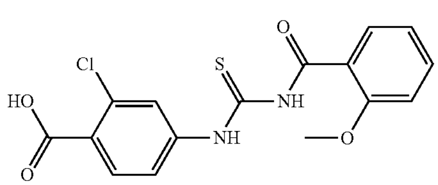 [SMILES: COc1ccccc1C(=O)NC(=S)Nc1ccc(C(=O)O)c(Cl)c1] | 0.211271 | 0.122405 | — |
| BW | 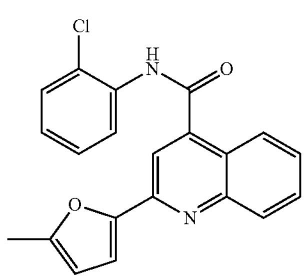 [SMILES: Cc1ccc(-c2cc(C(=O)Nc3ccccc3Cl)c3ccccc3n2)o1] | 0.211513 | — | — |

TABLE 2-continued

| Compound Code | Structure | MEX-5 | POS-1 | MEX-3 |
|---|---|---|---|---|
| BX | 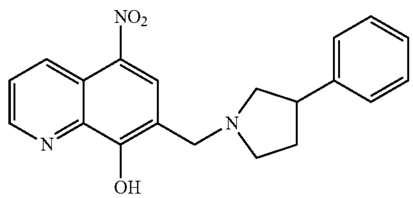 [SMILES: O=[N+]([O-])c1cc(CN2CCC(c3ccccc3)C2)c(O)c2ncccc12] | 0.211718 | — | — |
| BY | 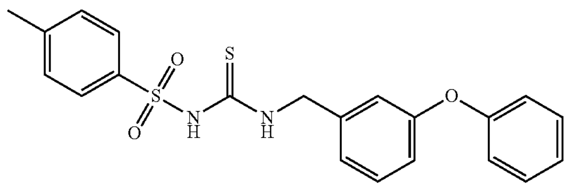 [SMILES: Cc1ccc(S(=O)(=O)NC(=S)NCc2cccc(Oc3ccccc3)c2)cc1] | 0.213189 | 0.143999 | — |
| BZ | 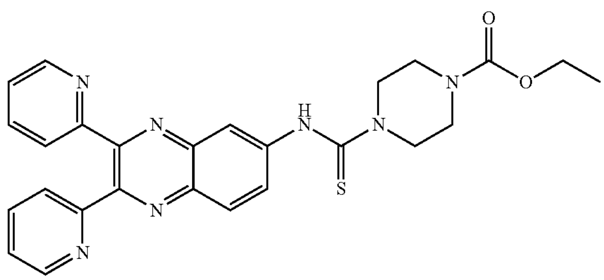 [SMILES: CCOC(=O)N1CCN(C(=S)Nc2ccc3nc(-c4ccccn4)c(-c4ccccn4)nc3c2)CC1] | 0.214246 | — | — |
| CA | 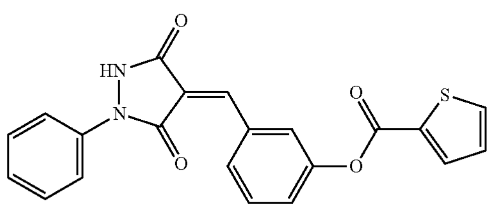 [SMILES: O=C1NN(c2ccccc2)C(=O)/C1=C\c1cccc(OC(=O)c2cccs2)c1] | 0.216367 | 0.230119 | — |
| CB | 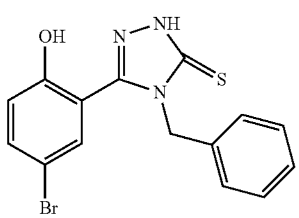 [SMILES: Oc1ccc(Br)cc1-c1n[nH]c(=S)n1Cc1ccccc1] | 0.21706 | 0.23927 | — |
| CC | 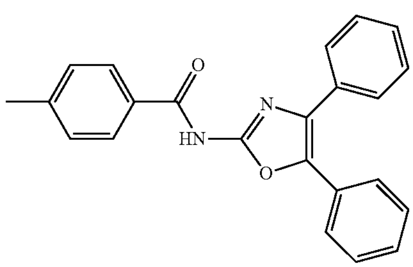 [SMILES: Cc1ccc(C(=O)Nc2nc(-c3ccccc3)c(-c3ccccc3)o2)cc1] | 0.224919 | — | — |
| CD | 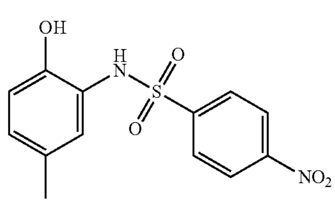 [SMILES: Cc1ccc(O)c(NS(=O)(=O)c2ccc([N+](=O)[O-])cc2)c1] | 0.226379 | 0.123733 | — |

TABLE 2-continued
| Compound Code | Structure | MEX-5 | POS-1 | MEX-3 |
|---|---|---|---|---|
| CE | 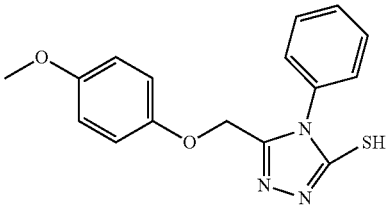 [SMILES: COc1ccc(OCc2nnc(S)n2-c2ccccc2)cc1] | 0.227469 | — | — |
| CF | 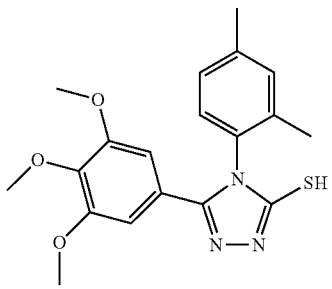 | 0.229065 | — | — |
| CG | 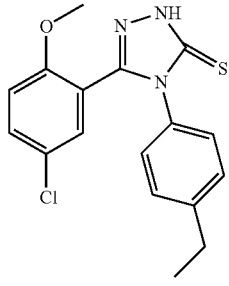 [SMILES: CCc1ccc(-n2c(-c3cc(Cl)ccc3OC)n[nH]c2=S)cc1] | 0.230436 | — | — |
| CH | 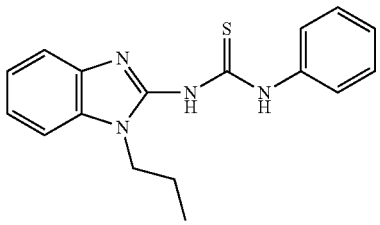 [SMILES: CCCn1c(NC(=S)Nc2ccccc2)nc2ccccc21] | 0.230856 | — | — |
| CI | 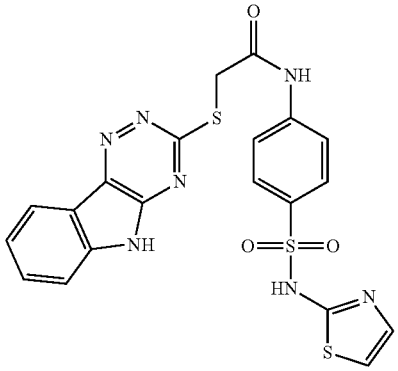 [SMILES: O=C(CSc1nnc2c(n1)[nH]c1ccccc12)Nc1ccc(S(=O)(=O)Nc2nccs2)cc1] | 0.232018 | — | — |
| CJ | 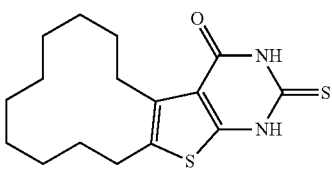 [SMILES: O=c1[nH]c(=S)[nH]c2sc3c(c12)CCCCCCCCCC3] | 0.233565 | — | — |

TABLE 2-continued

| Compound Code | Structure | MEX-5 | POS-1 | MEX-3 |
|---|---|---|---|---|
| CK | 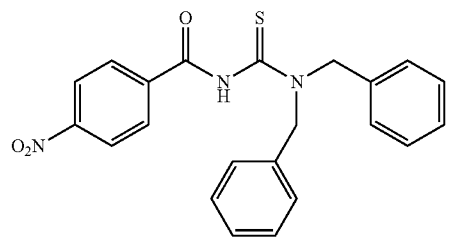 [SMILES: O=C(NC(=S)N(Cc1ccccc1)Cc1ccccc1)c1ccc([N+](=O)[O-])cc1] | 0.233621 | — | — |
| CL | 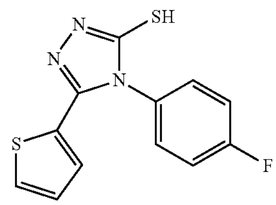 [SMILES: Fc1ccc(-n2c(S)nnc2-c2cccs2)cc1] | 0.235106 | — | — |
| CM | 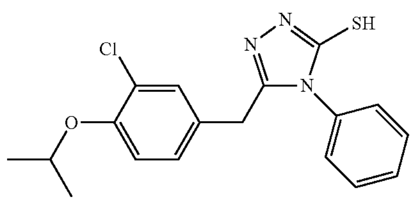 [SMILES: CC(C)Oc1ccc(Cc2nnc(S)n2-c2ccccc2)cc1Cl] | 0.236312 | — | — |
| CN | 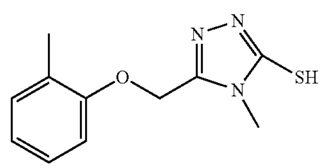 [SMILES: Cc1ccccc1OCc1nnc(S)n1C] | 0.239373 | — | — |
| CO | 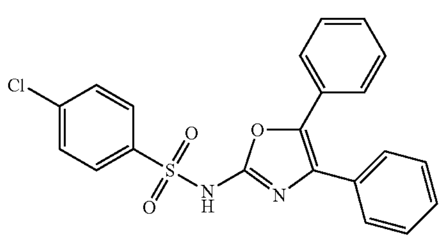 [SMILES: O=S(=O)(Nc1nc(-c2ccccc2)c(-c2ccccc2)o1)c1ccc(Cl)cc1] | 0.240608 | 0.160345 | — |
| CP | 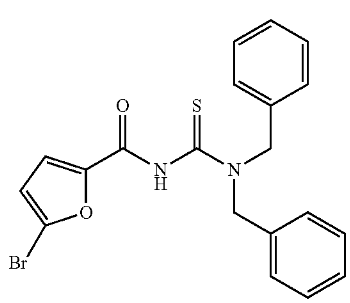 [SMILES: O=C(NC(=S)N(Cc1ccccc1)Cc1ccccc1)c1ccc(Br)o1] | 0.241146 | — | — |

TABLE 2-continued

| Compound Code | Structure | MEX-5 | POS-1 | MEX-3 |
|---|---|---|---|---|
| CQ | 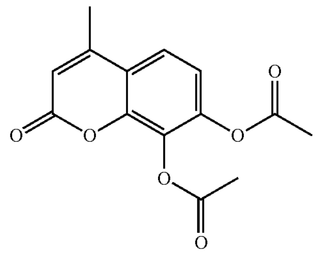 [SMILES: CC(=O)Oc1ccc2c(C)cc(=O)oc2c1OC(C)=O] | 0.245197 | — | — |
| CR | 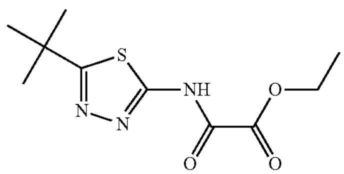 [SMILES: CCOC(=O)C(=O)Nc1nnc(C(C)(C)C)s1] | 0.24654 | — | — |
| CS | 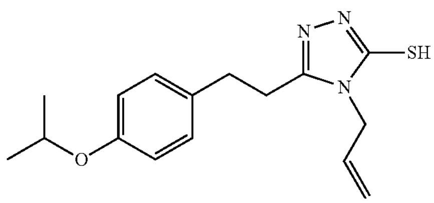 [SMILES: C=CCn1c(S)nnc1CCc1ccc(OC(C)C)cc1] | 0.251831 | — | — |
| CT | 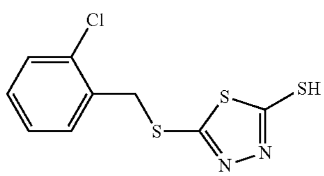 [SMILES: Sc1nnc(SCc2ccccc2Cl)s1] | 0.252156 | — | — |
| CU | 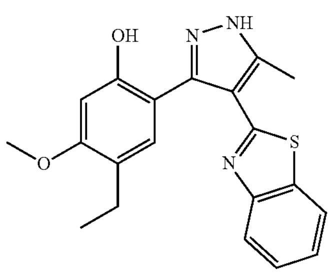 [SMILES: CCc1cc(-c2n[nH]c(C)c2-c2nc3ccccc3s2)c(O)cc1OC] | 0.253312 | — | — |
| CV | 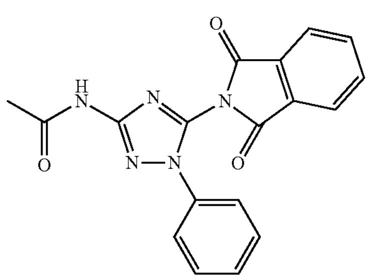 [SMILES: CC(=O)Nc1nc(N2C(=O)c3ccccc3C2=O)n(-c2ccccc2)n1] | 0.255468 | — | — |
| CW | 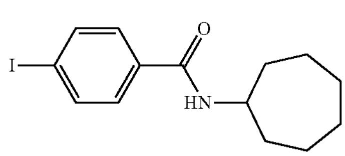 [SMILES: O=C(NC1CCCCCC1)c1ccc(I)cc1] | — | 0.0398467 | — |

TABLE 2-continued

| Compound Code | Structure | MEX-5 | POS-1 | MEX-3 |
|---|---|---|---|---|
| CX | 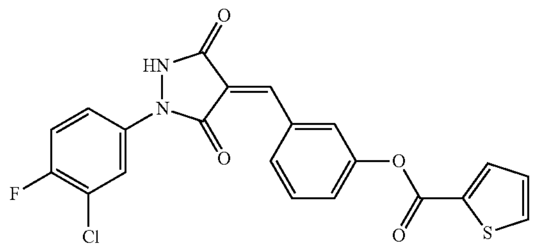 [SMILES: O=C1NN(c2ccc(F)c(Cl)c2)C(=O)/C1=C\c1cccc(OC(=O)c2cccs2)c1] | — | 0.0430453 | — |
| CY | 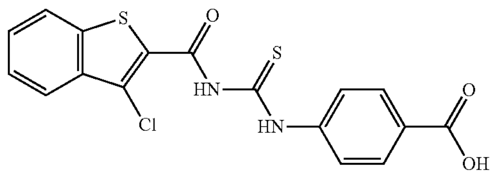 [SMILES: O=C(O)c1ccc(NC(=S)NC(=O)c2sc3ccccc3c2Cl)cc1] | — | 0.0434891 | — |
| CZ | 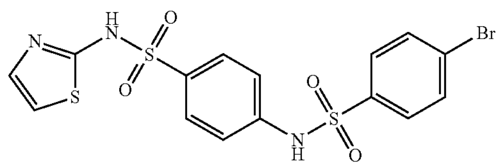 [SMILES: O=S(=O)(Nc1ccc(S(=O)(=O)Nc2nccs2)cc1)c1ccc(Br)cc1] | — | 0.0488653 | — |
| DA | 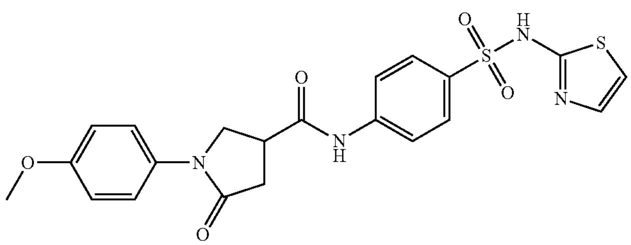 [SMILES: COc1ccc(N2CC(C(=O)Nc3ccc(S(=O)(=O)Nc4nccs4)cc3)CC2=O)cc1] | — | 0.0651114 | — |
| DB | 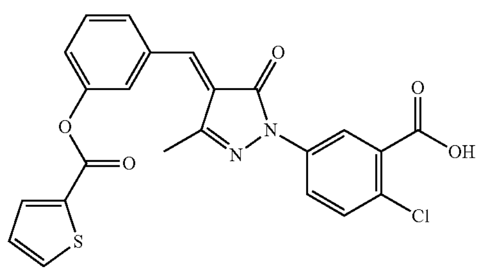 [SMILES: CC1=NN(c2ccc(Cl)c(C(=O)O)c2)C(=O)/C1=C/c1cccc(OC(=O)c2cccs2)c1] | — | 0.0689837 | — |
| DC | 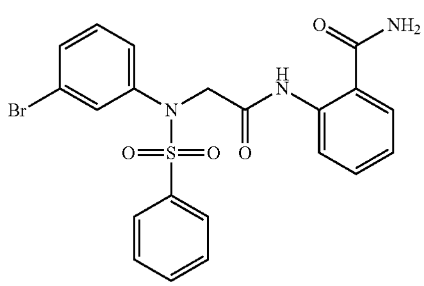 [SMILES: NC(=O)c1ccccc1NC(=O)CN(c1cccc(Br)c1)S(=O)(=O)c1ccccc1] | — | 0.0749757 | — |
| DD | 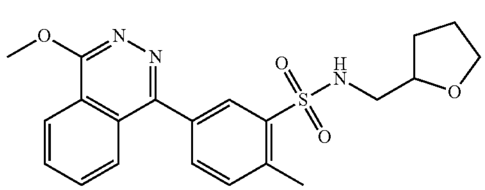 [SMILES: COc1nnc(-c2ccc(C)c(S(=O)(=O)NCC3CCCO3)c2)c2ccccc12] | — | 0.0750083 | — |

TABLE 2-continued

| Compound Code | Structure | MEX-5 | POS-1 | MEX-3 |
|---|---|---|---|---|
| DE | 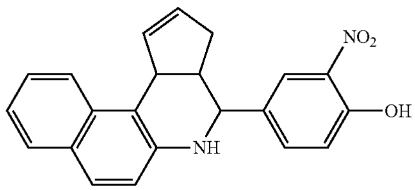 [SMILES: O=[N+]([O-])c1cc(C2Nc3ccc4ccccc4c3C3C=CCC32)ccc1O] | — | 0.0886382 | — |
| DF | 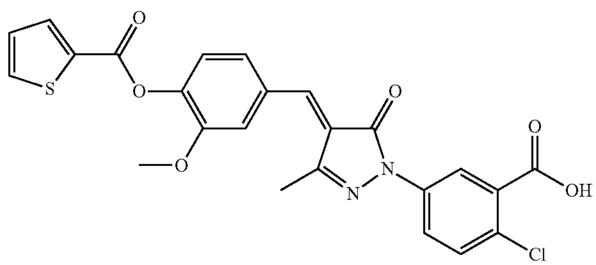 [SMILES: COc1cc(/C=C2/C(=O)N(c3ccc(Cl)c(C(=O)O)c3)N=C2C)ccc1OC(=O)c1cccs1] | — | 0.10079 | — |
| DG | 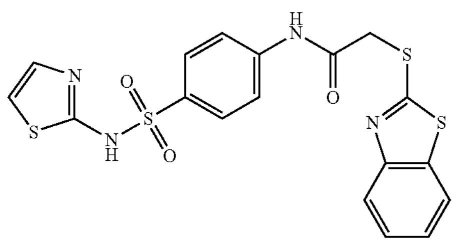 [SMILES: O=C(CSc1nc2ccccc2s1)Nc1ccc(S(=O)(=O)Nc2nccs2)cc1] | — | 0.108633 | — |
| DH | 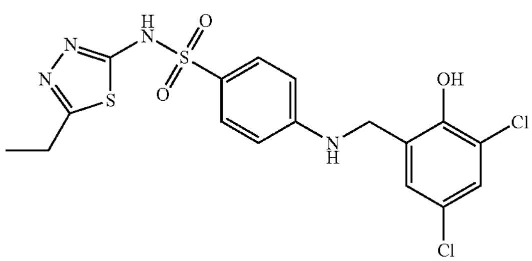 [SMILES: CCc1nnc(NS(=O)(=O)c2ccc(NCc3cc(Cl)cc(Cl)c3O)cc2)s1] | — | 0.118649 | — |
| DI | 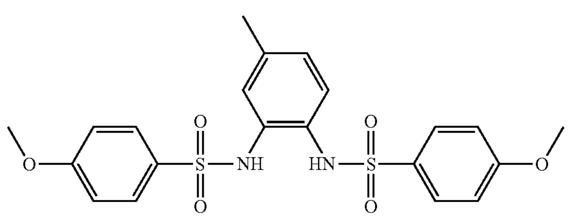 | — | 0.119337 | — |
| DJ | 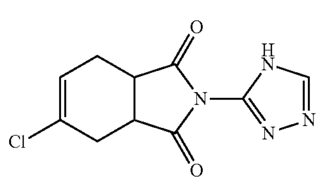 [SMILES: O=C1C2CC=C(Cl)CC2C(=O)N1c1nnc[nH]1] | — | 0.1383 | — |
| DK | 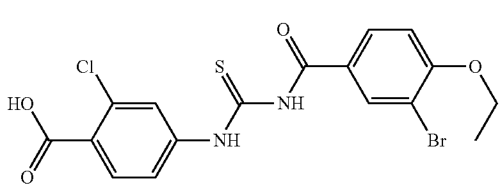 [SMILES: CCOc1ccc(C(=O)NC(=S)Nc2ccc(C(=O)O)c(Cl)c2)cc1Br] | — | 0.142516 | — |

TABLE 2-continued

| Compound Code | Structure | MEX-5 | POS-1 | MEX-3 |
|---|---|---|---|---|
| DL | 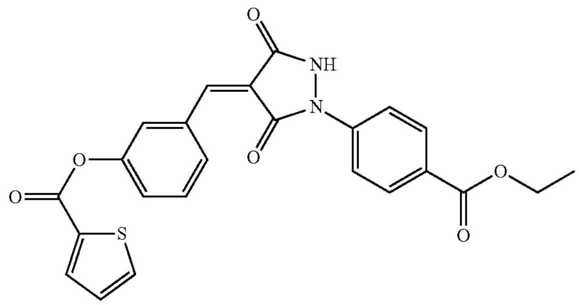 [SMILES: CCOC(=O)c1ccc(N2NC(=O)/C(=C/c3cccc(OC(=O)c4cccs4)c3)C2=O)cc1] | — | 0.1431 | — |
| DM | 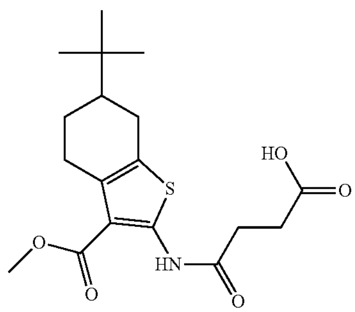 [SMILES: COC(=O)c1c(NC(=O)CCC(=O)O)sc2c1CCC(C(C)(C)C)C2] | — | 0.143623 | — |
| DN | 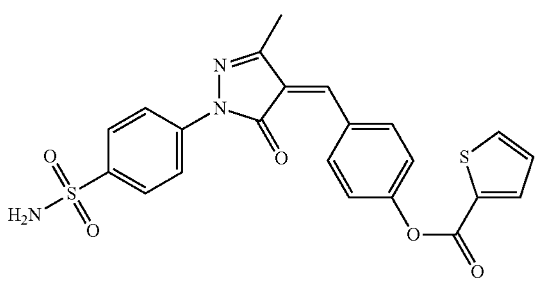 [SMILES: CC1=NN(c2ccc(S(N)(=O)=O)cc2)C(=O)/C1=C\c1ccc(OC(=O)c2cccs2)cc1] | — | 0.166782 | — |
| DO | 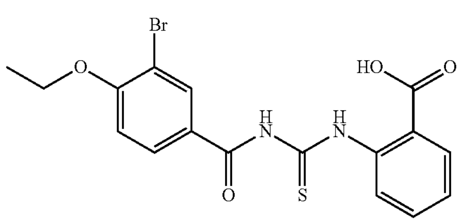 [SMILES: CCOc1ccc(C(=O)NC(=S)Nc2ccccc2C(=O)O)cc1Br] | — | 0.166873 | — |
| DP | 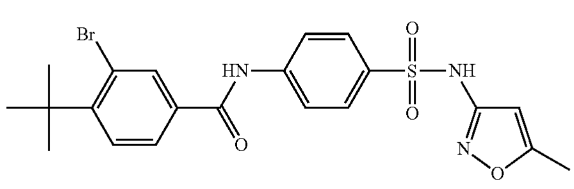 [SMILES: Cc1cc(NS(=O)(=O)c2ccc(NC(=O)c3ccc(C(C)(C)C)c(Br)c3)cc2)no1] | — | 0.167907 | — |

TABLE 2-continued

| Compound Code | Structure | MEX-5 | POS-1 | MEX-3 |
|---|---|---|---|---|
| DQ | 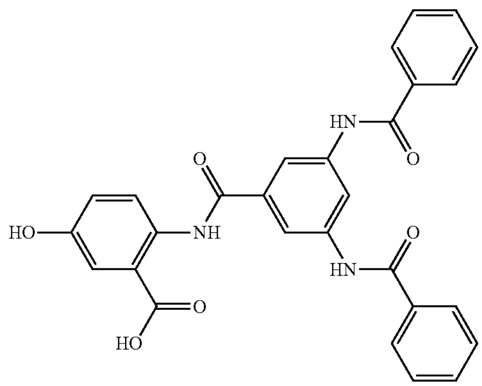 [SMILES: O=C(Nc1cc(NC(=O)c2ccccc2)cc(C(=O)Nc2ccc(O)cc2C(=O)O)c1)c1ccccc1] | — | 0.171713 | — |
| DR | 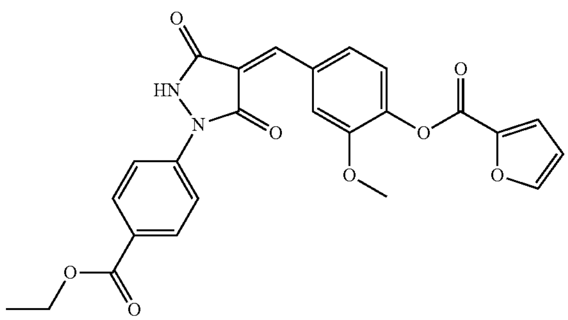 [SMILES: CCOC(=O)c1ccc(N2NC(=O)/C(=C/c3ccc(OC(=O)c4ccco4)c(OC)c3)C2=O)cc1] | — | 0.171815 | — |
| DS | 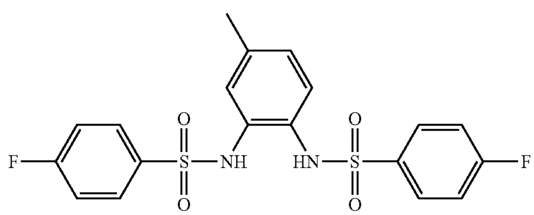 [SMILES: Cc1ccc(NS(=O)(=O)c2ccc(F)cc2)c(NS(=O)(=O)c2ccc(F)cc2)c1] | — | 0.176583 | — |
| DT | 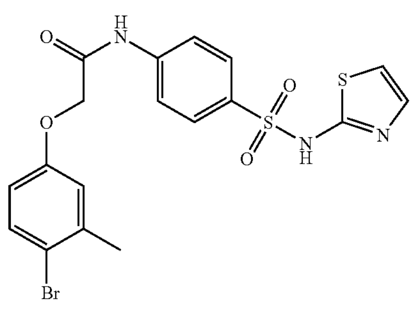 [SMILES: Cc1cc(OCC(=O)Nc2ccc(S(=O)(=O)Nc3nccs3)cc2)ccc1Br] | — | 0.177235 | — |
| DU | 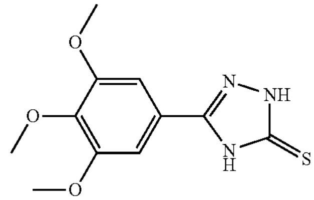 [SMILES: COc1cc(-c2n[nH]c(=S)[nH]2)cc(OC)c1OC] | — | 0.180302 | — |

TABLE 2-continued

| Compound Code | Structure | MEX-5 | POS-1 | MEX-3 |
|---|---|---|---|---|
| DV | 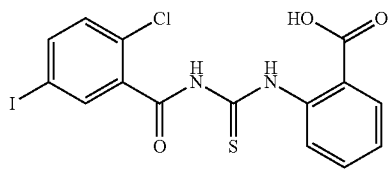 [SMILES: O=C(NC(=S)Nc1ccccc1C(=O)O)c1cc(I)ccc1Cl] | — | 0.184556 | — |
| DW | 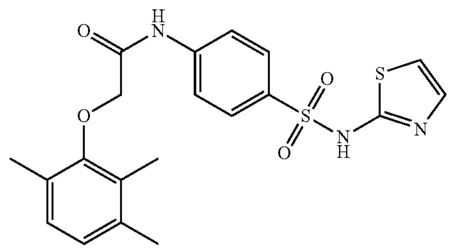 [SMILES: Cc1ccc(C)c(OCC(=O)Nc2ccc(S(=O)(=O)Nc3nccs3)cc2)c1C] | — | 0.189883 | — |
| DX | 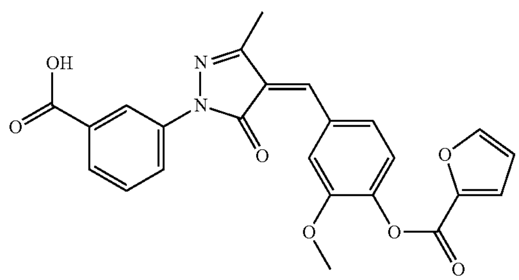 [SMILES: COc1cc(/C=C2\C(=O)N(c3cccc(C(=O)O)c3)N=C2C)ccc1OC(=O)c1ccco1] | — | 0.196968 | — |
| DY | 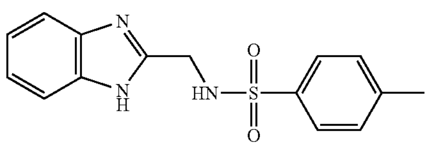 [SMILES: Cc1ccc(S(=O)(=O)NCc2nc3ccccc3[nH]2)cc1] | — | 0.200285 | — |
| DZ | 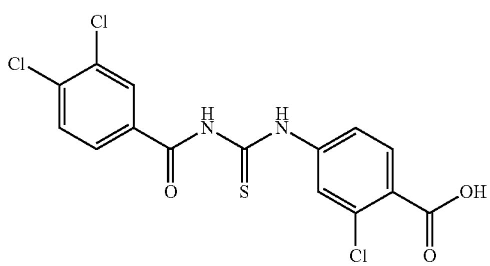 [SMILES: O=C(NC(=S)Nc1ccc(C(=O)O)c(Cl)c1)c1ccc(Cl)c(Cl)c1] | — | 0.20137 | — |
| EA | 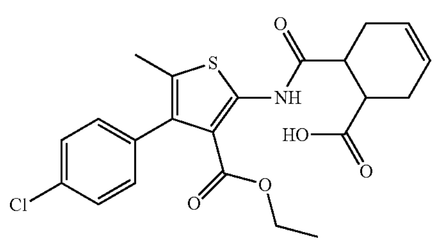 [SMILES: CCOC(=O)c1c(NC(=O)C2CC=CCC2C(=O)O)sc(C)c1-c1ccc(Cl)cc1] | — | 0.203009 | — |
| EB | 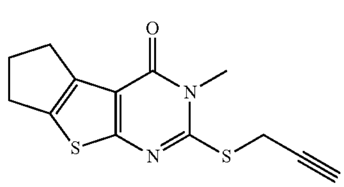 [SMILES: C#CCSc1nc2sc3c(c2c(=O)n1C)CCC3] | — | 0.209605 | — |

TABLE 2-continued

| Compound Code | Structure | MEX-5 | POS-1 | MEX-3 |
|---|---|---|---|---|
| EC | 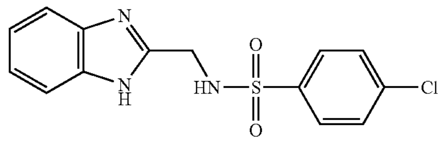 [SMILES: O=S(=O)(NCc1nc2ccccc2[nH]1)c1ccc(Cl)cc1] | — | 0.217393 | — |
| ED | 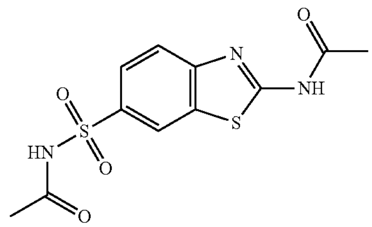 [SMILES: CC(=O)Nc1nc2ccc(S(=O)(=O)NC(C)=O)cc2s1] | — | 0.220348 | — |
| EE | 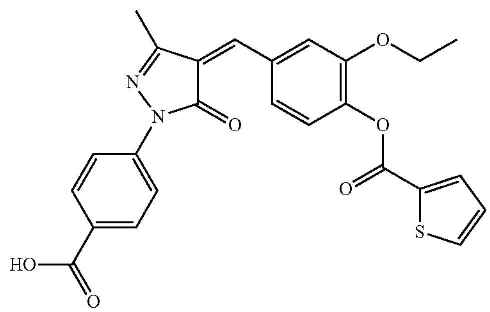 [SMILES: CCOc1cc(/C=C2\C(=O)N(c3ccc(C(=O)O)cc3)N=C2C)ccc1OC(=O)c1cccs1] | — | 0.225108 | — |
| EF | 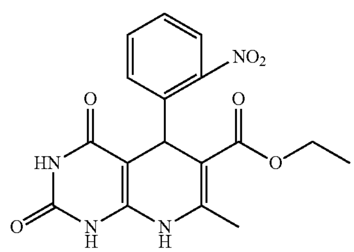 [SMILES: CCOC(=O)C1=C(C)Nc2[nH]c(=O)[nH]c(=O)c2C1c1ccccc1[N+](=O)[O-]] | — | 0.228172 | — |
| EG | 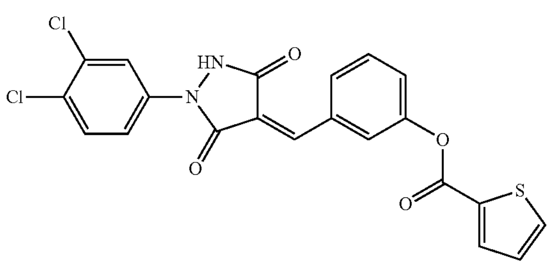 [SMILES: O=C1NN(c2ccc(Cl)c(Cl)c2)C(=O)/C1=C/c1cccc(OC(=O)c2cccs2)c1] | — | 0.229412 | — |
| EH | 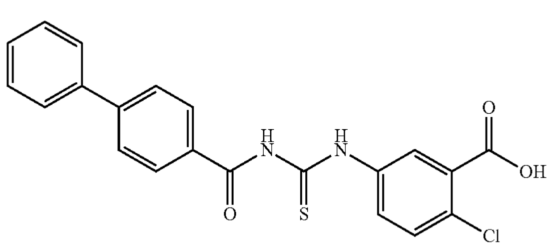 [SMILES: O=C(NC(=S)Nc1ccc(Cl)c(C(=O)O)c1)c1ccc(-c2ccccc2)cc1] | — | 0.230119 | — |

TABLE 2-continued

| Compound Code | Structure | MEX-5 | POS-1 | MEX-3 |
|---|---|---|---|---|
| EI | 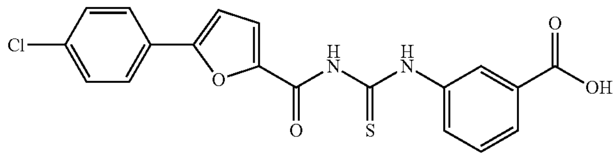 [SMILES: O=C(O)c1cccc(NC(=S)NC(=O)c2ccc(-c3ccc(Cl)cc3)o2)c1] | — | 0.230383 | — |
| EJ | 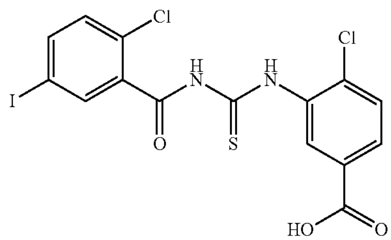 [SMILES: O=C(O)c1ccc(Cl)c(NC(=S)NC(=O)c2cc(I)ccc2Cl)c1] | — | 0.233942 | — |
| EK | 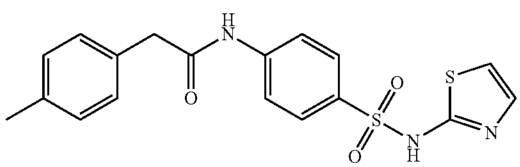 [SMILES: Cc1ccc(CC(=O)Nc2ccc(S(=O)(=O)Nc3nccs3)cc2)cc1] | — | 0.236507 | — |
| EL | 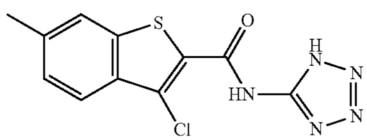 [SMILES: Cc1ccc2c(Cl)c(C(=O)Nc3nnn[nH]3)sc2c1] | — | 0.237867 | — |
| EM | 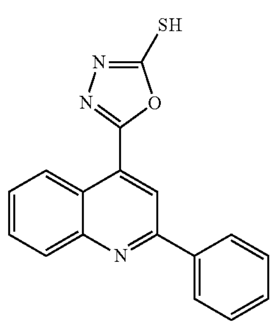 [SMILES: Sc1nnc(-c2cc(-c3ccccc3)nc3ccccc23)o1] | — | 0.241791 | — |
| EN | 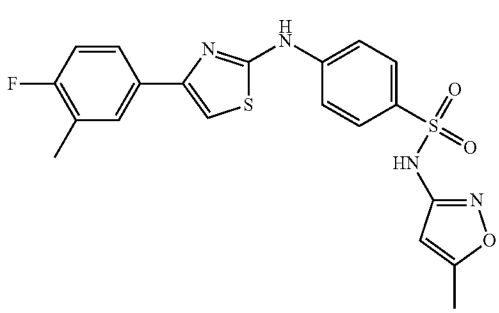 [SMILES: Cc1cc(NS(=O)(=O)c2ccc(Nc3nc(-c4ccc(F)c(C)c4)cs3)cc2)no1] | — | 0.247036 | — |
| EO | 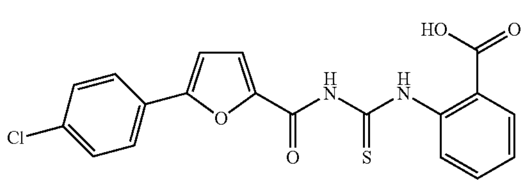 [SMILES: O=C(NC(=S)Nc1ccccc1C(=O)O)c1ccc(-c2ccc(Cl)cc2)o1] | — | 0.253668 | — |

TABLE 2-continued

| Compound Code | Structure | MEX-5 | POS-1 | MEX-3 |
|---|---|---|---|---|
| EP | 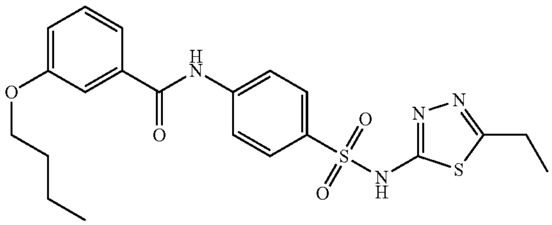 [SMILES: CCCCOc1cccc(C(=O)Nc2ccc(S(=O)(=O)Nc3nnc(CC)s3)cc2)c1] | — | 0.259513 | — |
| EQ | 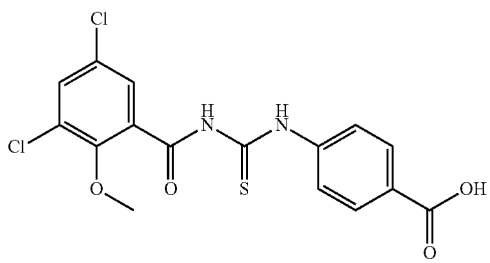 [SMILES: COc1c(Cl)cc(Cl)cc1C(=O)NC(=S)Nc1ccc(C(=O)O)cc1] | — | 0.26035 | — |
| ER | 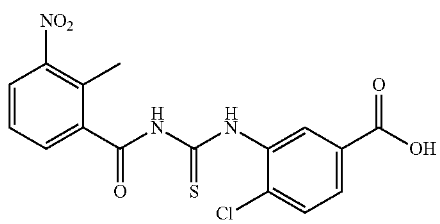 [SMILES: Cc1c(C(=O)NC(=S)Nc2cc(C(=O)O)ccc2Cl)cccc1[N+](=O)[O-]] | — | 0.261571 | — |
| ES | 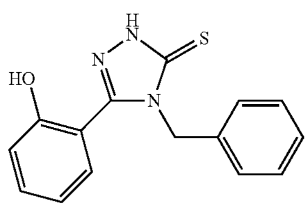 [SMILES: Oc1ccccc1-c1n[nH]c(=S)n1Cc1ccccc1] | — | 0.26453 | — |
| ET | 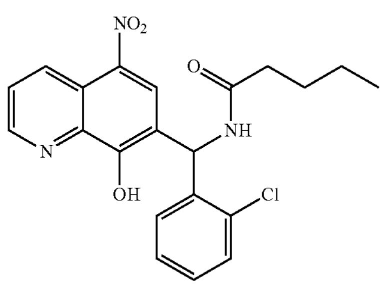 [SMILES: CCCCC(=O)NC(c1ccccc1Cl)c1cc([N+](=O)[O-])c2cccnc2c1O] | — | 0.265118 | — |
| EU | 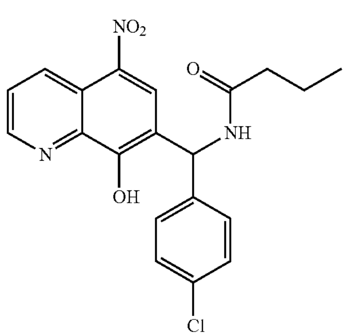 [SMILES: CCCC(=O)NC(c1ccc(Cl)cc1)c1cc([N+](=O)[O-])c2cccnc2c1O] | — | 0.26601 | — |

TABLE 2-continued

| Compound Code | Structure | MEX-5 | POS-1 | MEX-3 |
|---|---|---|---|---|
| EV | 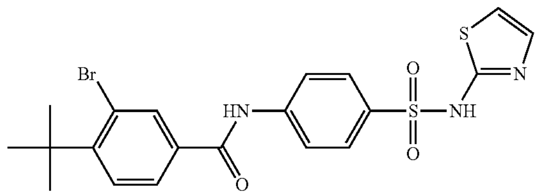 [SMILES: CC(C)(C)c1ccc(C(=O)Nc2ccc(S(=O)(=O)Nc3nccs3)cc2)cc1Br] | — | 0.274806 | — |
| EW | 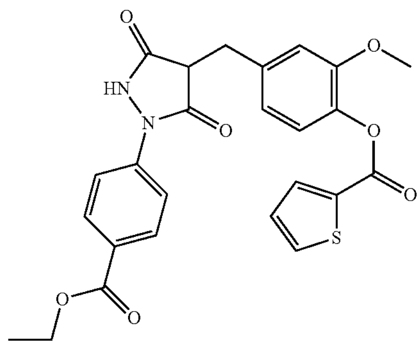 [SMILES: CCOC(=O)c1ccc(N2NC(=O)C(Cc3ccc(OC(=O)c4cccs4)c(OC)c3)C2=O)cc1] | — | 0.275235 | — |
| EX | 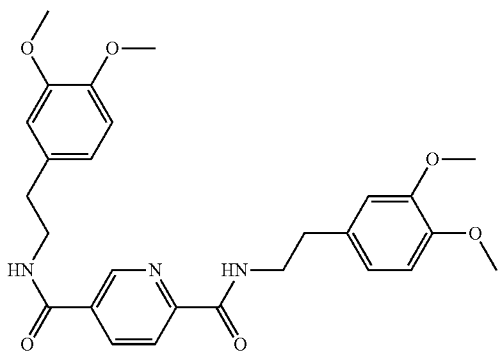 [SMILES: COc1ccc(CCNC(=O)c2ccc(C(=O)NCCc3ccc(OC)c(OC)c3)nc2)cc1OC] | — | — | 0.0673989 |
| EY | 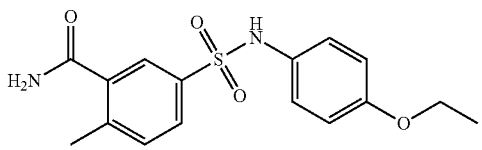 [SMILES: CCOc1ccc(NS(=O)(=O)c2ccc(C)c(C(N)=O)c2)cc1] | — | — | 0.0896497 |
| EZ | 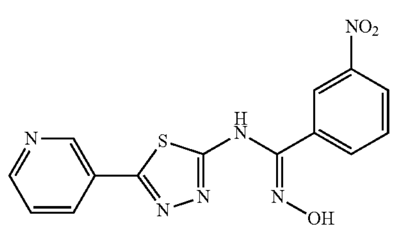 [SMILES: O=[N+]([O-])c1cccc(/C(=N\O)Nc2nnc(-c3cccnc3)s2)c1] | — | — | 0.123959 |
| FA | 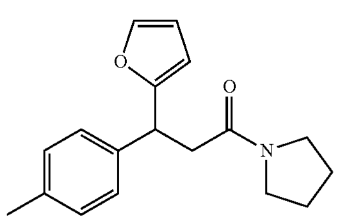 [SMILES: Cc1ccc(C(CC(=O)N2CCCC2)c2ccco2)cc1] | — | — | 0.209341 |

TABLE 2-continued

| Compound Code | Structure | MEX-5 | POS-1 | MEX-3 |
|---|---|---|---|---|
| FB | (structure) | — | — | 0.258457 |

Further screenings were performed on select compounds of the invention, as described above, and the results are shown in Table 3.

TABLE 3

| Compound | Dose Response MEX-5 (μM) | Dose Response POS-1 (μM) |
|---|---|---|
| E | 1.5 | 0.32 |
| BR | 39 | 820 |
| BK | 540 | ND |
| DG | 160 | ND |
| DD | ND | 300 |
| DJ | 3.5 | ND |
| C | 33 | 7 |
| BO | 75 | 16 |

Example 2

Hermaphrodite Worm Reproduction Assay

In order to further evaluate the ability of a particular RNA binding modulatory compound identified herein to inhibit embryogenesis, e.g., in a nematode, the compounds identified herein are tested in a standard hermaphrodite worm reproduction assay s. Larval worms are hatched overnight into medium containing the compound in an agar plate. Then, feeder bacteria is added to each plate and the worms cultured until they begin to produce eggs. Adult worms are removed or killed. Finally, the ratio of dead eggs to hatchlings is determined by inspection with a stereomicroscope.

Example 4

Dose Response Gel Shift Assays

A further dose response assay was performed on select compounds of the invention as described below. A sub-saturating concentration of MEX-5 or POS-1 (120 nM) was equilibrated with limiting fluorescein labeled RNA (2-3 nM, TCR2 RNA or MEX-3 UTR fragment RNA respectively) in the presence of varying concentrations of compound. Following equilibration, the reactions were loaded onto a 5% slab polyacrylamide gel and subjected to electrophoresis for about 1 hour to separate protein-RNA complex from free RNA. The gel was scanned on a FUJI FLA-5000 imager, and the fraction of bound RNA determined by dividing the intensity of the bound RNA by the intensity of the bound RNA plus the free RNA. The fraction of the compound bound to the protein was plotted as a function of compound concentration and fit to a sigmoidal dose response function in order to determine the $IC_{50}$, the concentration that gives half maximal inhibition. The results are seen in Table 4.

TABLE 4

| Compound | Gel Shift MEX-5 (μM) | Gel Shift POS-1 (μM) |
|---|---|---|
| E | 2.0 | 0.17 |
| BR | 78 | 150 |
| BK | 110 | ND |
| DG | 170 | ND |
| DD | ND | 260 |
| DJ | 3.8 | ND |
| C | 9.5 | 5.1 |
| BO | 120 | 33 |

Example 5

C. elegans Viability/Sterility Assay

In order to determine whether select compounds of the invention inhibited viability of embryos, Caenorhabditis elegans N2 strain worms were cultured on NGM agar plates using OP50 strain Escherchia coli as food. Young adult worms with a single row of embryos were selected for microinjection. Each worm was mounted on a dried agarose padded coverslip in halocarbon oil. Varying concentrations of compound, or a DMSO control, were microinjected into each gonad arm of the worm using an inverted microscope with DIC optics. Injected worms were then allowed to recover for 2-3 hours at 15° C. Approximately 10-40 worms were injected per compound tested. Individual worms that survived microinjection were singled out onto new NGM agar plates and allowed to recover overnight at 15° C. The plates were moved to room temperature the next morning. At the end of the day, the adult worm was transferred to a new plate. The embryos laid on each plate were monitored for hatching and inspected for unusual phenotypes. Nematode fertility was estimated by counting the total number of progeny on both plates. Viability was estimated by monitoring the extent of hatching. The results of this assay using compound E are shown below in Table 5.

TABLE 5

| Worm No. | Day 1 Embryos | Day 1 Hatchlings | Day 2 Embryos | Day 2 Hatchlings |
|---|---|---|---|---|
| 1 | 0 | 34 | 0 | 0 |
| 2 | 0 | 2 | 0 | 0 |
| 3 | 2 | 6 | 0 | 0 |
| 4 | 0 | 4 | 0 | 0 |
| 5 | 0 | 67 | 0 | 0 |
| 6 | 1 | 11 | 0 | 0 |

The results of this assay indicate that compound E may sterilize worms at a stage prior to fertilization. The worms seemed to lose fertility over the course of two days. In contrast, 27 worms were injected with DMSO controls, 10 survived injection, and they continued to produce eggs afterwards.

EQUIVALENTS

Those skilled in the art will recognize, or be able to ascertain using no more than routine experimentation, numerous equivalents to the specific polypeptides, nucleic acids, methods, assays and reagents described herein. Such equivalents are considered to be within the scope of this invention and are covered by the following claims.

---

The invention claimed is:

1. A method for treating or preventing a parasitic associated state in a subject comprising administering to said subject an effective amount of compound E:

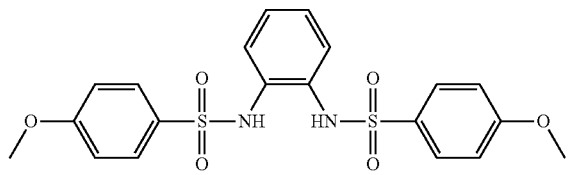

or a pharmaceutically acceptable salt thereof, such that said parasitic associated state is treated or prevented, wherein compound E modulates the RNA binding activity of an RNA binding protein selected from a group consisting of POS-1 and MEX-5.

2. The method of claim 1, wherein said subject is a plant, an animal or a human.

3. The method of claim 1, wherein said parasitic associated state is a parasitic infestation or parasitic re-infestation or a disease caused by a parasitic infestation.

4. The method of claim 1, wherein said method includes protecting plants from a parasitic infestation, inhibiting embryogenesis in a parasite or in a subject suffering from a parasitic infestation, or reducing parasitic burden in soil, in plants or in an animal suffering from a parasitic infection.

5. The method of any one of claims 1, 2, 3 and 4, wherein said parasite is a helminth.

6. The method of claim 5, wherein said helminth is selected from the group consisting of a cestode, a trematode and a nematode.

7. A method for inhibiting embryogenesis in a parasite, comprising contacting said parasite with an effective amount of compound E:

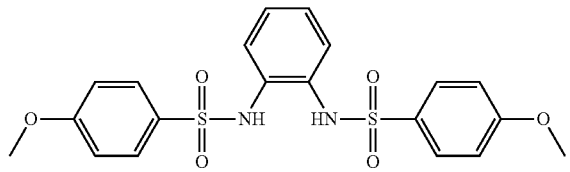

or a pharmaceutically acceptable salt thereof, such that said embryogenesis is inhibited, wherein compound E modulates the RNA binding activity of an RNA binding protein selected from a group consisting of POS-1 and MEX-5.

8. The method of claim 7, wherein the parasite is present in a subject.

9. The method of claim 7 or 8, wherein said parasite is a helminth.

10. The method of claim 9, wherein said helminth is selected from the group consisting of a cestode, a trematode and a nematode.

11. A method for treating or preventing an inflammatory disorder caused by a parasitic associated state in a subject comprising administering to said subject a therapeutically effective amount of compound E:

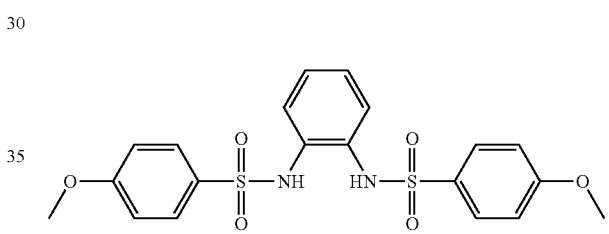

or a pharmaceutically acceptable salt thereof, such that said inflammatory disorder is treated or prevented, wherein compound E modulates the RNA binding activity of an RNA binding protein selected from a group consisting of POS-1 and MEX-5.

12. The method of claims 1, 7 and 11, wherein the RNA binding protein is required for embryogenesis.

13. A pharmaceutical composition comprising a therapeutically effective amount of compound E:

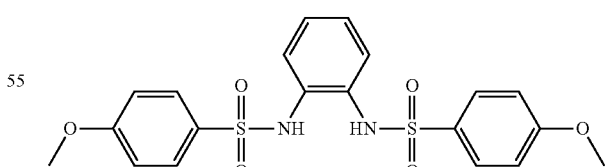

or a pharmaceutically acceptable salt thereof, and a pharmaceutically acceptable carrier, wherein compound E modulates the RNA binding activity of an RNA binding protein selected from a group consisting of POS-1 and MEX-5.

14. A composition comprising a pesticidally effective amount of compound E:

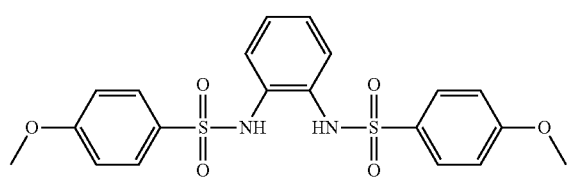

and an agronomically acceptable carrier, wherein compound E modulates the RNA binding activity of an RNA binding protein selected from a group consisting of POS-1 and MEX-5.

15. A method for treating or preventing a parasitic associated state in a subject comprising administering to said subject an effective amount of compound DI:

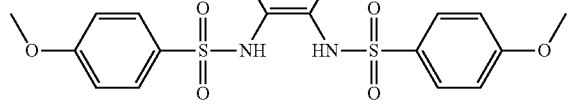

or a pharmaceutically acceptable salt thereof, such that said parasitic associate state is treated or prevented, wherein compound DI modulates the RNA binding activity of an RNA binding protein POS-1.

16. The method of claim 15, wherein said subject is a plant, an animal or a human.

17. The method of claim 15, wherein said parasitic associated state is a parasitic infestation or parasitic re-infestation or a disease cause by a parasitic infestation.

18. The method of claim 15, wherein said method includes protecting plants from a parasitic infestation, inhibiting embryogenesis in a parasite or in a subject suffering from a parasitic infestation, or reducing parasitic burden in soil, in plants or in an animal suffering from parasitic infection.

19. The method of any one of claims 15-18, wherein said parasite is a helminth.

20. The method of claim 19, wherein said helminth is selected from the group consisting of a cestode, a trematode and a nematode.

21. A method for inhibiting embryogenesis in a parasite, comprising contacting said parasite with an effective amount of compound DI:

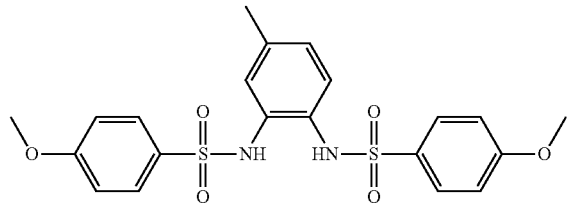

or a pharmaceutically acceptable salt thereof, such that said embryogenesis is inhibited, wherein compound DI modulates binding activity of an RNA binding protein POS-1.

22. The method of claim 21, wherein the parasite is present in a subject.

23. The method of claim 21 or 22, wherein said parasite is a helminth.

24. The method of claim 23, wherein said helminth is selected from the group consisting of a cestode, a trematode and a nematode.

25. A method for treating or preventing an inflammatory disorder caused by a parasitic associated state in a subject comprising administering to said subject a therapeutically effective amount of compound DI:

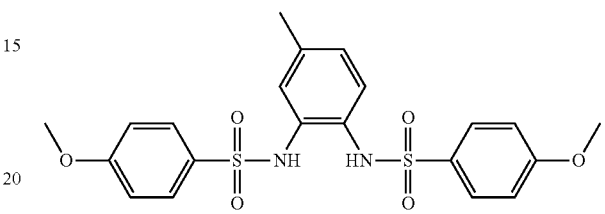

or pharmaceutically acceptable salt thereof, such that said inflammatory disorder is treated or prevented, wherein compound DI modulates the RNA binding activity of an RNA binding protein POS-1.

26. The method of claims 15, 21 and 25, wherein the RNA binding protein is required for embryogenesis.

27. A pharmaceutical composition comprising a therapeutically effective amount of compound DI:

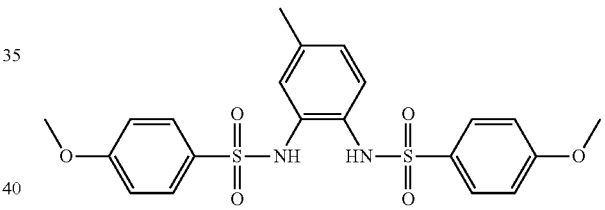

or pharmaceutically acceptable salt thereof, and a pharmaceutically acceptable carrier, wherein compound DI modulates the RNA binding activity of an RNA binding protein POS-1.

28. A composition comprising a pesticidally effective amount of compound DI:

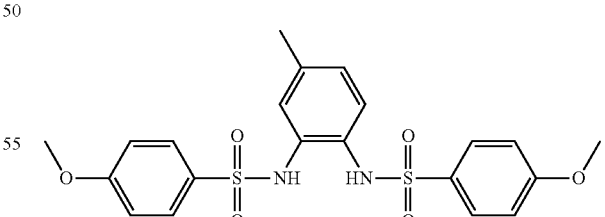

and an agronomically acceptable carrier, wherein compound DI modulates the RNA binding activity of an RNA binding protein POS-1.

* * * * *

SEQUENCE LISTING

<160> NUMBER OF SEQ ID NOS: 5

<210> SEQ ID NO 1
<211> LENGTH: 30
<212> TYPE: RNA
<213> ORGANISM: Artificial Sequence
<220> FEATURE:
<223> OTHER INFORMATION: Synthetic oligonucleotide: MEX-5 binding RNA
      (TCR2)

<400> SEQUENCE: 1
uuucuuuaua acuuguuaca auuuuugaaa                                          30

<210> SEQ ID NO 2
<211> LENGTH: 28
<212> TYPE: RNA
<213> ORGANISM: Artificial Sequence
<220> FEATURE:
<223> OTHER INFORMATION: Synthetic oligonucleotide: POS-1 binding RNA
      (BMF018)

<400> SEQUENCE: 2
aacuauuauu auuguuauu cauauuuu                                             28

<210> SEQ ID NO 3
<211> LENGTH: 30
<212> TYPE: RNA
<213> ORGANISM: Artificial Sequence
<220> FEATURE:
<223> OTHER INFORMATION: Synthetic oligonucleotide: MEX-3 binding RNA
      (SEQ14)

<400> SEQUENCE: 3
cgagcaggaa gugugcagag uuuaggacgu                                          30

<210> SEQ ID NO 4
<211> LENGTH: 30
<212> TYPE: RNA
<213> ORGANISM: Artificial Sequence
<220> FEATURE:
<223> OTHER INFORMATION: Synthetic oligonucleotide: Fluorescent TCR2
      RNA
<220> FEATURE:
<221> NAME/KEY: misc_feature
<223> OTHER INFORMATION: FITC label on 3' end

<400> SEQUENCE: 4
uuucuuuaua acuuguuaca auuuuugaaa                                          30

<210> SEQ ID NO 5
<211> LENGTH: 28

```
<212> TYPE: RNA
<213> ORGANISM: Artificial Sequence
<220> FEATURE:
<223> OTHER INFORMATION: Synthetic oligonucleotide: Fluorescent mex3
      RNA
<220> FEATURE:
<221> NAME/KEY: misc_feature
<223> OTHER INFORMATION: FITC label on 3' end

<400> SEQUENCE: 5
aacuauuauu auuuguuauu cauauuuu                                           28
```